(12) United States Patent
Alaswad et al.

(10) Patent No.: US 11,779,362 B1
(45) Date of Patent: Oct. 10, 2023

(54) METHODS AND APPARATUS FOR TRUE LUMEN RE-ENTRY

(71) Applicant: TruVue, Inc., Kalamazoo, MI (US)

(72) Inventors: Khaldoon Alaswad, Grosse Point Park, MI (US); Tim A. Fischell, Kalamazoo, MI (US)

(73) Assignee: TruVue, Inc., Kalamazoo, MI (US)

( * ) Notice: Subject to any disclaimer, the term of this patent is extended or adjusted under 35 U.S.C. 154(b) by 0 days.

(21) Appl. No.: 18/165,913

(22) Filed: Feb. 7, 2023

Related U.S. Application Data

(60) Provisional application No. 63/370,032, filed on Aug. 1, 2022.

(51) Int. Cl.
*A61B 17/22* (2006.01)

(52) U.S. Cl.
CPC .... *A61B 17/22* (2013.01); *A61B 2017/22069* (2013.01); *A61B 2017/22074* (2013.01)

(58) Field of Classification Search
CPC .......... A61B 17/22; A61B 2017/22069; A61B 2017/22074; A61B 8/12; A61B 8/445; A61B 8/4461; A61B 2090/3784; A61B 8/0841; A61B 5/02007; A61B 8/4483; A61B 8/0891; A61B 2090/3782
See application file for complete search history.

(56) References Cited

U.S. PATENT DOCUMENTS

| | | | | |
|---|---|---|---|---|
| 5,803,083 A | * | 9/1998 | Buck | A61B 8/445 600/439 |
| 6,475,226 B1 | * | 11/2002 | Belef | A61B 17/11 606/170 |
| 6,544,230 B1 | * | 4/2003 | Flaherty | A61B 17/22 604/164.12 |
| 6,709,444 B1 | * | 3/2004 | Makower | A61M 25/0084 606/198 |
| 6,726,677 B1 | * | 4/2004 | Flaherty | A61B 17/3417 604/528 |
| 2003/0236542 A1 | * | 12/2003 | Makower | A61B 17/12109 606/167 |
| 2007/0208256 A1 | * | 9/2007 | Marilla | A61B 5/02007 600/467 |
| 2009/0131798 A1 | * | 5/2009 | Minar | A61B 5/02007 600/463 |
| 2013/0190803 A1 | * | 7/2013 | Angel | A61F 2/011 606/200 |
| 2013/0303897 A1 | * | 11/2013 | Pursley | A61B 5/0084 600/467 |
| 2020/0000524 A1 | * | 1/2020 | Stigall | A61B 8/445 |
| 2020/0000525 A1 | * | 1/2020 | Stigall | A61B 8/445 |
| 2020/0022751 A1 | * | 1/2020 | Denison | A61B 18/06 |

* cited by examiner

*Primary Examiner* — Patrick Fernandes
(74) *Attorney, Agent, or Firm* — Shay Glenn LLP

(57) ABSTRACT

A catheter for facilitating re-entry of a re-entry wire into a true lumen or into any desired region of a blood vessel may have an elongate shaft with a first lumen. A distal port and a first proximal port are fluidly coupled with the first lumen. A wire re-entry port is adjacent the distal end of the elongate shaft. The wire re-entry port has a re-entry axis. An ultrasound transducer on the catheter is configured to produce an image the blood vessel, and has a central axis that allows visualization of the re-entry wire as it exits the re-entry port and re-enters the true lumen. This allows the operator to ensure that the re-entry wire re-enters the true lumen in a desired location and does not damage the vessel.

34 Claims, 105 Drawing Sheets

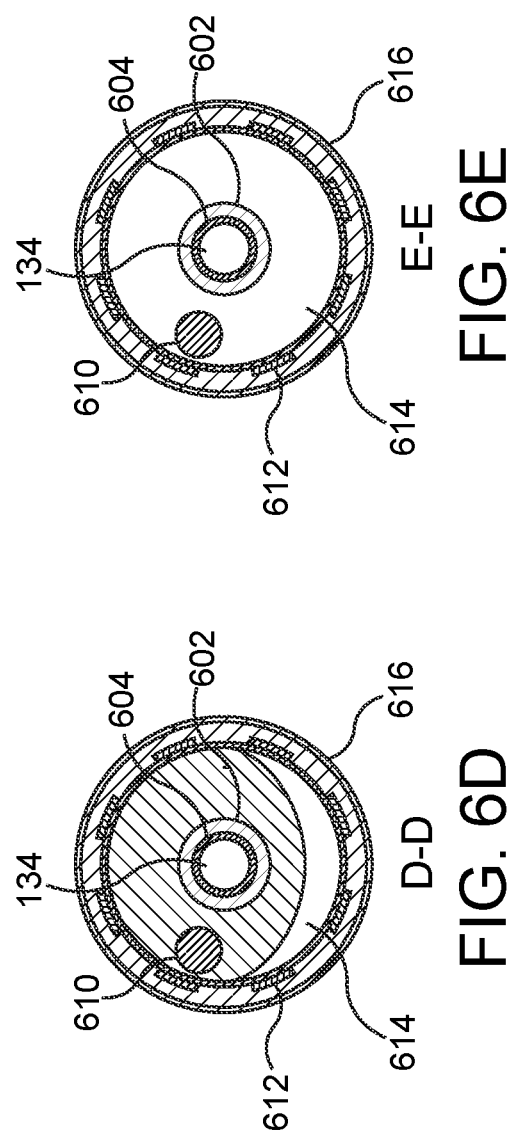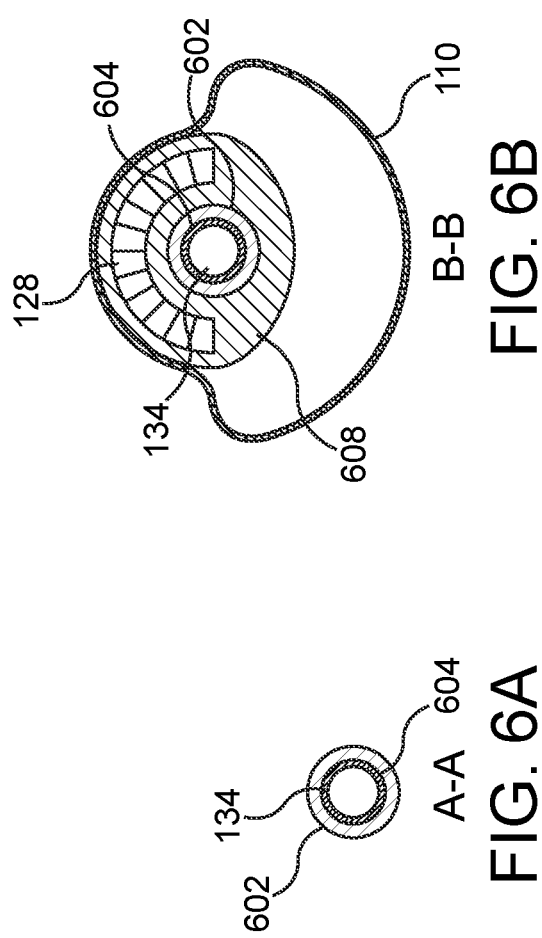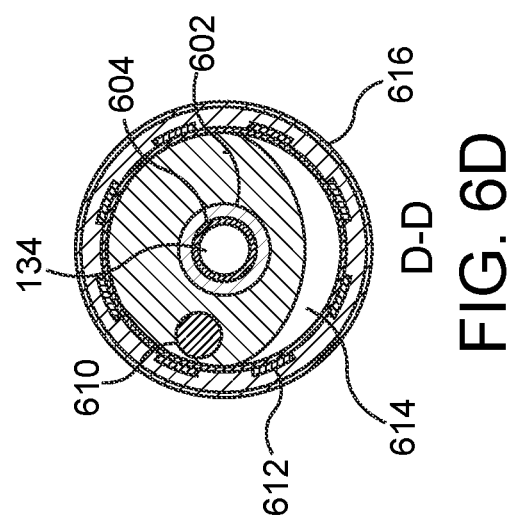

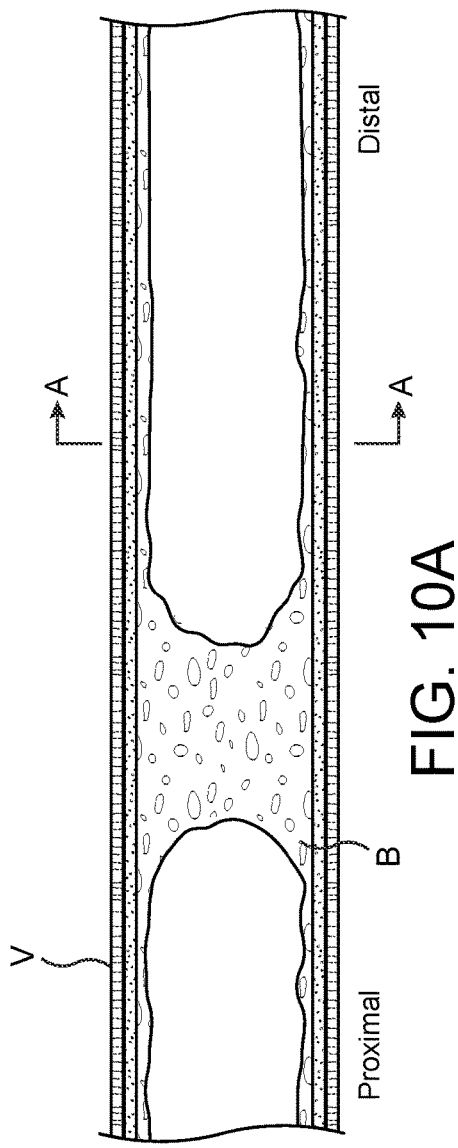
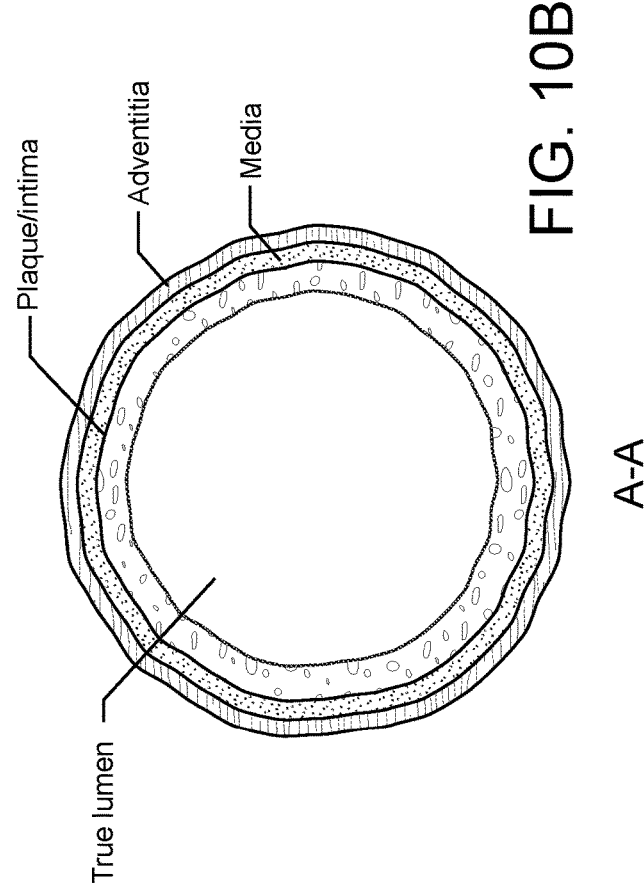
FIG. 10A
FIG. 10B

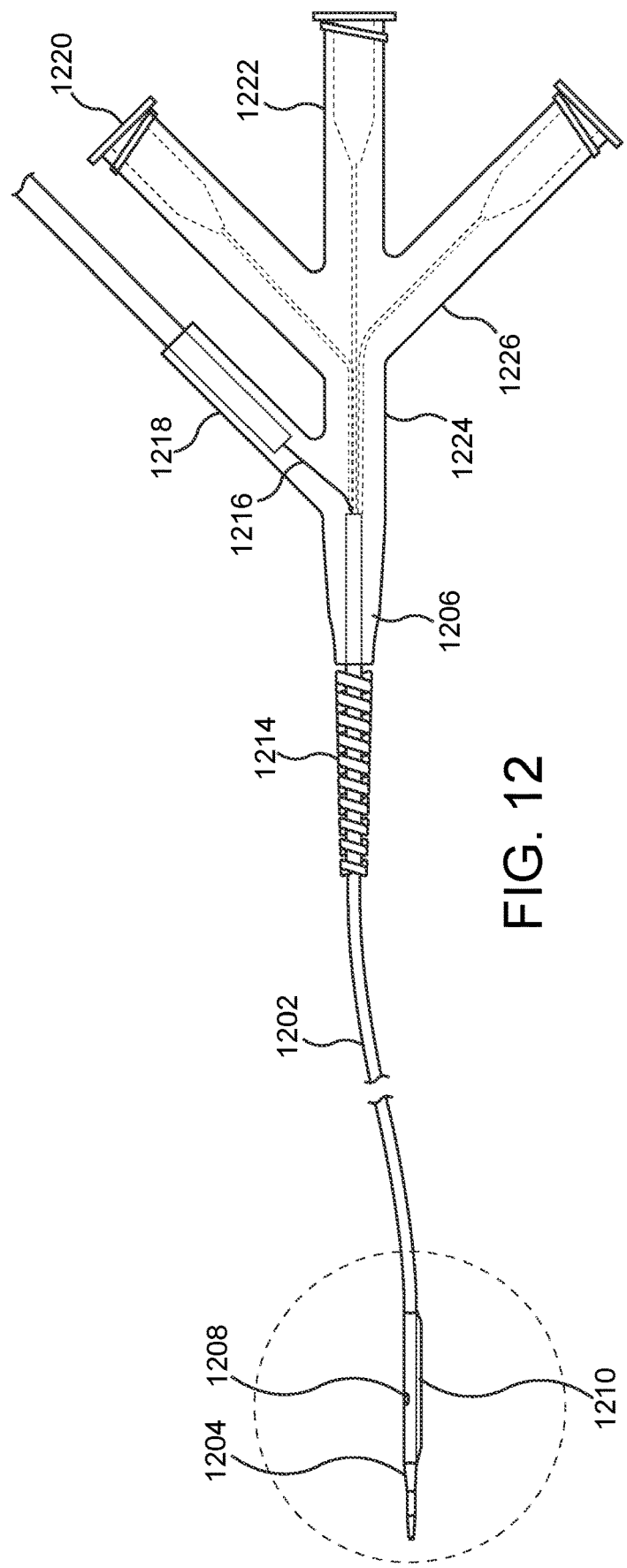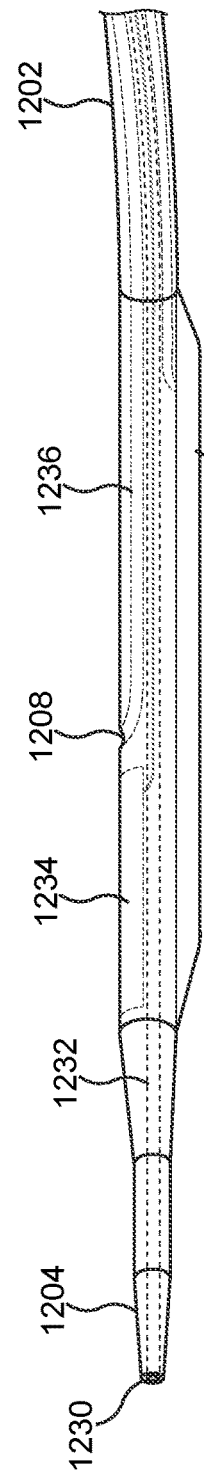
FIG. 12
FIG. 13

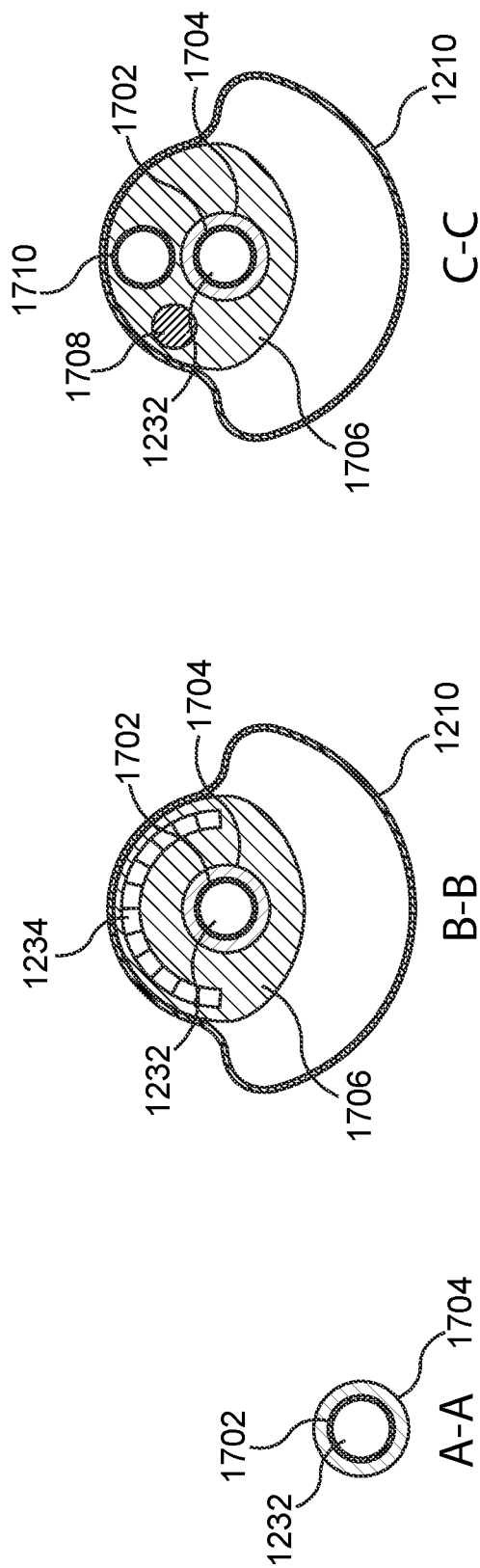
FIG. 17C  C-C
FIG. 17B  B-B
FIG. 17A  A-A
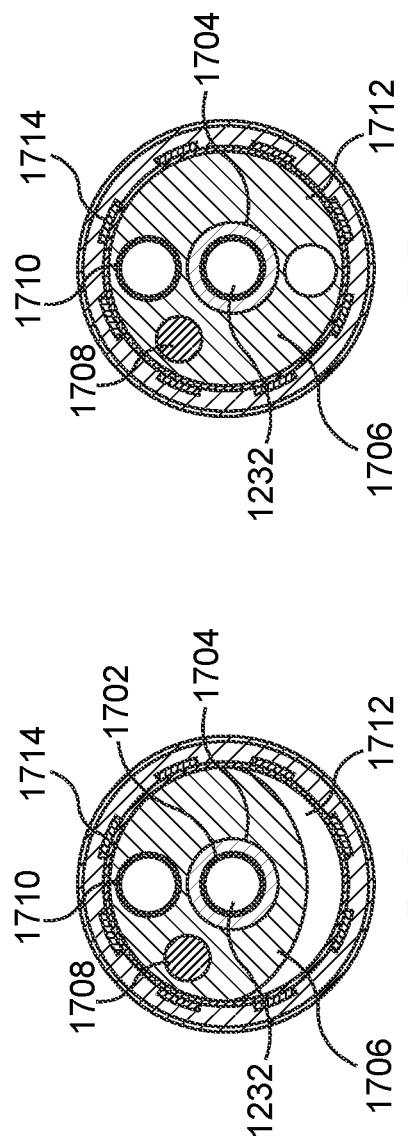
FIG. 17E  E-E
FIG. 17D  D-D

METHODS AND APPARATUS FOR TRUE LUMEN RE-ENTRY

CLAIM OF PRIORITY

This application claims the benefit of U.S. Patent Application No. 63/370,032, filed Aug. 1, 2022, titled "METHODS AND APPARATUS FOR TRUE LUMEN RE-ENTRY," which is herein incorporated by reference in its entirety.

BACKGROUND

There are roughly 100,000 percutaneous coronary interventions (PCI) performed every year in the US to treat chronic total occlusions (CTO) of coronary vessels, and roughly 300,000 such procedures worldwide. Even more CTO procedures are performed in the peripheral vessels. In coronary procedures, a guidewire is used to cross the obstruction and then the guidewire serves as a rail over which other diagnostic or therapeutic devices may be delivered to the treatment site. A guidewire successfully crosses the obstruction under fluoroscopic guidance in 40-50% of coronary CTO procedures. The remaining 50-60% fail, often due to extensive and long areas of occlusion. Sixty-three percent of the failure rate of antegrade wiring is related to subintimal or extra-plaque entry of the wire and/or other antegrade gear. Treatment often requires alternative techniques to cross the obstruction into the distal true lumen of the vessel. These techniques can be difficult to learn, challenging to safely perform, and time consuming.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 6A-6E show cross-sections taken along the longitudinal axis of the catheter of FIG. 5.

FIG. 10A shows a cross-sectional view of the basic anatomy of an occlusion in a blood vessel.

FIG. 10B shows a cross-section of FIG. 10A.

FIG. 12 shows another example of a catheter for introduction of a re-entry wire.

FIG. 13 highlights a distal portion of the catheter in FIG. 12.

FIGS. 17A-17E show various cross-sectionals taken along the length of the catheter in FIG. 16.

DETAILED DESCRIPTION

Figure 1:
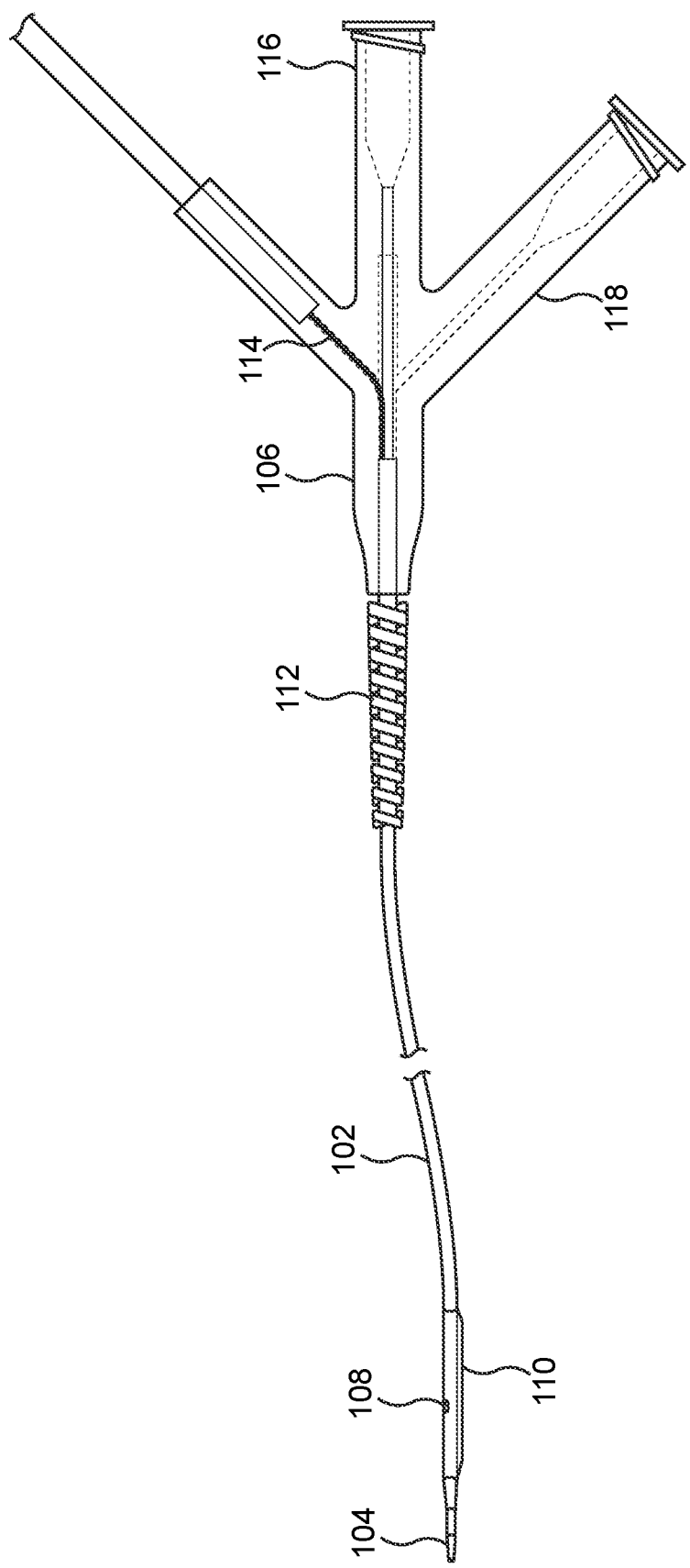
FIG. 1 shows an example of a catheter for introduction of a re-entry wire.

There has been an increasing interest in safe and more successful treatment of vascular chronic total occlusions (CTO). The treatment of CTO remains extremely challenging, with much higher risks and lower success rates compared to conventional, more standard percutaneous vascular revascularization. This is true in the coronary arteries as well in peripheral arteries (e.g., superficial femoral artery).

The most challenging CTO interventions involve revascularization of a long segment of occlusion. In the coronary arteries long lesions (e.g. longer than 2 cm) can rarely be treated with standard antegrade wiring techniques, and similarly in the periphery, long lesion (e.g. 5 to 10 cm or longer) can also be challenging to revascularize using wire antegrade or retrograde wiring techniques. A safe approach to open a long total occlusion is to use the ADR technique (antegrade dissection and re-entry) where the operator purposely tracks a guidewire and often a micro catheter, underneath the plaque (creating the dissection) to create a path that traverses the total occlusion. Once the path is created, the operator must re-enter the vessel true lumen distal of the occlusion to allow therapeutic devices such as angioplasty catheters or stents reopen and revascularize the vessel.

Some commercially available devices for re-entering the true lumen in antegrade dissection and re-entry require the operator to use angiographic guidance or blindly poke a stiff wire through the intima back into the true lumen using a catheter to deliver the wire. This may not result in a successful procedure due to the blind nature of the re-entry, where it is difficult to see the distal true lumen angiographically, in addition to the imprecise nature of the angiographic guidance, or calcium encasing the true lumen which also hinders visualization. Additionally, some commercially available devices do not maintain a predictable distance from the tip of the catheter to the reentry area (through the intima/plaque), and may depend on angiography to direct the reentry wire resulting in damage that the high contrast does to the patient and high failure rates, especially when the dissection creates a large subintimal space. Other devices can damage guidewires (e.g. damaging hydrophilic coatings). Other commercially available devices may include ultrasound and a curved hypo-needle to reenter the true lumen, which can make these devices stiff, have larger crossing profile, difficult to deliver, and unsuitable for smaller vascular beds. In addition the available devices are based on color flow doppler which is not reliable in many vascular territories. It would be desirable to provide improved re-entry devices.

Examples of a device and methods of use disclosed herein may address some of the challenges of currently available devices. In some examples, the success rate and safety of treating a CTO with a percutaneous coronary intervention may increase. Some examples may also be easier to learn and master than currently available technology. Complication rates such as vessel perforation, acute vessel closure, side branch loss and the need to rely on collateral vessels to open the CTO may be improved with the examples described herein.

Currently available devices and methods for treating CTO with PCI rely heavily on fluoroscopy and contrast based angiography to observe and control manipulation of a wire and microcatheter. Examples of a novel device disclosed herein may use an intravascular ultrasound (IVUS) guided catheter in order to revascularize chronic or acute vessel occlusions with wires under direct IVUS visualization. Other examples may use fluoroscopy, angiography, and still other examples may use ultrasound, or other imaging techniques known in the art.

Examples of the present device may use an IVUS array that emits an ultrasound beam that helps to visualize and direct a re-entry wire to a desired area (e.g. the thinnest and softest or least calcified part of the plaque) to optimize the chance for safe re-entry into the true lumen. Additionally, using IVUS allows the operator to visually confirm the entry of the re-entry wire into the true lumen thereby decreasing the risk of perforation and perpetuating the subintimal dissection.

The ultrasound beam in any example may allow visualization of a circumferential section of the vessel ranging from greater than 0 degrees up to 360 degrees, and in other examples from 10 to 180 degrees, or any other angle, and the device has a wire re-entry port that is oriented so that the re-entry wire exits the catheter so that it may be detected by the ultrasound beam and observed in the resulting ultrasound image. That way the operator can ensure that the re-entry wire safely and accurately re-enters the vessel true lumen from the subintimal space.

While the present disclosure focuses on the treatment of chronic total occlusions during percutaneous coronary interventions, this is not intended to be limiting and one of skill in the art will appreciate that the devices and methods described herein may be used to treat other obstructions or other conditions in the body including peripheral vessels such as the superficial femoral artery.

Re-Entry Device Example 1

FIG. 1 shows a first example of a catheter 102 that may be used to facilitate visualization, delivery, and re-entry of a re-entry wire when treating occlusions in a blood vessel such as a chronic total occlusion where the treatment catheter is unable to pass through the occlusion and therefore has to be delivered around the occlusion through the subintimal space. Here, the catheter 102 includes an elongate shaft having a proximal end 106 and a distal end 104. The distal end 104 has a re-entry port 108 where the re-entry wire exits the catheter and passes back from the subintimal space into the true lumen of the vessel, so that an angioplasty catheter or stent delivery catheter, or other diagnostic or therapeutic device may be delivered over a guidewire and across the occlusion. The distal-most end of the catheter may also include a distal port (best seen in FIG. 2) to allow a delivery guidewire to be slidably disposed through the catheter.

In some examples, an optional balloon 110 may also be included on the distal portion of the catheter and the balloon may be used to help anchor the distal end of the catheter and displace it away from the vessel wall radially inward to ensure that the re-entry port 108 is apposed to the region where re-entry is desired. The balloon may also be used to prevent blood from flowing past the balloon which can prevent formation of a hematoma. Additional disclosure related to the optional balloon is included later in this specification.

The proximal portion of the catheter may be coupled to a hub which contains connectors to allow the various cables and lumens in the catheter to be releasably coupled to other equipment. Here, a strain relief 112 helps prevent unwanted damage to the catheter shaft (e.g. unwanted kinking) at the point where it is coupled to the hub. The hub in this example includes one finger where the electrical cable 114 exits and is electrically coupled with an electrical connector that can be releasably or fixedly coupled to other electrical equipment such as an ultrasound imaging system or a source of electrical power. The electrical cable is coupled with an ultrasound transducer for imaging, as will be discussed in greater detail below. A second finger 116 on the hub may have a threaded Luer connector to allow it to be releasably or fixedly coupled to a fluid line, syringe, Indeflator or any other device. In this example, the middle connector 116 is fluidly coupled to a central lumen (best seen in FIG. 2) through which a delivery guidewire may be passed and that exits the distal-most port at the distal end of the catheter or through which a re-entry wire may be introduced and passed through the catheter and that exits the re-entry port 108. Thus, in this example, a single lumen shares a common proximal port and accommodates both a delivery guidewire (also referred to herein as a guidewire) and a re-entry wire, each having their own exit port. The third finger on the hub 118 may also be a threaded Luer connector to allow releasable or fixed coupling with an inflation device such as an Indeflator for inflating and deflating the optional balloon with a fluid such as saline, contrast media, a gas, or mixtures thereof such as a dilute mixture of contrast media formed from saline and contrast media. In the example where there is no balloon, the catheter would only have two fingers on the hub and the third finger 118 would be omitted. Additional details about the various aspects of this example will be discussed further below. One of skill in the art would also appreciate that a hemostasis valve (not shown) may be integrated into the various fingers of the hub or releasably coupled to the fingers as needed in order to prevent blood from leaking from the proximal end of the catheter. Examples of hemostasis valves may include duck bill valves, slit disc valves, or Tuohy-Borst valves.

Figure 2:
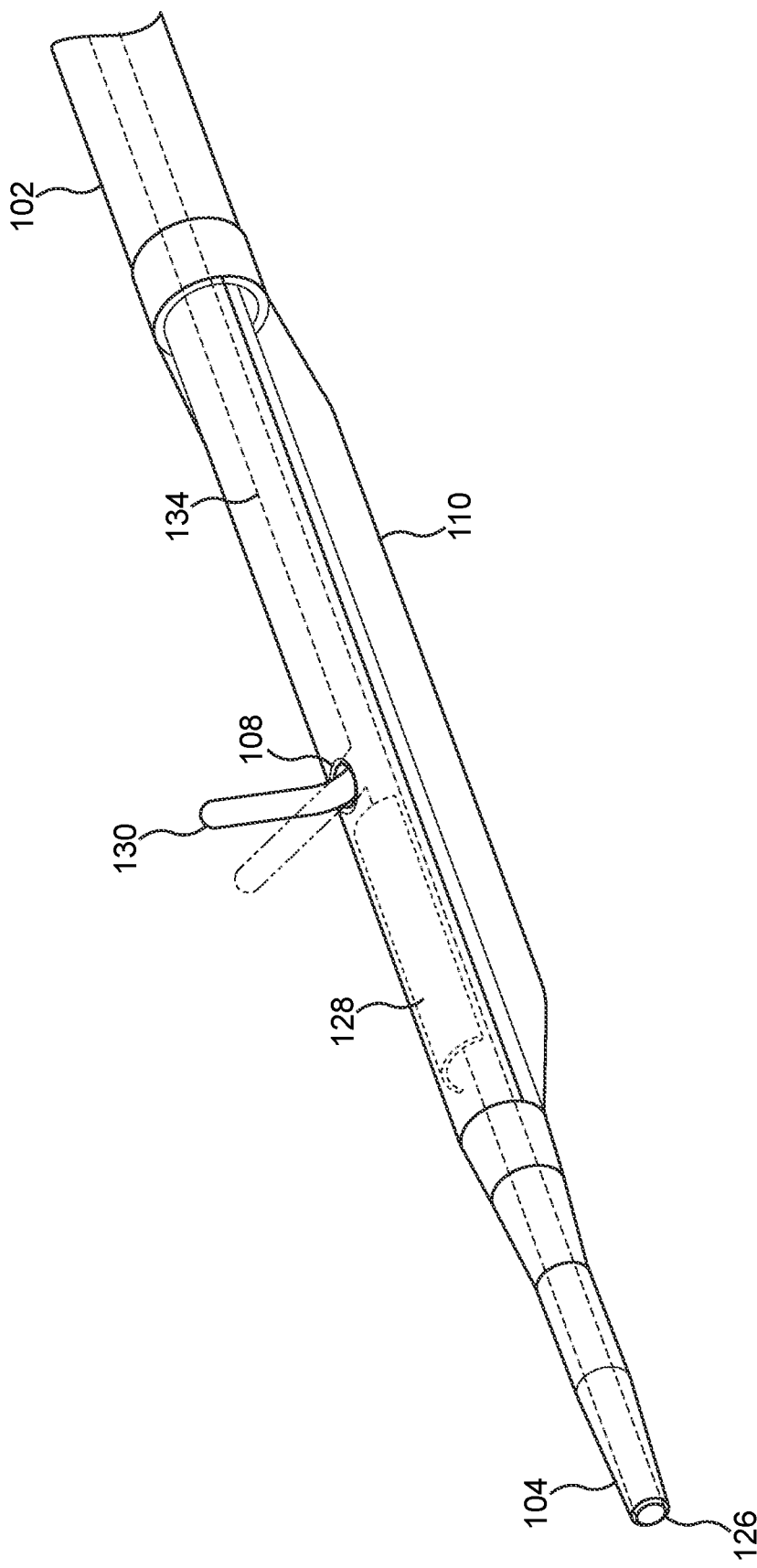
FIG. 2 shows a perspective view of a distal portion of the catheter in FIG. 1.

FIG. 2 shows the distal portion of catheter 102 in FIG. 1 in greater detail. In this view, the distal-most port 126 is seen and this port allows a guidewire to pass through central lumen 134 and to exit the catheter at the distal-most port 126 at the distal-most point of the catheter. An ultrasound transducer 128 is also visible in this view. The ultrasound transducer 128 may be a phased array or a partial phased array that is disposed fully or partially circumferentially around the catheter, or it may be a flat and planar transducer. A partial array provides a lower profile on the distal end of the catheter which does not take up as much space, and also allows a clear orientation view for the direction/location of the re-entry port/lumen, relative to the true lumen re-entry target. Optionally, a full array may be used that provides a 360 degree view of the vessel but will have a larger profile than the partial array. The ultrasound transducer elements in the array may each have the same shapes, lengths, and same concavity, or they have variable lengths, widths, and concavity. Longer ultrasound elements may make the catheter stiffer and can make it harder for the catheter track tortuous bends in the vessel but may provide a larger field of view. Concavity of the ultrasound elements will provide a wedge-shaped or arc shaped partial field image that facilitates a large far field of view with a smaller profile of ultrasound elements distributed over the catheter due to the diverging arc formed by the ultrasound beam as it moves radially outward and away from the transducer. A radiopaque marker (marker not shown) may be disposed adjacent the re-entry port to allow a user to see where the re-entry port is in use during imaging. In this example, the marker or markers are radiopaque but one of skill in the art will appreciate that the marker may be echogenic and visible with ultrasound, or a combination of radiopaque and ultrasound markers may be used, or any other marker that can be visualized using standard imaging techniques. This applies to this example, as well as any other example of a marker disclosed herein.

The ultrasound transducer allows an image of the vessel around the occlusion and adjacent the re-entry port to be obtained in order to allow a physician or operator to ensure that the re-entry wire 130 will re-enter the true lumen of the vessel at a desired position without causing trauma or otherwise damaging the vessel and surrounding tissue. For example, it may be desirable to re-enter the true lumen from the subintimal space at the thinnest and softest (e.g. least calcified) part of the obstructive plaque for a safe re-entry into the lumen. Also, the ultrasound transducer may allow the operator to observe advancement of the re-entry wire into the true lumen thereby permitting the operator to visually confirm that the re-entry wire is moving correctly through the true lumen and not propagating the dissection or perforating the vessel. Furthermore, the ultrasound transducer may allow visualization of the catheter when it is axially moved or torqued and rotated to ensure proper orientation of the catheter relative to the true lumen.

The ultrasound transducer may provide a beam that images a sector of any size, for example an arc of greater than 0 degrees up to 360 degrees, or greater than 0 degrees to 180 degrees, or 10 degrees to 160 degrees, or any range between 0 degrees and 360 degrees. The ultrasound transducer images the blood vessel and is emitted from the ultrasound transducer with an imaging axis that may be any angle relative to the longitudinal axis of the catheter such as 0 degrees to 180 degrees. For example, the ultrasound beam angle may be 90 degrees. An ultrasound imaging axis angle of 0 to less than 90 degrees is distally facing, while an angle of 90 degrees is perpendicular to the longitudinal axis of the catheter (or side firing), and an angle of greater than 90 degrees up to 180 degrees is proximally facing. Other examples of ultrasound angles include 0 degrees to 135 degrees. The ultrasound beam angle allows an ultrasound image to be obtained that not only shows the anatomy around the re-entry point of the vessel, but also shows the re-entry point where a re-entry wire exits the subintimal space and re-enters the vessel true lumen and shows the re-entry wire as it is advanced distally, thereby allowing the operator to observe the re-entry wire to ensure that it is properly advanced and does not puncture the vessel or propagate the dissection that was used to create the subintimal pocket. The re-entry wire 130 can exit the re-entry port at any angle, for example when the re-entry wire exits the re-entry port in a distally facing direction, the re-entry angle would be from 0 degrees to less than 90 degrees. If the re-entry wire exits perpendicular to the longitudinal axis of the catheter, then the re-entry wire would exit at a 90 degree angle relative to the longitudinal axis of the catheter. In some examples, the re-entry wire may exit the re-entry port facing proximally in which case the re-entry angle would be greater than 90 degrees up to 180 degrees. The ultrasound imaging axis is selected so that its angle cooperates with the re-entry angle and allows visualization of the re-entry wire. In some examples, the re-entry angle may be 30 degrees, 45 degrees, 60 degrees, or 90 degrees relative to the longitudinal axis of the catheter and the ultrasound imaging axis may be perpendicular (e.g. 90 degrees) or distally facing (e.g. 0 degrees to 90 degrees). These features of the ultrasound transducer may be used in this example or any of the examples of re-entry catheter disclosed herein that include an ultrasound transducer.

A re-entry wire 130 is shown passing through central lumen 134 and exiting the re-entry port. The re-entry wire may have a pre-shaped tip which can be rotated (torqued) to allow the direction of the re-entry wire tip to be adjusted as desired as indicated by the re-entry wire shown in phantom. In this example, the re-entry port is proximal of the proximal edge of the transducer 128 which ensures that the re-entry wire exits into a desired region of the true lumen of the vessel as seen in the image produced by the ultrasound transducer. In other examples, the re-entry port may be disposed in a different position relative to the ultrasound transducer. For example, re-entry port could be centered in the ultrasound transducer, or the re-entry port could be distal of the ultrasound transducer. Also, the optional expandable member, here a balloon 110 is shown disposed under the re-entry port 108 and in some examples the re-entry port may be disposed midway along the length of the balloon (re-entry port centered along the balloon), although this is not limiting and the balloon may be aligned in any desired orientation with the re-entry port 108. For example, the balloon could be proximal of the re-entry port or distal to the re-entry port, or straddling the re-entry port with the balloon or balloons disposed on both sides of the re-entry port. Having the balloon proximal to the re-entry port also may allow the balloon to be inflated and prevent blood flow into the pocket in which the re-entry catheter lies (the subintimal space) as well as helping to anchor the catheter. This may reduce the formation of a hematoma.

In any example disclosed herein, the balloon may be replaced by another expandable member such as a self-expanding wire basket or tines or any other mechanism that similarly pushes the re-entry port away from the vessel wall radially inward toward the re-entry position to ensure that the re-entry port is anchored and does not move, as well as ensuring that the re-entry port is apposed with the desired location for wire re-entry. In some examples the balloon or expandable member may be disposed 360 degrees circumferentially around the catheter shaft, or it may be partially disposed circumferentially around the catheter shaft. For example the balloon or expandable member may be disposed 180 degrees to 240 degrees circumferentially around the catheter. In another example, the balloon is disposed 180 degrees circumferentially around the catheter. The balloon or expandable member may be centered under the re-entry port, or it may be disposed off-center relative to the re-entry port and therefore may be axially proximal of or axially distal of the re-entry port with or without overlap of the expandable member and the axial position of the re-entry port.

Figure 3:
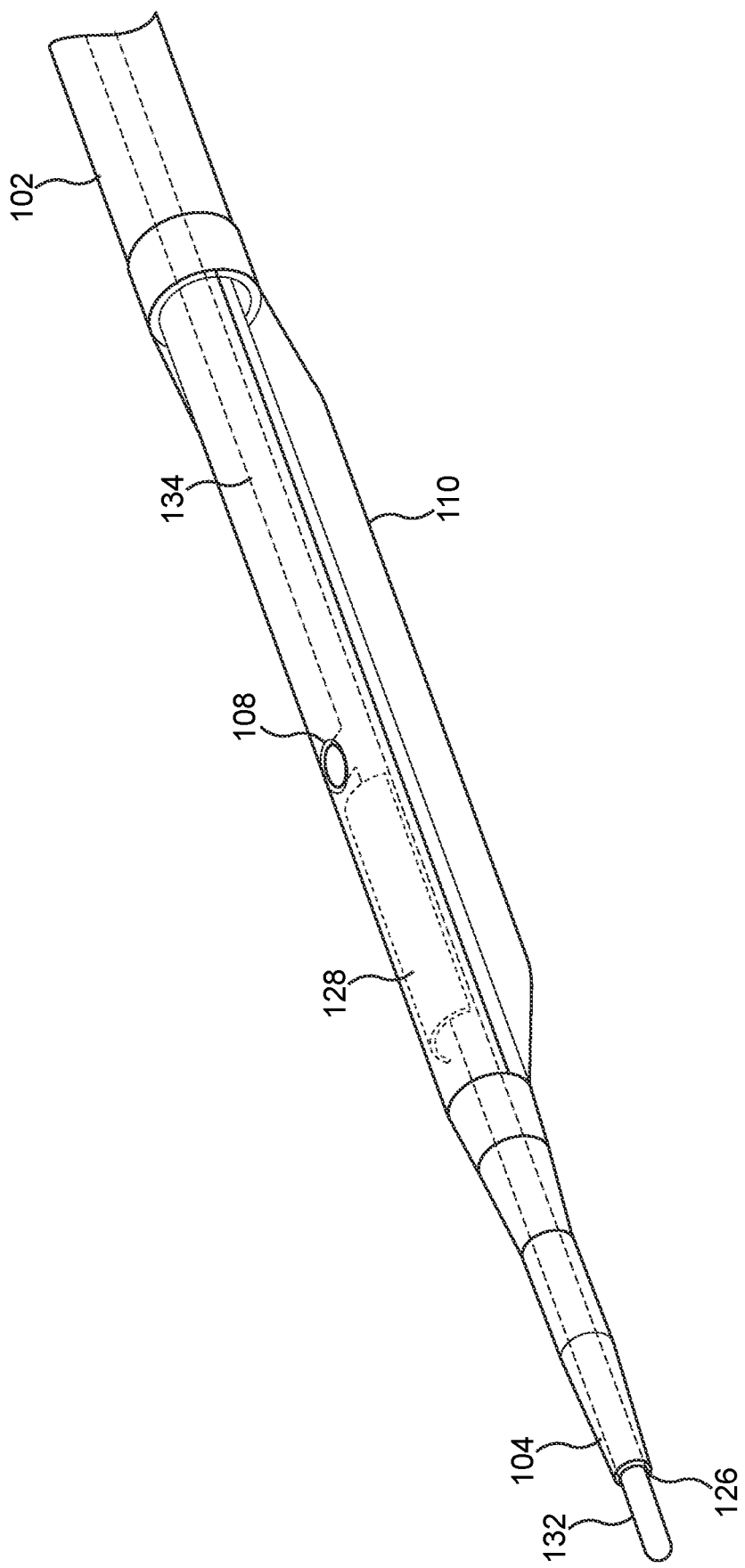
FIG. 3 shows another perspective view of a distal portion of the catheter in FIG. 1.

FIG. 3 shows a similar view of the distal portion of catheter 102 in FIG. 2 but this time with the re-entry wire removed and the guidewire 132 slidably disposed in the central lumen 134 of the catheter. Thus, the central lumen 134 may be used to deliver either the guidewire or the re-entry wire through the same lumen and out the respective port. The guidewire 132 is used to facilitate delivery of the catheter through the patient's vasculature to the target treatment region while the re-entry wire is used to help form a path through the subintimal space across the occlusion so that a therapeutic device such as an angioplasty catheter or a stent delivery catheter or a diagnostic device may be delivered across the occlusion. Further disclosure on the use of the two types of wires is discussed in greater detail below.

Figure 4:
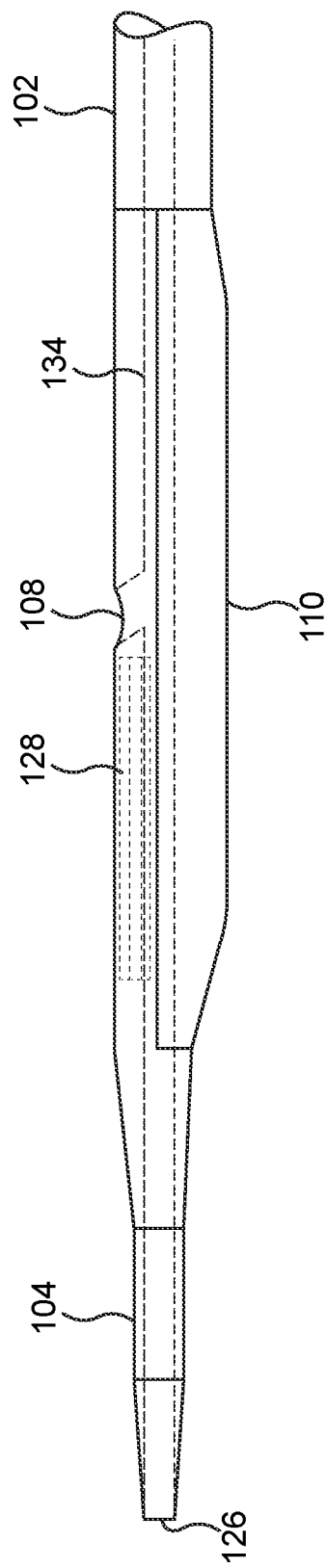
FIG. 4 shows a side view of a distal portion of the catheter in FIG. 1.

FIG. 4 is a side view of the distal portion of catheter 102 shown in FIGS. 2-3. Here, it is clear that central lumen 134 can be used to deliver a guidewire through the catheter and that exits distal port 126, or the central lumen 134 can be used to deliver a re-entry wire through the catheter and that exits re-entry port 108 since both the distal port 126 and the re-entry port 108 are fluidly connected with the central lumen 134. The ultrasound transducer 128 is also shown extending only partially circumferentially around the catheter.

Figure 5:
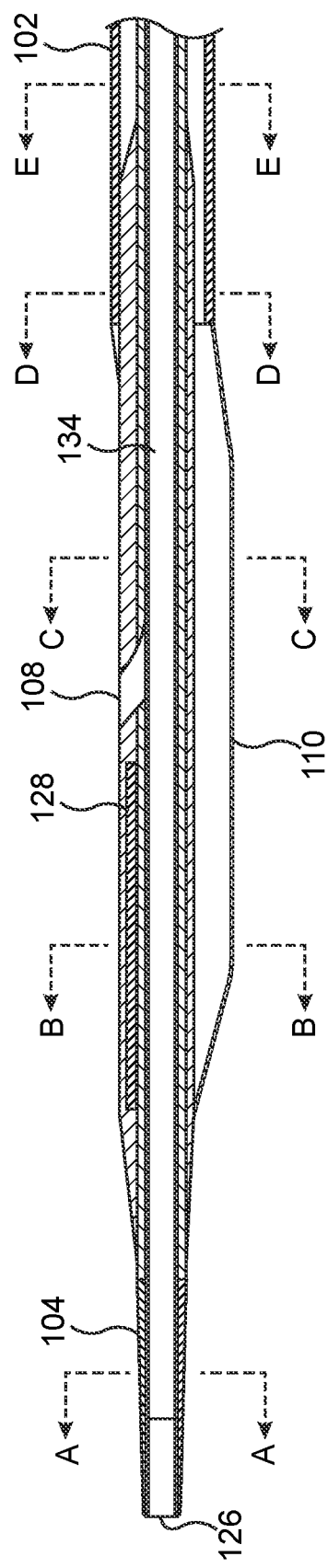
FIG. 5 shows a cross-section of the distal portion of the catheter in FIG. 1

FIG. 5 shows a cross-section of the side of distal portion of the catheter 102 shown in FIG. 1 above with various cross-sections taken along the longitudinal axis defined as sections A-A, B-B, C-C, D-D and E-E. FIG. 5 shows that the central lumen may be formed from a separate tube that is disposed in, and coupled to the catheter shaft which creates an annular space between the two tubes. The annular space may be used as an inflation lumen for inflating or deflating the optional balloon 110. In other examples, the lumens may be integrally formed by co-extrusion or other manufacturing techniques known in the art to form a single or multi-lumen tube. The distal end of the catheter may include a tapered distal tip to prevent trauma to the vessel as well as to facilitate introduction and delivery of the catheter through the vasculature.

FIGS. 6A-6E show various cross-sections taken along the longitudinal axis of the distal portion of catheter 102 shown previously in FIG. 5.

FIG. 6A shows the cross-section taken along line A-A in FIG. 5. Here the central lumen 134 is shown formed by an inner tube 604 (e.g. a microliner which may be used in any lumen in any of the examples disclosed herein) surrounded by an outer tube 602 which forms the outer portion of the catheter which includes a tapered distal tip.

FIG. 6B shows the cross-section taken along line B-B in FIG. 5. This includes the features previously discussed in FIG. 6A as well as the expandable member 110, here a balloon and the ultrasound transducer 128. In this example, the balloon only partially expands circumferentially around the catheter shaft (asymmetrical expansion) so that when expanded, the balloon will displace the distal portion of the catheter radially inward away from the vessel wall toward the vessel true lumen and anchor the catheter. The expanded balloon also helps to ensure that the catheter position is maintained once the re-entry port is aligned with a desired re-entry position in the vessel after confirmation with imaging provided by the ultrasound transducer. Also, as previously mentioned, the inflated balloon may help prevent blood from filling the subintimal space and creating a hematoma that can compress the true lumen. In this example, the balloon is axially centered relative to the ultrasound transducer and the ultrasound transducer is distal of the re-entry port. In other examples, balloon position may be different, for example the balloon may be proximal to, or distal of the re-entry port. In other examples the balloon may have different configurations such as a balloon that circumferentially expands fully around the catheter so as to center the catheter distal portion in the vessel (if desired). Additional material 608 such as a polymer or adhesives may be disposed in the spaces between components to ensure that they are held together and fluid channels are properly formed without fluid leaks. As previously discussed, the ultrasound transducer may be a phased array that is partially disposed around the catheter to provide a partial view of the vessel being treated, or it may be fully disposed around the catheter if a full 360 degree image of the vessel is desired. In still other examples, the ultrasound transducer may be a flat planar transducer coupled to the catheter. In the configuration where the transducer is only partially disposed circumferentially around the catheter, the catheter may be torqued to rotate the catheter to view other portions of the vessel that are outside of field of view provided by the transducer. In other examples, the ultrasound transducer may be a rotational ultrasound transducer, with or without a barrier, where the ultrasound transducer is coupled to a rotating shaft disposed in a separate lumen in the catheter to provide a partial view or full 360 degree view of the vessel. This example may use an ultrasound blocking material opposite the re-entry wire exit port and an optional echogenic marker opposite the re-entry port so the operator knows where the position of the re-entry port in the ultrasound image. Other aspects of the transducer were previously disclosed above. In this manner the re-entry port can be aligned ideally, using real-time IVUS images, at the optimal site to cross through the plaque at a place of relatively thin and non-calcified plaque in order to increase the chances of re-entry into the true lumen of the blood vessel while avoiding causing trauma or other damage to the vessel or adjacent tissue.

FIG. 6C shows the cross-section taken along the line C-C in FIG. 5 above. Here, the same features of FIG. 6B are shown except without the ultrasound transducer. Additionally, electric cable 610 is shown. This cable is coupled to the ultrasound transducer to provide power to the transducer 128 and to deliver the signal captured by the transducer back to the proximal end of the catheter where an electrical connector may be used to couple the catheter to other electronics for processing and viewing the resulting ultrasound image. The electric cable 610 may be disposed in a separate lumen in the catheter or the catheter may be formed by coextruding the catheter shaft with the electric cable. The electric cable may include one or more wires.

FIG. 6D shows the cross-section taken along the line D-D in FIG. 5 above. Here the same features of FIG. 6A are shown along with an optional balloon inflation lumen 614 (when there is a balloon) and optional braiding 612. Here, the optional inflation lumen is crescent shaped and formed by the annular space 614 between the inner lumen tube 604 and the outer tube 616 of the catheter. This lumen may be used to deliver a fluid such as saline, contrast media, mixtures thereof (e.g. dilute contrast media), or a gas to inflate the balloon, and to remove the inflation fluid to deflate the balloon. The inflation lumen is fluidly coupled to the proximal hub and port as previously discussed with respect to FIG. 1. Optional braiding material 612 may be included in the catheter shaft in order to give the catheter shaft desired material properties such as pushability, torquability, kink resistance, etc. The catheter shafts in this example as well as any example may be fabricated from materials known in the art such as nylon, polyethylene, PTFE, Pebax, vinyl, etc.

FIG. 6E shows the cross-section taken along the line E-E in FIG. 5 above. It includes the features of FIG. 6A and some of the features of FIG. 6D. The lumen 614 is enlarged from the crescent shape in FIG. 6D to a full annular ring.

Figure 7A:
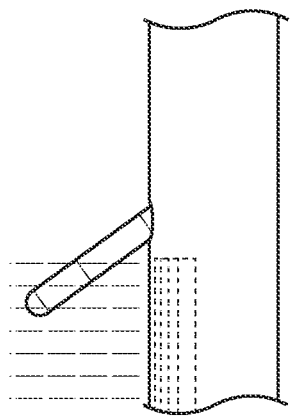
FIG. 7A shows a side view of FIG. 7.
Figure 7B:
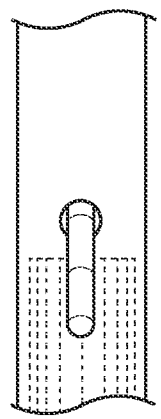
FIG. 7B shows a top-down view of the FIG. 7.
Figure 7:
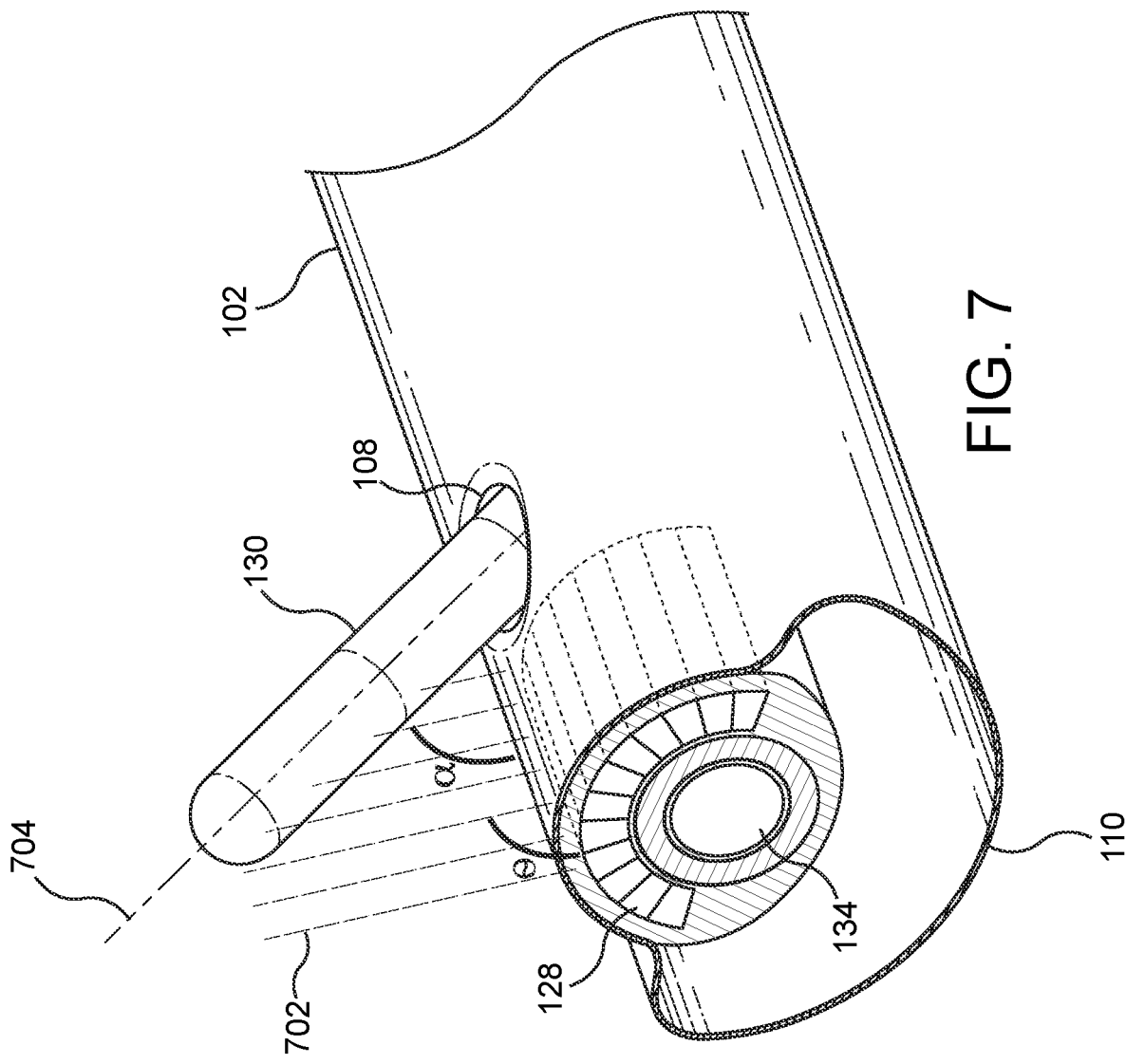
FIG. 7 shows a perspective view of a distal portion of the catheter of FIG. 1 with the re-entry wire exiting the catheter and intersecting the ultrasound beam.

FIG. 7 shows a partial perspective view of a distal portion of the catheter shown in FIGS. 1-6E above. Here, the cross-section of FIG. 7 taken at the distal end of the figure would be the same as previously shown in FIG. 6B. Here, the re-entry wire 130 exits the re-entry wire port 108 along a re-entry axis 704 that forms an angle alpha with the longitudinal axis of the catheter, and the angle faces distally. Additionally, the ultrasound transducer emits an ultrasound beam 702 that also forms an angle theta with the longitudinal axis of the catheter thereby forming an image of the vessel. The desired re-entry position is ideally where the plaque is the thinnest and least calcified, and where the true lumen has the largest cross-sectional area. The ultrasound image also allows the operator to observe the re-entry port and re-entry wire as it exits the re-entry port to ensure that that re-entry wire enters the true lumen in the desired position.

In this example, the ultrasound transducer may provide a beam that images a sector of any size, for example an arc of greater than 0 degrees up to 360 degrees, or greater than 0 degrees to 180 degrees, or 10 degrees to 180 degrees, or any range between 0 degrees and 360 degrees. The ultrasound transducer images the blood vessel and has an imaging axis that may be any angle relative to the longitudinal axis of the catheter such as 0 degrees to 180 degrees. For example, the angle theta may be 90 degrees. An ultrasound imaging axis angle theta of 0 to less than 90 degrees is distally facing, while an angle theta of 90 degrees is perpendicular to the longitudinal axis of the catheter (or side firing), and an angle theta of greater than 90 degrees up to 180 degrees is proximally facing. In another example, theta is between 0 degrees and 135 degrees. The ultrasound beam angle allows an ultrasound image to be obtained that not only shows the anatomy around the re-entry point of the vessel, but also shows the re-entry point where a re-entry wire exits the subintimal space and re-enters the vessel true lumen and shows the re-entry wire as it is advanced distally, thereby allowing the operator to observe the re-entry wire to ensure that it is properly advanced and does not puncture the vessel or propagate the dissection that was used to create the subintimal pocket.

The re-entry wire 130 can exit the re-entry port at any angle alpha, for example when the re-entry wire exits the re-entry port in a distally facing direction, the re-entry angle alpha would be from 0 degrees to less than 90 degrees. If the re-entry wire exits perpendicular to the longitudinal axis of the catheter, then the re-entry wire would exit at a 90 degree angle (angle alpha) relative to the longitudinal axis of the catheter. In some examples, the re-entry wire may exit the re-entry port facing proximally in which case the re-entry angle alpha would be greater than 90 degrees up to 180 degrees.

The ultrasound imaging axis is selected so that its angle (theta) cooperates with the re-entry angle (alpha) and allows visualization of the re-entry wire. In some examples, the re-entry angle may be 30 degrees, 45 degrees, 60 degrees, or 90 degrees relative to the longitudinal axis of the catheter and the ultrasound imaging axis may be perpendicular (e.g. 90 degrees) or distally facing (e.g. 0 degrees to 90 degrees). In other examples, the ultrasound beam angle theta may be from 0 degrees to 135 degrees. These features of the ultrasound transducer may be used in this example or any of the examples of re-entry catheter disclosed herein that include an ultrasound transducer.

FIG. 7A shows a side view of the example in FIG. 7 and illustrates in this example that the re-entry wire 130 exits the re-entry port 108 at an angle (here, distally facing) such that the re-entry wire is captured in the ultrasound beam 702 which is emitted from ultrasound transducer 128. This ensures that the re-entry wire can be observed in the resulting ultrasound image so that the operator can observe the re-entry wire as is it re-enters the true lumen and is advanced distally in the true lumen. In this example, the ultrasound beam 702 is emitted orthogonally relative to the ultrasound transducer.

FIG. 7B shows a top view of the example in FIGS. 7 and 7A.

Examples of Hubs

Figure 8:
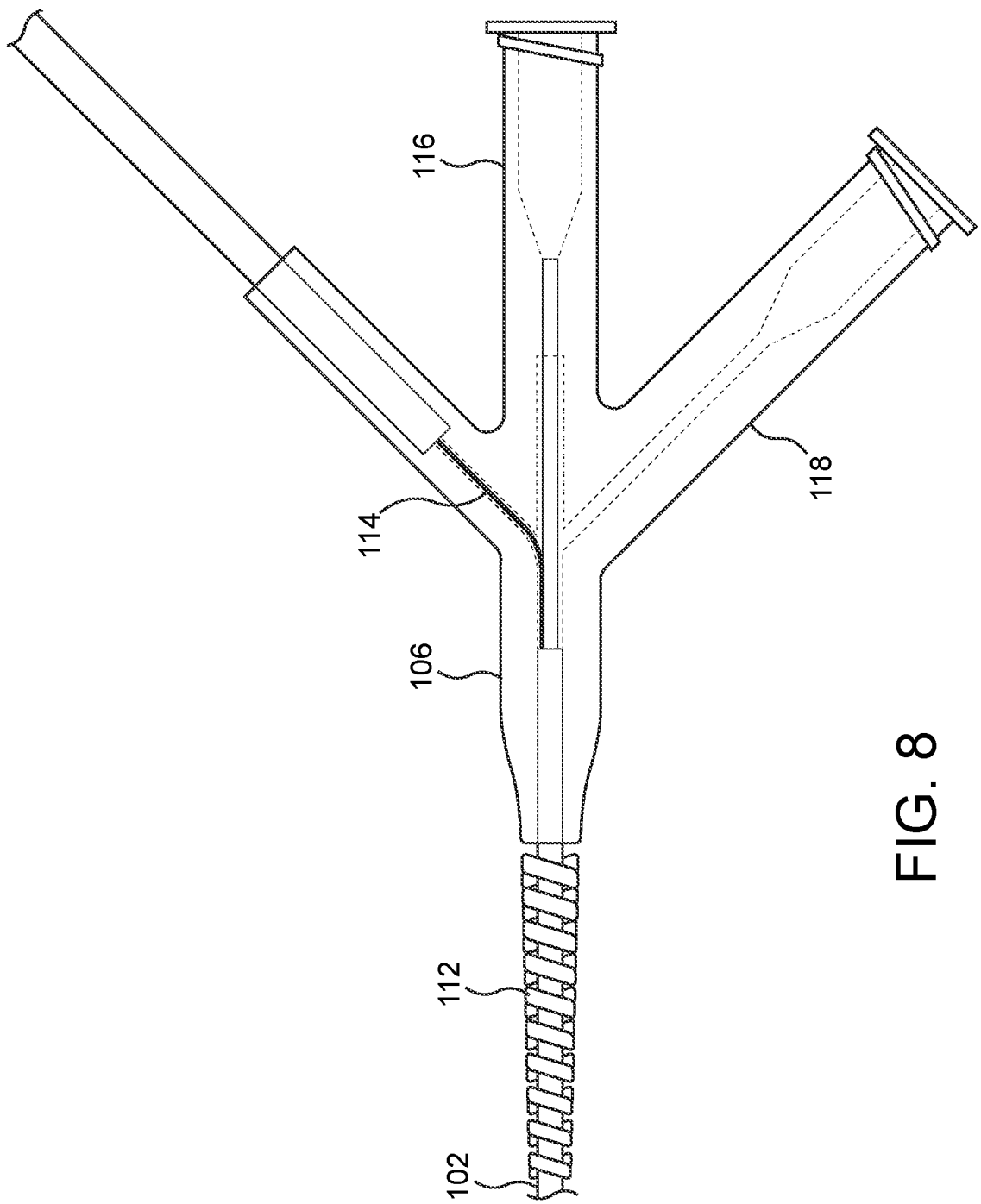
FIG. 8 shows an example of a hub on the proximal end of the catheter of FIG. 1.

FIG. 8 shows an example of a proximal end 106 of the catheter 102 of FIG. 1 highlighting the hub. Here, the catheter includes an optional balloon and therefore has a balloon inflation lumen as well as a shared lumen for the guidewire and the re-entry wire.

A strain relief 112 helps prevent unwanted damage to the catheter shaft (e.g. kinking) at the point where it is coupled to the hub due to bending, torquing, etc. The hub in this example includes one finger where the electrical cable 114 exits and can be coupled with a connector to other electrical equipment such as an ultrasound imaging system. The electrical cable is coupled distally with an ultrasound transducer for imaging, as previously discussed. A second finger 116 on the hub may have a threaded Luer connector to allow it to be releasably coupled to a syringe, Indeflator or any other device. In this example, the middle connector 116 is fluidly coupled to a central lumen through which a guidewire may be passed and that exits the distal-most port at the distal end of the catheter or through which a re-entry wire may be introduced and passed through the catheter and that exits the re-entry port 108. Thus, in this example, a single lumen accommodates both a guidewire and a re-entry wire. The third finger on the hub 118 may also be a threaded Luer connector to allow releasable coupling with an inflation device such as an Indeflator for inflating and deflating the optional balloon with a fluid such as saline, contrast media, a gas, or mixtures thereof (e.g. dilute contrast media). In the example where there is no balloon, the catheter would only have two fingers on the hub and the third finger 118 would be omitted as will be illustrated in FIG. 9 below.

Figure 9:
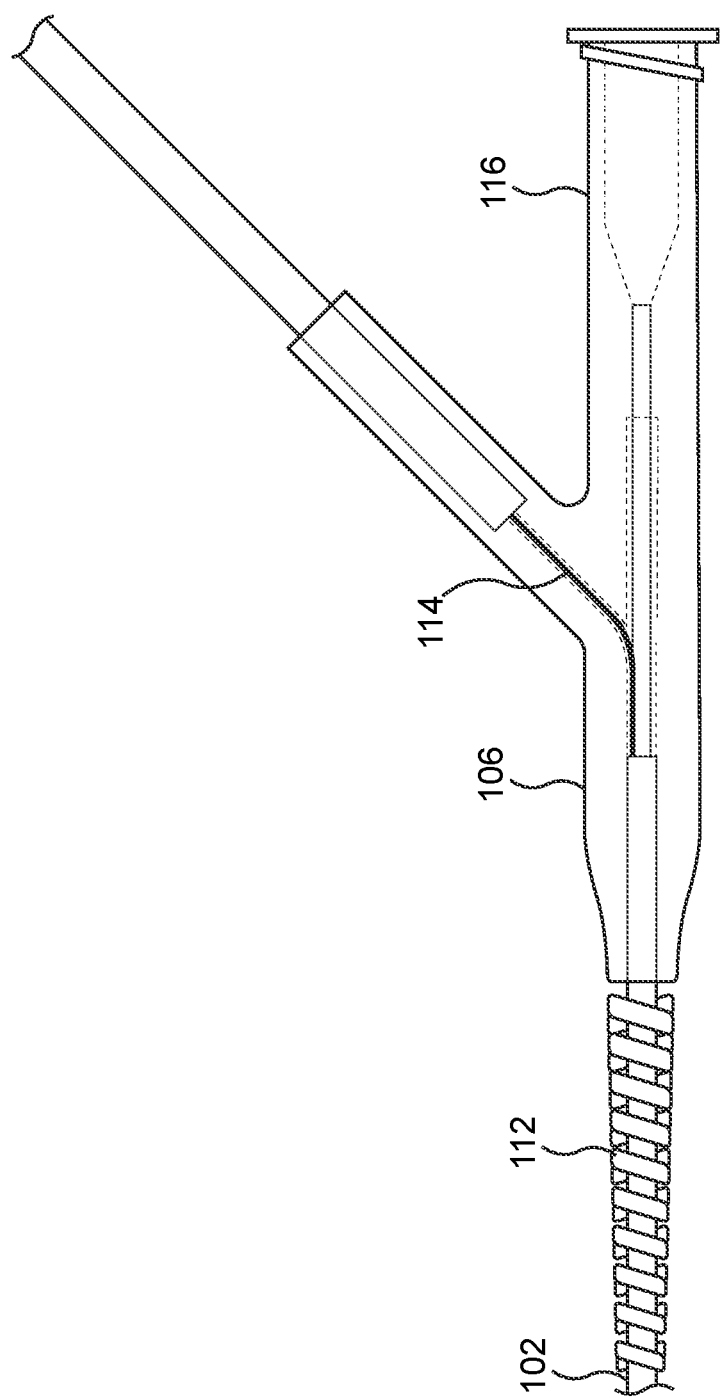
FIG. 9 illustrates another example of a hub on the proximal end of the catheter of FIG. 1.

FIG. 9 shows an example of a proximal end 106 of the catheter 102 of FIG. 1 highlighting the hub. Here, the catheter does not include the optional balloon and therefore does not have an inflation lumen so the hub has one less finger than the example in FIG. 8. There is only one lumen and that is a shared lumen for the guidewire and the re-entry wire. Other aspects of the hub are generally the same as previously described with respect to FIG. 8.

A strain relief 112 helps prevent unwanted damage to the catheter shaft at the point where it is coupled to the hub (e.g. kinking). The hub in this example includes one finger where the electrical cable 114 exits and can be proximally and releasably coupled to other electrical equipment such as an ultrasound imaging system. The electrical cable is distally coupled with an ultrasound transducer for imaging, as previously discussed. A second finger 116 on the hub may have a threaded Luer connector to allow it to be releasably coupled to a syringe, Indeflator or any other device. In this example, the connector 116 is fluidly coupled to a central lumen through which a guidewire may be passed and that exits the distal-most port at the distal end of the catheter or through which a re-entry wire may be introduced and passed through the catheter and that exits the re-entry port. Thus, in this example, a single lumen accommodates both a guidewire and a re-entry wire.

The examples shown above in FIGS. 1-9 have a single common lumen for both the guidewire and the re-entry wire. The guidewire has a distal exit port at the distal-most end of the catheter and the re-entry wire has a re-entry wire port on a distal portion of the catheter and proximal of the distal exit port. The proximal port that is fluidly coupled with the common lumen was shown as being disposed at the proximal end of the catheter and coupled to a connector hub. This configuration is referred to as an over the wire (OTW) configuration where the proximal port is closer to the proximal end of the catheter than the distal exit port or the re-entry port. However, in other examples the port configurations may be arranged in a rapid exchange configuration where the proximal port is disposed closer to the distal port or re-entry port than the proximal end of the catheter. This example will be described in greater detail later in this specification.

FIG. 10A shows the basic anatomy of an occlusion in a blood vessel that may be treated using any of the examples of catheters disclosed herein. Here, a blood vessel V such as an artery like a coronary artery of the heart has an occlusion or blockage B (also referred to herein as an obstructive plaque or stenotic lesion) that prevents blood flowing from the proximal end of the vessel to the distal end of the vessel thereby causing inadequate oxygenation or ischemia to tissues supplied by the vessel. In some situations the blockage B may be heavily calcified and extremely hard and therefore it can be extremely difficult or impossible to pass a guidewire through the blockage and this in turn prevents a balloon angioplasty or stent delivery catheter from being delivered to the treatment region for treatment of the blockage. In some situations, the blockage completely occludes the vessel and this condition may be referred to as a chronic total occlusion (CTO).

FIG. 10B shows a cross-section of the vessel taken along the line A-A in FIG. 10A and shows the vessel V formed of three layers of tissue including the outer-most tissue layer known as the adventitia, the middle layer referred to as the media, and the inner-most layer known as the intima. The blockage, referred to as a plaque which may be a calcified layer rests against the internal elastic lamina and represents a thickened intima. The true lumen is the natural lumen of the blood vessel that is substantially unobstructed by the plaque.

Because the plaque totally occludes the vessel and may be heavily calcified and difficult or impossible to pass a guidewire through, physicians may use a procedure where a guidewire is advanced distally through the true lumen of the vessel up until the blockage. The guidewire is then purposely or inadvertently advanced subintimally distally (antegrade direction) in the region between the intima and the plaque (dissection) and past the blockage to a region distal of the occlusion where the guidewire can then be redirected back into the true lumen (re-entry). Hence the acronym ADR which refers to antegrade dissection and re-entry. Once the wire is in position within the distal true lumen, therapeutic devices such as an angioplasty catheter or stent delivery system may be advanced over the wire. The challenge with this method is that an operator does not always know whether the re-entry wire will correctly re-enter into the true lumen of the vessel. Improper wire re-entry can result in damage to the vessel wall, or perforation of the vessel, or the wire can merely propagate in the subintimal space, extending the dissection. Using the catheter example described above in FIGS. 1-9 will allow a physician or operator to visualize where the guidewire will re-enter the vessel and ensure, and confirm visually, that it re-enters in a desired position and is advanced properly through the true lumen. The guidewire that re-enters the true lumen may be referred to herein as a re-entry wire.

Example of Method of Use

Figure 11A:
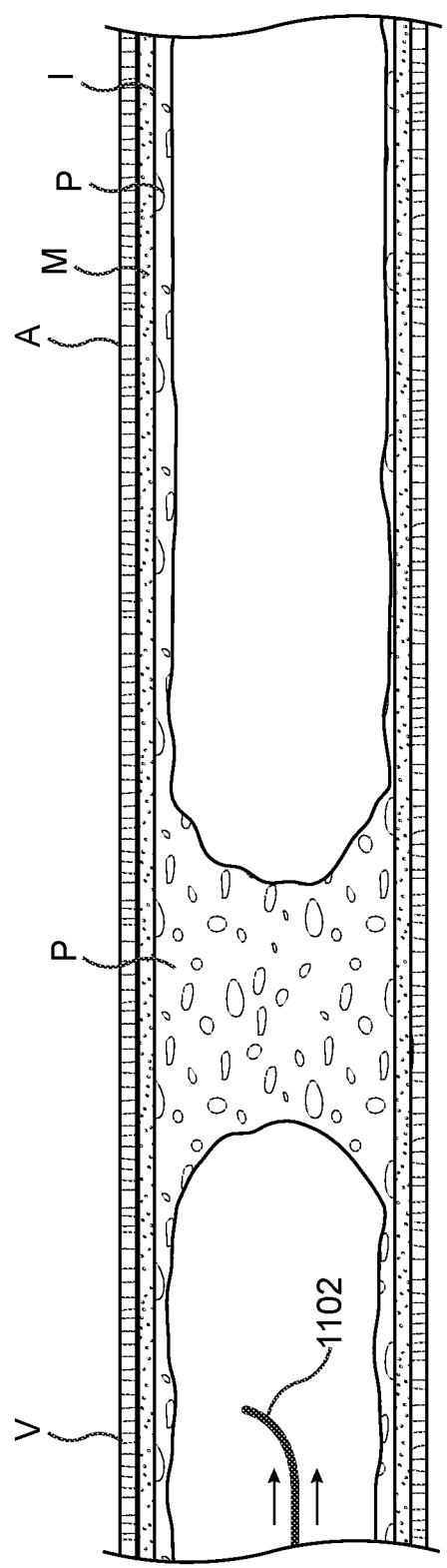
FIGS. 11A-11AR show an example of a method of treating an obstruction in a vessel.

FIGS. 11A-11AR illustrate an example of a method of using the catheter described previously in FIGS. 1-9 above to treat an occlusion in a vessel such as a chronic total occlusion in a coronary artery. This is not intended to be limiting and the catheter may be used to treat other occlusions, other vessels, or other conditions in a patient.

In FIG. 11A, an obstructive plaque P forms a chronic total occlusion (CTO) in the vessel V which includes the outer adventitia A tissue layer, followed by middle tissue layer media, M, and inner-most tissue layer intima, I. In this specification, the obstructive plaque P refers to the occlusion (e.g. blockage) even though one of skill in the art will appreciate that the actual plaque may extend proximally and distally of the occlusion as seen in FIG. 11A, but this may be a thinner layer of plaque that does not occlude the vessel or hinder the use of guidewires, or treatment devices. A physician or operator may introduce a workhorse guidewire percutaneously such as with the Seldinger procedure or via cutdown at any desired point in the vascular system (e.g. femoral artery, radial artery, brachial artery, etc.) and advance the workhorse guidewire 1102 distally toward the obstructive plaque P. The guidewire 1102 may be a straight tip or have a pre-shaped curved tip, as desired by the operator.

Figure 11B:
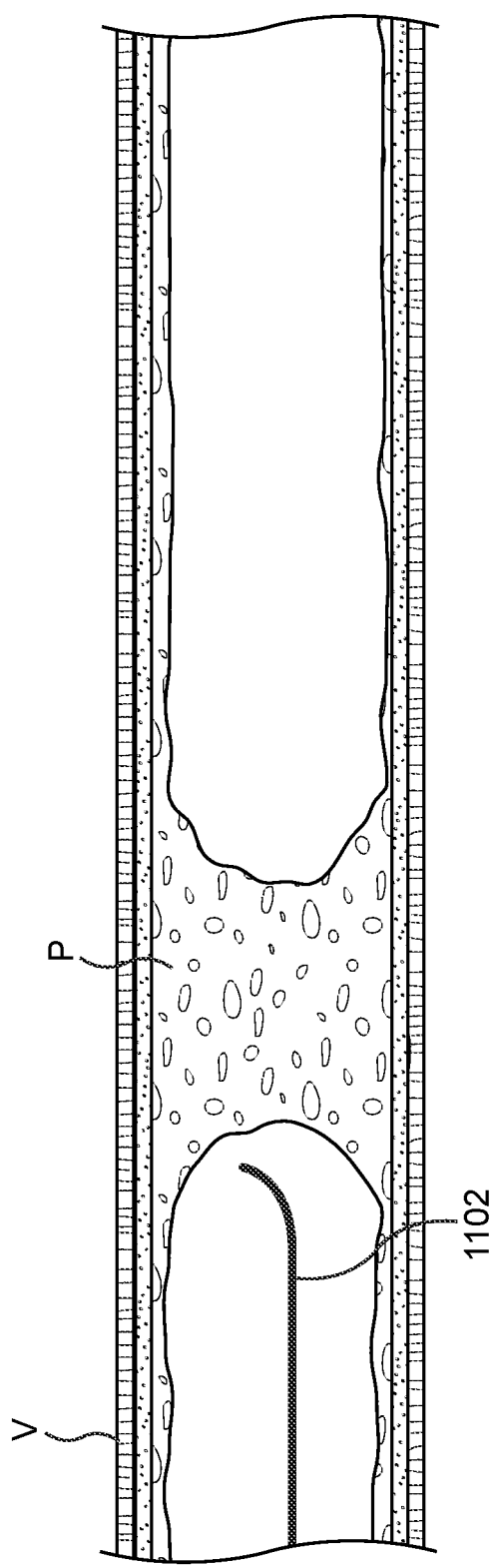

In FIG. 11B, the workhorse wire 1102 is advanced further distally until it is in a desired position adjacent the proximal portion of the obstructive plaque P. Position of the guidewire may be confirmed based on a fluoroscopic image, ultrasound, tactile feel of the wire, or other techniques known in the art.

Figure 11C:
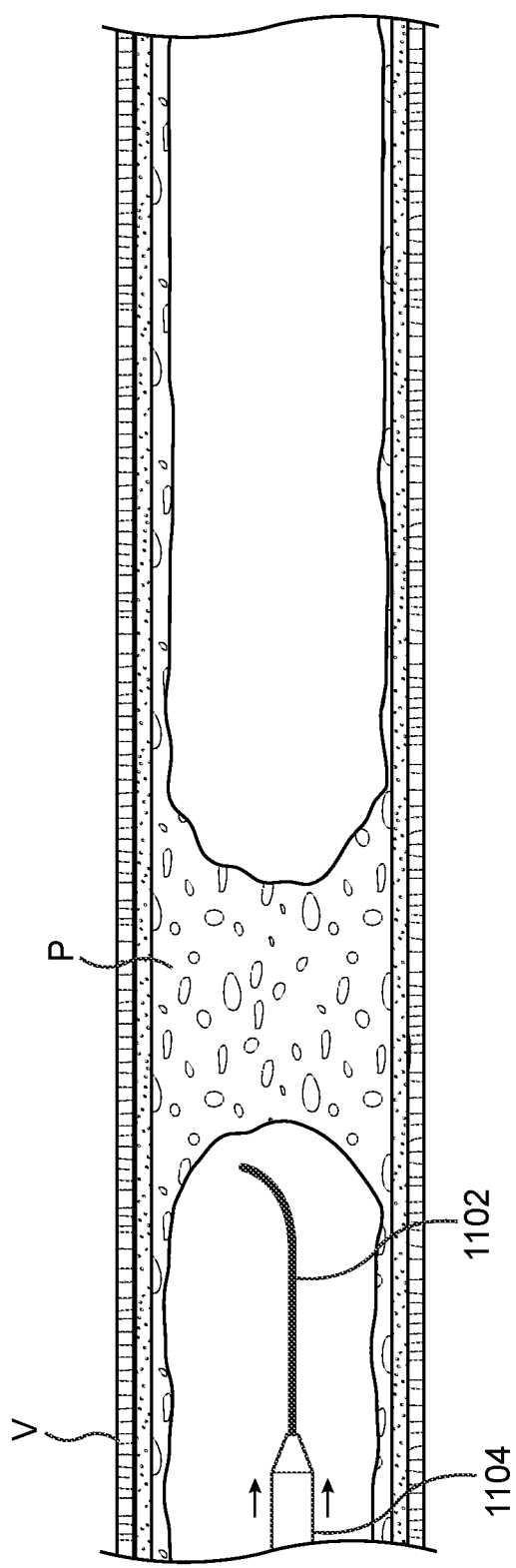

FIG. 11C shows that after the workhorse guidewire 1102 is properly positioned, a microcatheter, sheath, or other wire exchange catheter 1104 is advanced over the workhorse guidewire 1102 toward the obstructive plaque P.

Figure 11D:
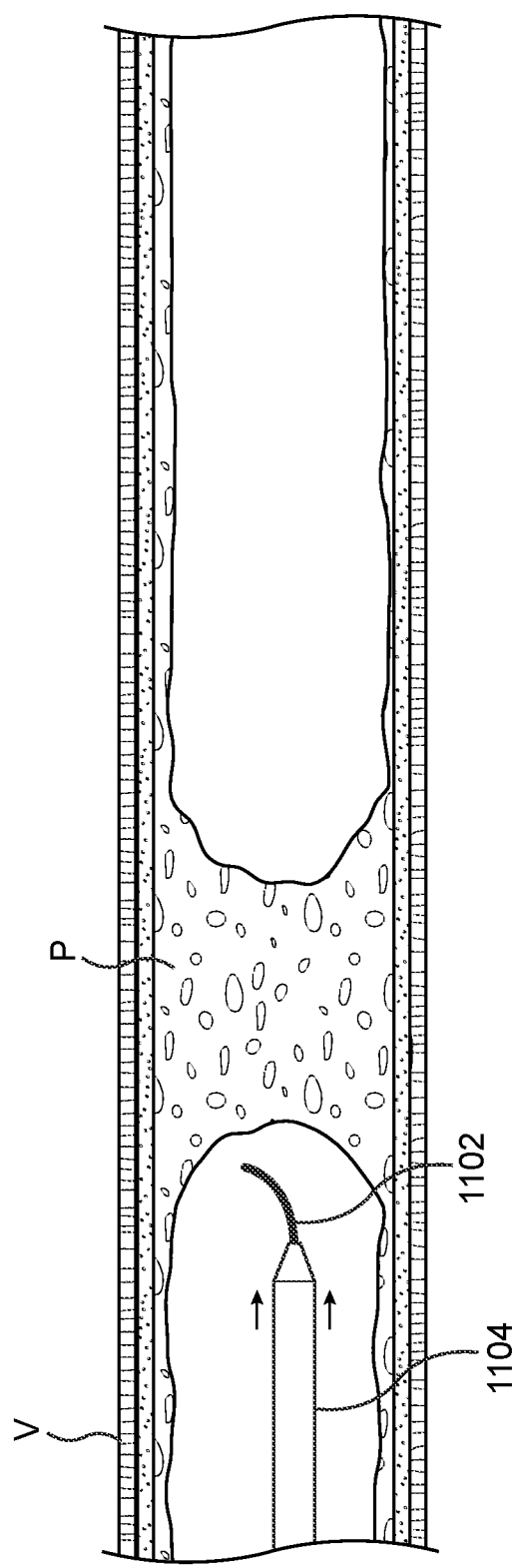

In FIG. 11D the microcatheter, sheath or other wire exchange catheter 1104 is further advanced distally until it is adjacent the obstructive plaque P.

Figure 11E:
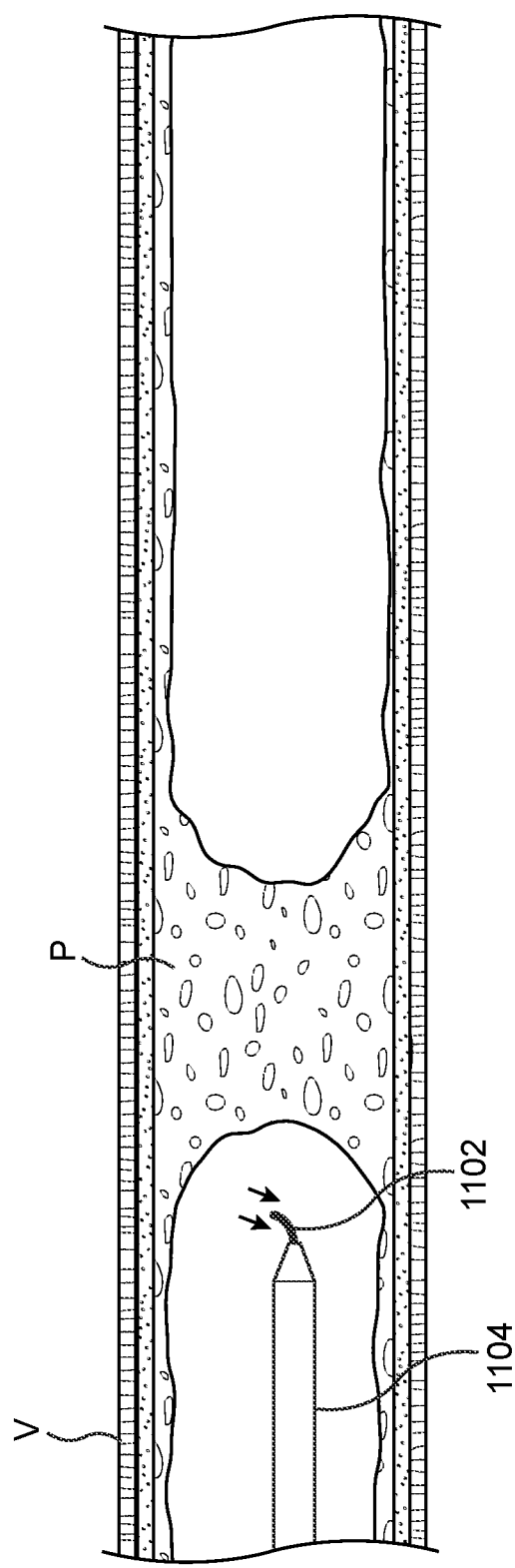

After the microcatheter, sheath or other wire exchange catheter 1104 has been advanced distally to be adjacent the obstructive plaque P and is in a desired position, the workhorse guidewire 1102 may be retracted proximally as seen in FIG. 11E.

Figure 11F:
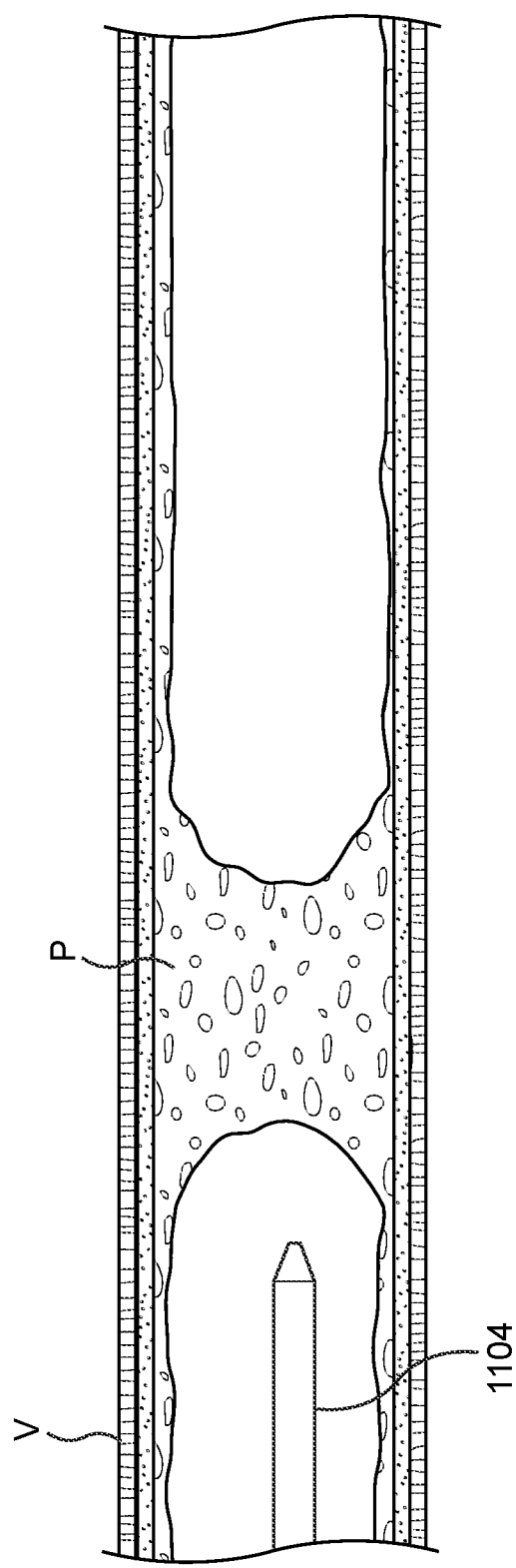

FIG. 11F shows the workhorse guidewire 1102 retracted proximally and removed from the microcatheter, sheath, or other wire exchange catheter 1104. This leaves microcatheter 1104 in the vessel adjacent the obstructive plaque P.

Figure 11G:
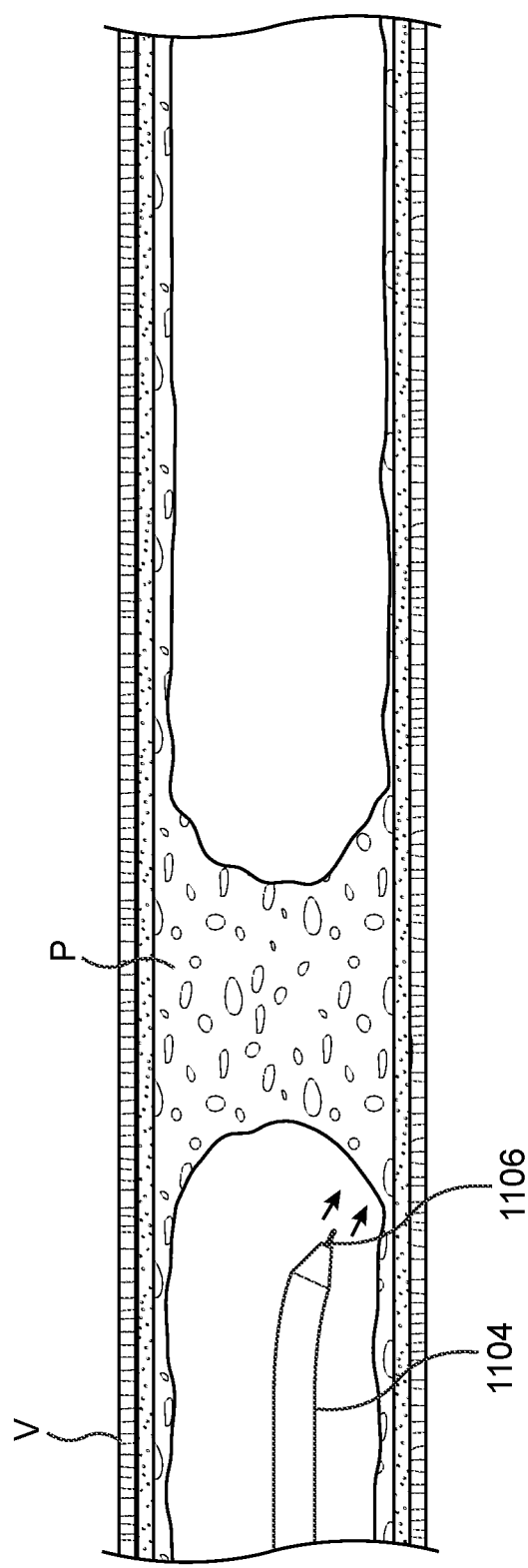

FIG. 11G shows that the workhorse guidewire 1102 is now replaced with a CTO or knuckling wire 1106 which has desirable mechanical properties for passing through the subintimal space past the obstructive plaque. When a CTO wire is used, it may be replaced with a knuckling wire after the CTO wire enters the subintimal space. Here, the knuckling wire 1106 is advanced distally through the microcatheter, sheath or other wire exchange catheter 1104 until it is adjacent the obstructive plaque P. The knuckling wire may be steered into position by manipulating the wire exchange catheter 1104 or by manipulating the knuckling wire 1106 or a combination of both. The wire exchange catheter or the knuckling wire may have straight tips or they have pre-shaped curved tips to allow steering of the tips. Optionally, instead of using a microcatheter and wire, the operator can use alternative methods such as using other dissection devices like the Crossboss device which may be pushed into the subintimal space.

Figure 11H:
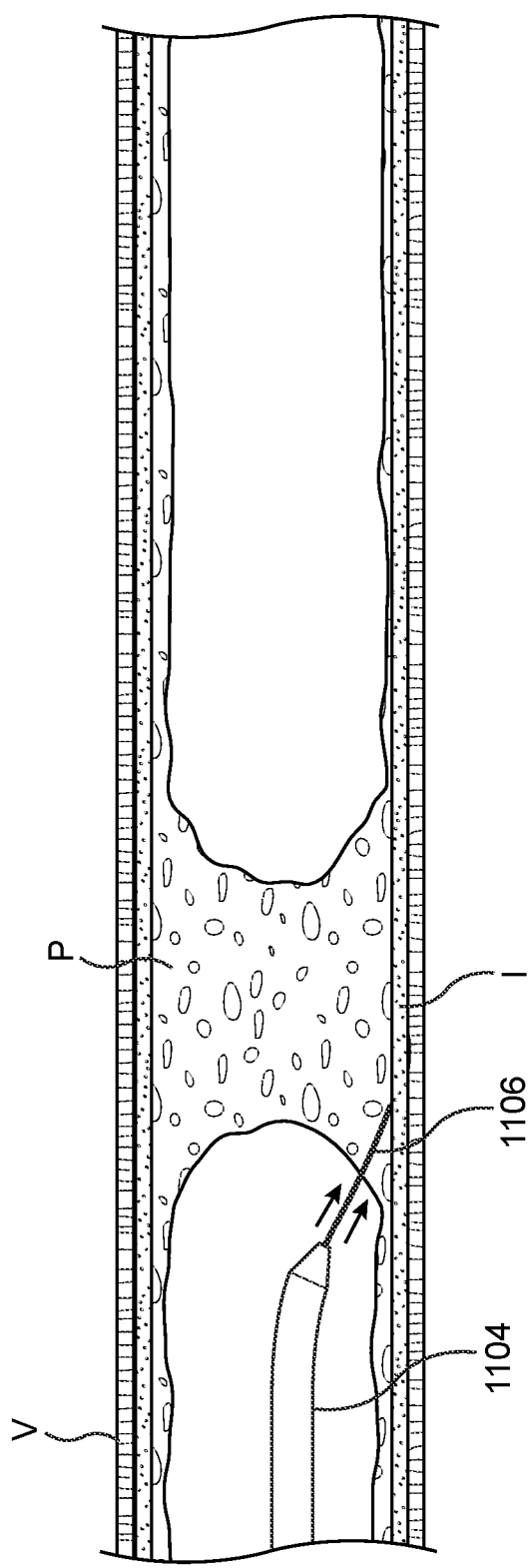

In FIG. 11H, the knuckling wire 1106 is further advanced distally so that it enters a subintimal region of the vessel which is a softer region where the wire may be in a position where it can penetrate through the obstructive plaque P and re-enter into the true lumen of the blood vessel.

Figure 11I:
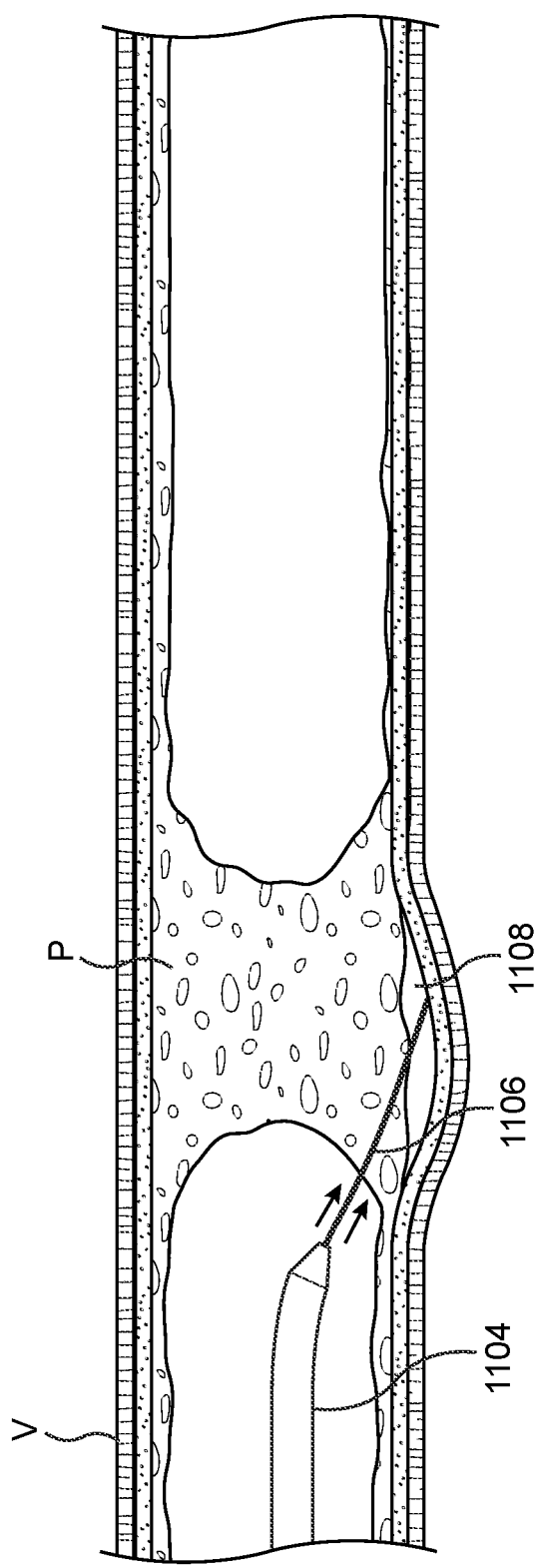

FIG. 11I shows continued distal advancement of the knuckling wire 1106. The knuckling wire 1108 may create a pocket 1108 in the subintimal space as the wire is advanced distally and the pocket may form a false lumen in the vessel.

Figure 11J:
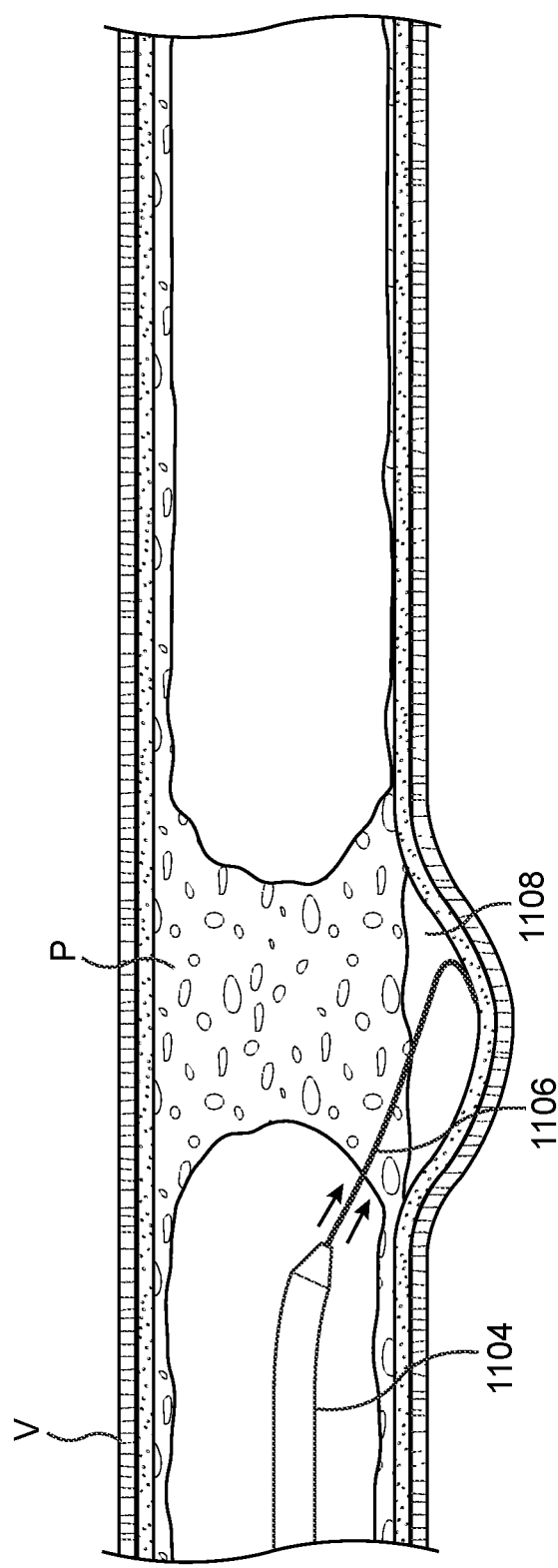

FIG. 11J shows continued distal advancement of the knuckling wire 1106 through the subintimal region of the obstructive plaque P. Further distal advancement of the knuckling wire 1106 may result in the distal end of the wire bending or folding back on itself to form a J-shape like a bent finger that results in a protruding knuckle, hence the term knuckling wire. The pocket 1108 may also continue to enlarge as the knuckling wire is advanced distally.

Figure 11K:
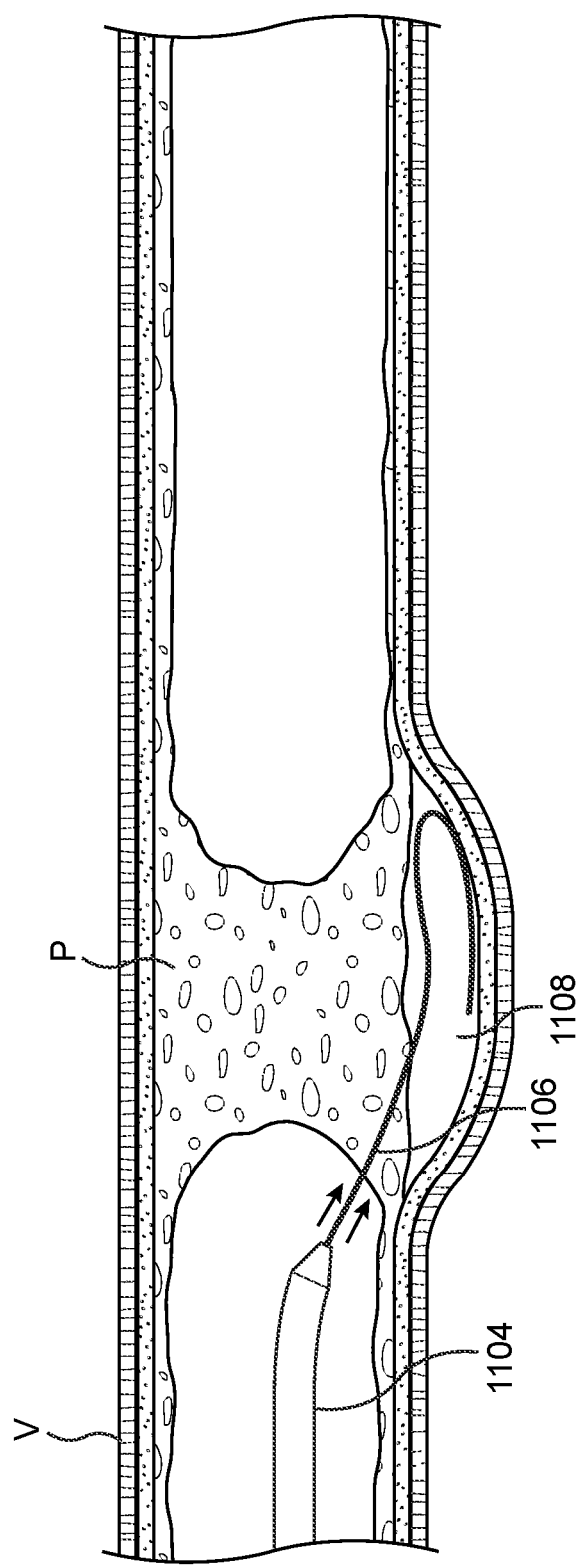

FIG. 11K shows further distal advancement of the knuckling wire 1106 past the obstructive plaque P in the subintimal space. Here, further distal advancement may also cause the knuckling wire to continue to knuckle or fold back on itself and the subintimal pocket 1108 may also continue to enlarge.

Figure 11L:
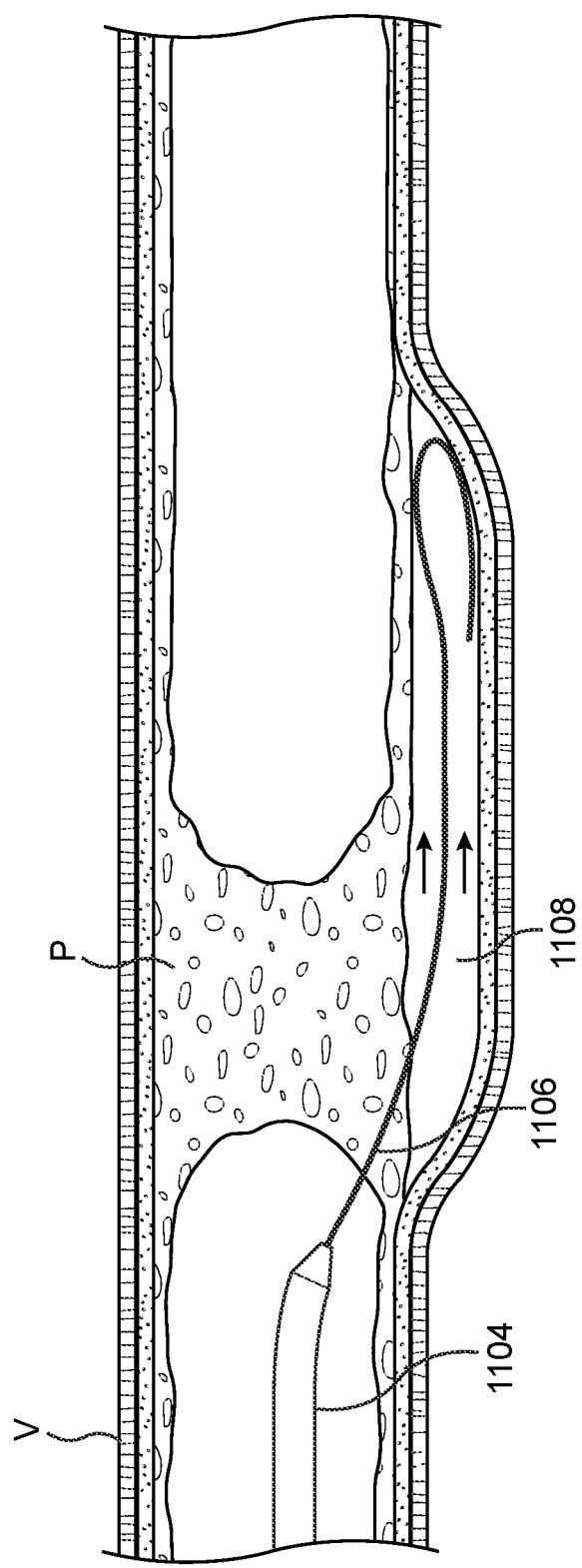

FIG. 11L illustrates further distal advancement of the knuckling wire 1106 in the subintimal space.

Figure 11M:
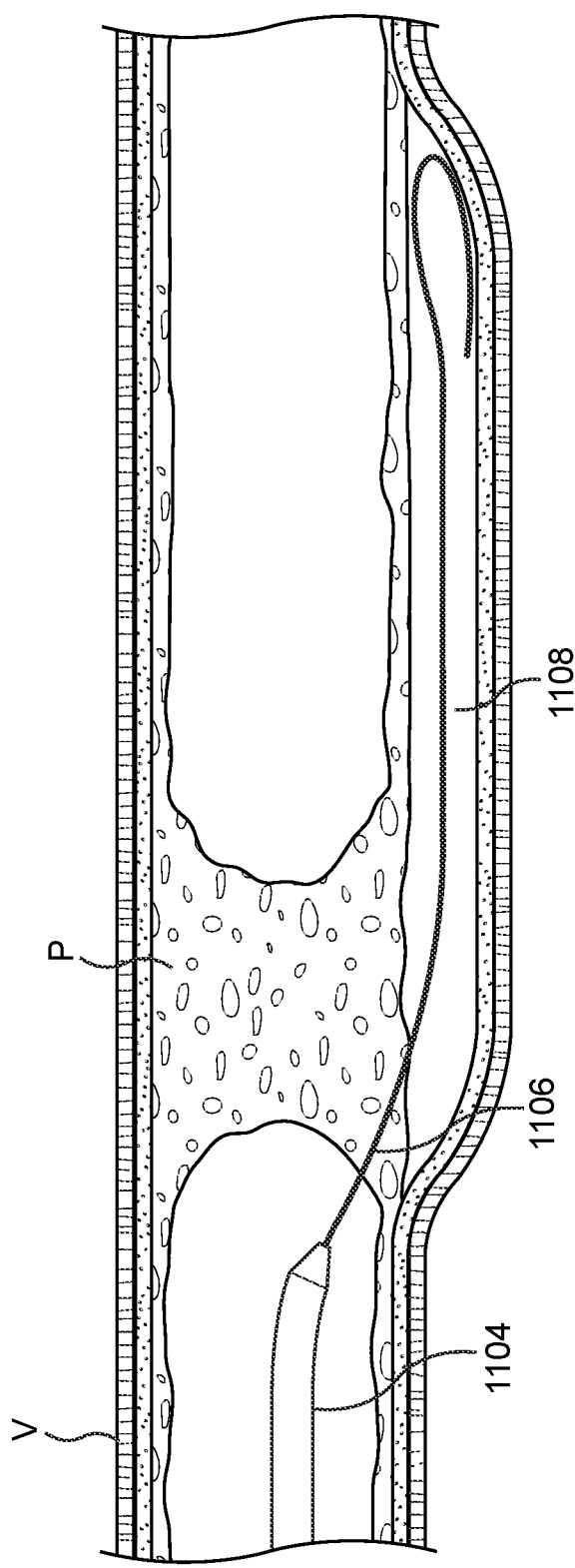

FIG. 11M shows further distal advancement of the knuckling wire 1106 until the distal portion of the knuckling wire is distal of the occlusion formed by obstructive plaque P. While there still remains some plaque such as a thin layer of plaque on the vessel wall, the knuckling wire has gone past the obstruction which is the major hardened region of the obstructive plaque P and the distal portion of the knuckling wire is still in the subintimal space but now disposed under an accessible portion of the true lumen of the vessel.

Figure 11N:
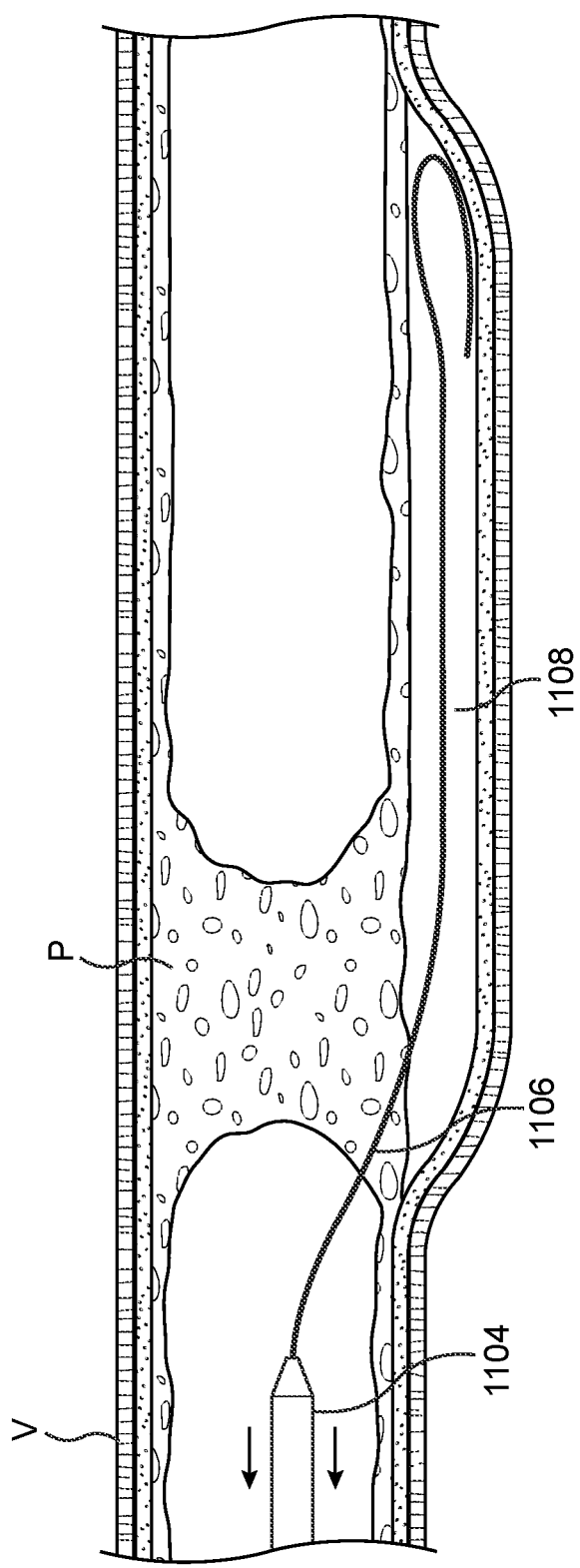

FIG. 11N illustrates that once the knuckling wire has been advanced distally enough to clear the occlusive plaque P and is in a desired position, the operator may proximally retract the wire exchange catheter 1104 and remove it from the patient. Alternatively, the microcatheter can be advanced to the subintimal space and the knuckling wire may be exchanged with any of the re-entry catheters described herein.

Figure 11O:
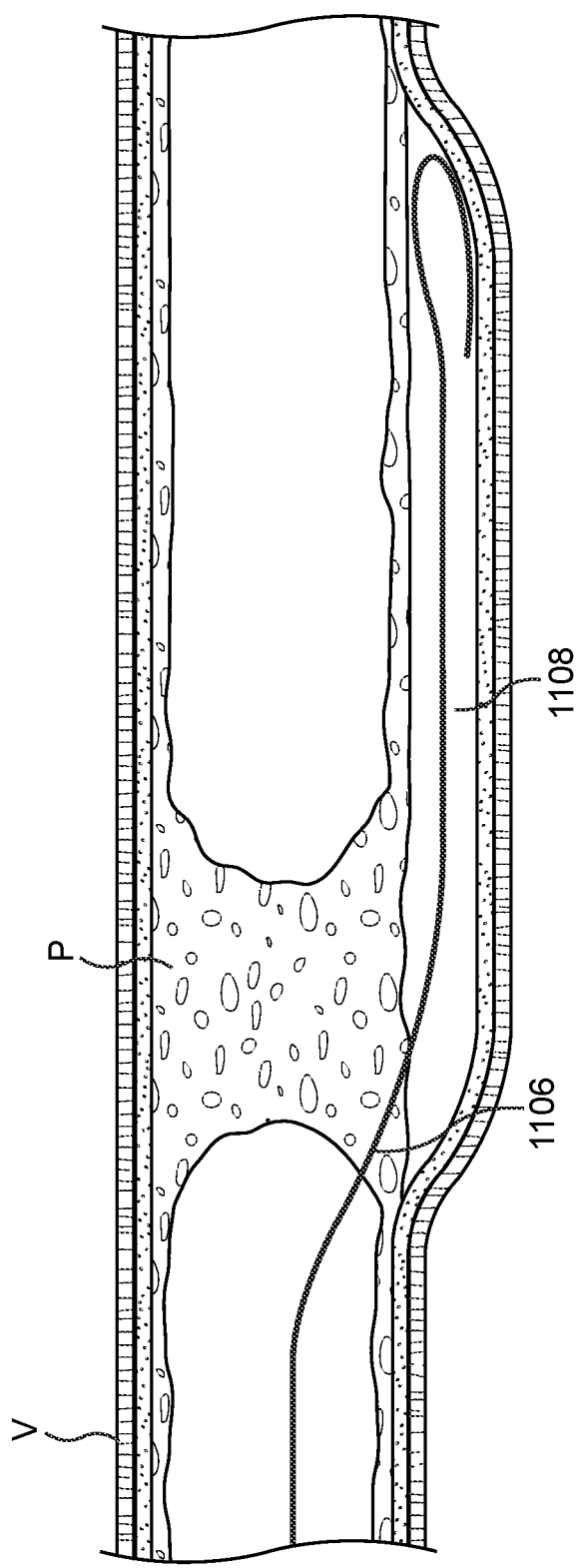

FIG. 11O shows the knuckling wire 1106 (or delivery wire) remaining in the patient after the wire exchange catheter 1104 has been removed. In some situations, the subintimal pocket created by the knuckling wire may need to be enlarged to accommodate the re-entry catheter that will be used. This may be achieved with a balloon catheter or other device.

Figure 11P:
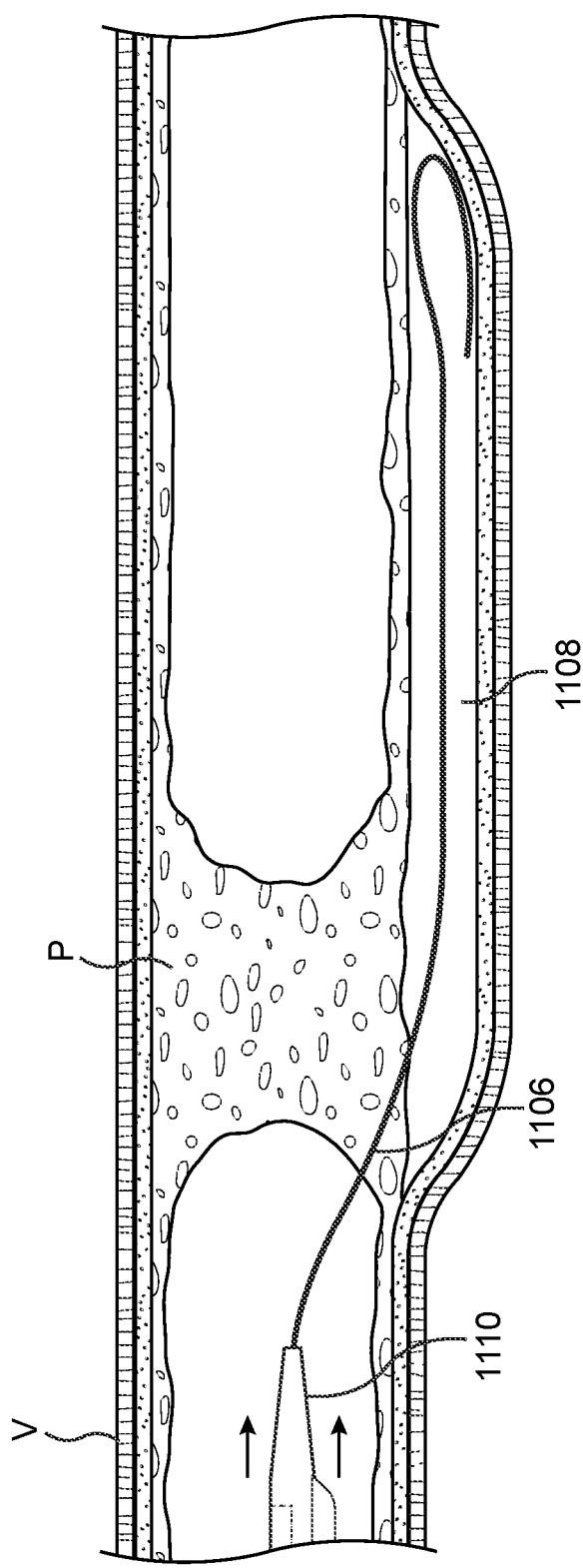

FIG. 11P shows advancement of a re-entry catheter 1110 over the knuckling wire 1106. The re-entry catheter may be any of the examples disclosed herein, but in this example has a configuration where a single common lumen is used for both the guidewire and the re-entry wire, such as the example of FIG. 1. Also, this configuration is the over the wire configuration with an optional balloon. While this example shows advancement of the re-entry catheter over the knuckling wire, one of skill in the art will appreciate that some practitioners may prefer to replace the knuckling wire with another desired guidewire. The wire exchange technique is well known in the art and is similar to the procedure described above where the workhorse wire is exchanged for a knuckling wire. Also, as previously discussed, if a microcatheter is used, it may be advanced into the subintimal space and the knuckling wire may be replaced with any of the re-entry catheters described herein.

Figure 11Q:
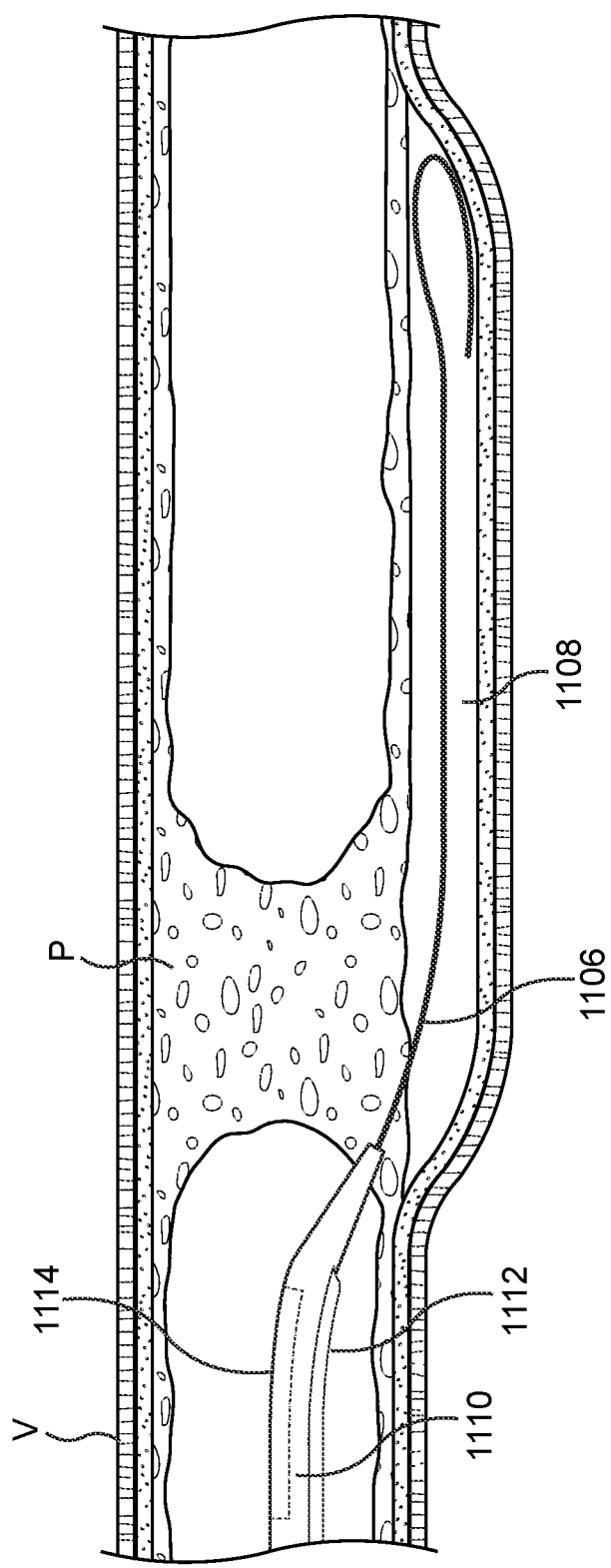

FIG. 11Q shows further distal advancement of the re-entry catheter 1110 over the knuckling wire 1106 so that the re-entry catheter 1110 begins to enter the subintimal space and pass under the obstructive plaque P. The balloon 1112 is in the unexpanded or deflated state during catheter delivery and the ultrasound transducer 1114 is generally on a side opposite of the balloon.

Figure 11R:
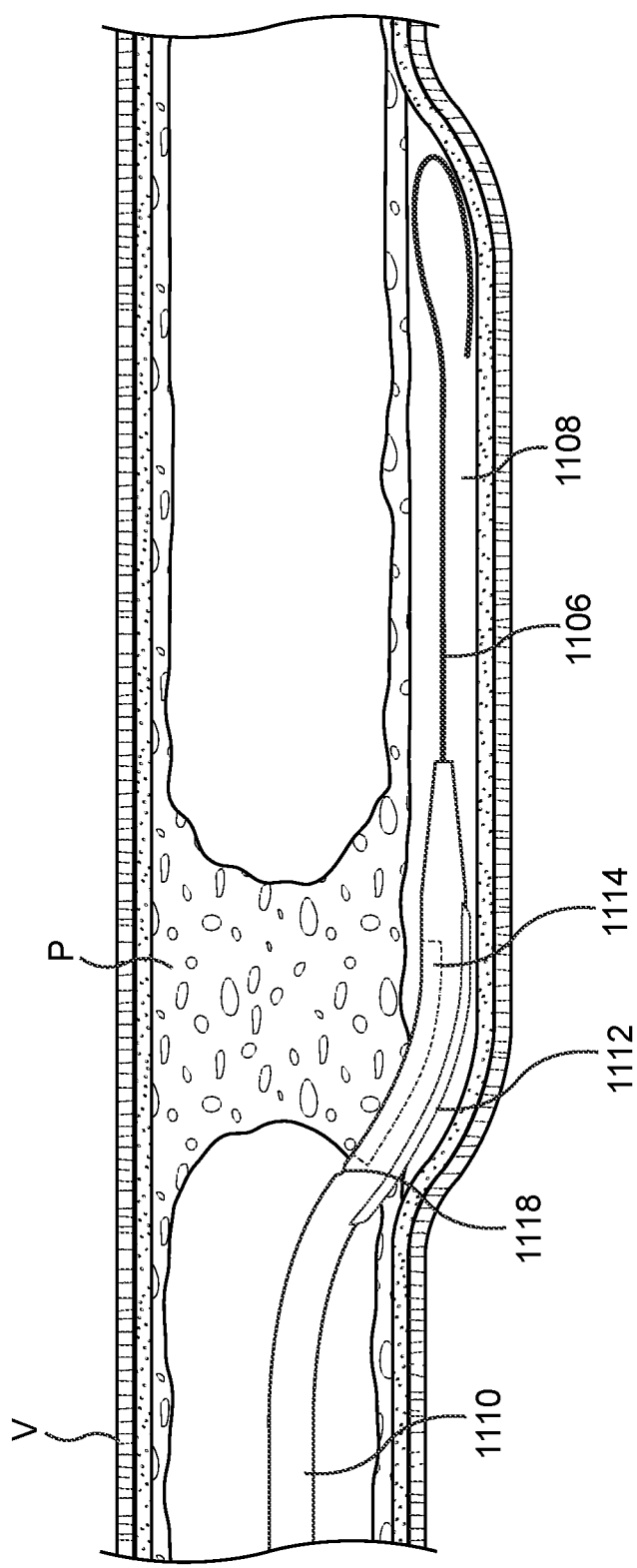

FIG. 11R shows further distal advancement of the re-entry catheter 1110 over the knuckling wire 1106 subintimally under obstructive plaque P and through the false lumen or pocket 1108. Optionally in this step, or any step where a catheter is disposed in the subintimal space creating a pocket 1108, fluid in the pocket may be aspirated out using the catheter if desired to reduce the size of the false lumen created in the subintimal space and allow better apposition of the re-entry port with the tissue adjacent the re-entry position prior to re-entry. If a re-entry catheter with a balloon is used, the balloon may be inflated to prevent blood from filling and expanding the subintimal space.

Figure 11S:
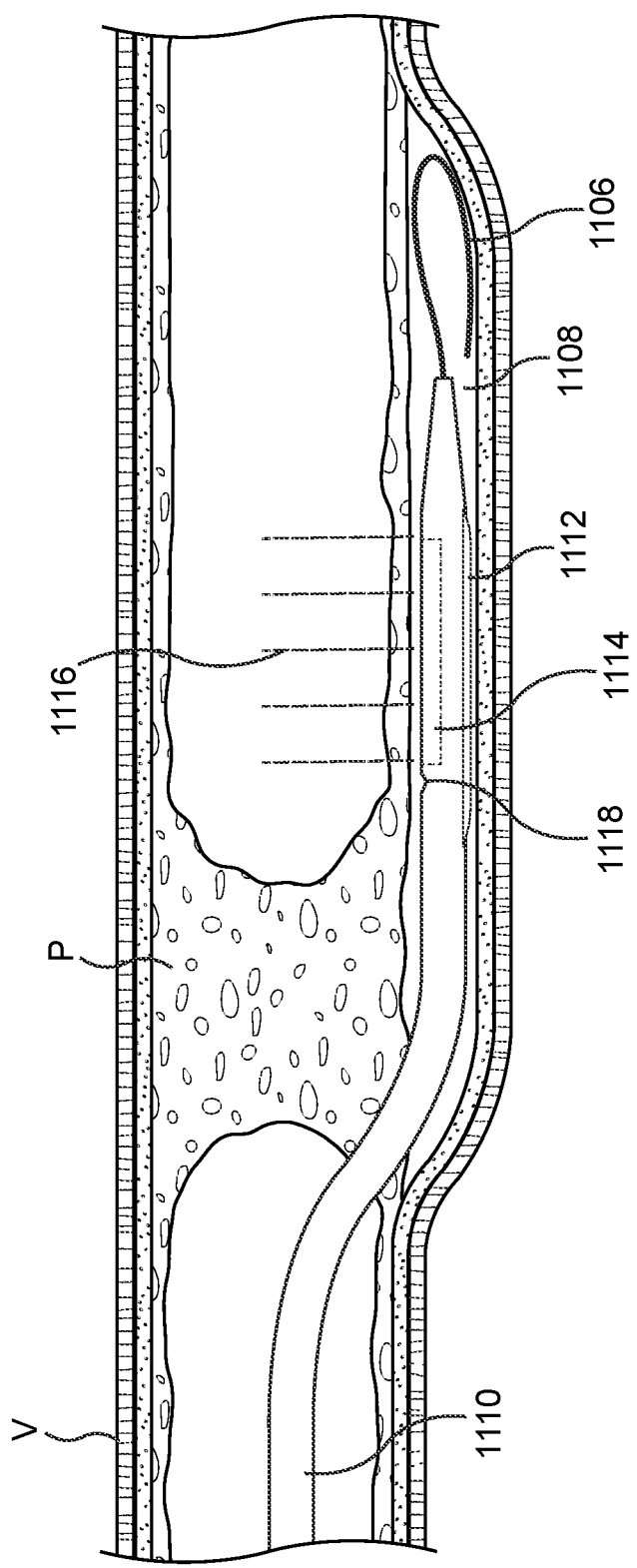

FIG. 11S shows that once the re-entry catheter 1110 is advanced distally far enough, the ultrasound transducer may be used to image the catheter position relative to the local anatomy in order to confirm that the re-entry catheter has been advanced into a desired position where it is sufficiently distal of the obstructive plaque P to clear the obstruction and a desirable re-entry location has been identified. Operators may select the re-entry position as the location where remaining plaque on the vessel walls is the thinnest and softest (least calcified) in order to optimize the chance for safe re-entry into the true lumen. Additionally, the operator may try to identify a re-entry position where the true lumen is the largest.

If the catheter is not in the correct orientation, the re-entry catheter may be moved axially, or the catheter may be rotated by torquing the catheter shaft to orient it so that the ultrasound image and the re-entry port are in the desired position relative to the true lumen.

The ultrasound beam 1116 is emitted from the ultrasound transducer 1114 at an angle to form an image that guides the operator during the procedure. The angle when measured between the ultrasound beam and the longitudinal axis of the catheter may be any angle, such as 0 degrees to 180 degrees. For example, the ultrasound beam angle may be 90 degrees. An ultrasound imaging axis angle of 0 to less than 90 degrees is distally facing, while an angle of 90 degrees is perpendicular to the longitudinal axis of the catheter (or side firing) as illustrated in FIG. 11S, and an angle of greater than 90 degrees up to 180 degrees is proximally facing. Other examples of the ultrasound beam angle may be from 0 degrees to 135 degrees. The ultrasound beam angle allows an ultrasound image to be obtained that not only shows the anatomy around the re-entry point of the vessel, but also shows the re-entry point where a re-entry wire exits the subintimal space and re-enters the vessel true lumen and shows the re-entry wire as it is advanced distally, thereby allowing the operator to observe the re-entry wire to ensure that it re-enters the true lumen in a desired location and is properly advanced and does not puncture the vessel or propagate the dissection that was used to create the subintimal pocket.

The re-entry wire 130 can exit the re-entry port at any angle, for example when the re-entry wire exits the re-entry port in a distally facing direction, the re-entry angle would be from 0 degrees to less than 90 degrees. If the re-entry wire exits perpendicular to the longitudinal axis of the catheter, then the re-entry wire would exit at a 90 degree angle relative to the longitudinal axis of the catheter. In some examples, the re-entry wire may exit the re-entry port facing proximally in which case the re-entry angle would be greater than 90 degrees up to 180 degrees.

The ultrasound imaging axis is selected so that its angle cooperates with the re-entry angle and allows visualization of the re-entry wire. In some examples, the re-entry angle may be 30 degrees, 45 degrees, 60 degrees, or 90 degrees relative to the longitudinal axis of the catheter and the ultrasound imaging axis may be perpendicular (e.g. 90 degrees) or distally facing (e.g. 0 degrees to 90 degrees). In some examples the ultrasound beam angle may be proximally facing (e.g. greater than 90 degrees to 180 degrees). In some examples the ultrasound beam may be 90 degrees and the re-entry wire exits the re-entry port at 60-75 degrees. In any example the ultrasound beam angle may be 0 to 135 degrees. These features of the ultrasound transducer may be used in this example of any of the examples of re-entry catheter disclosed herein that include an ultrasound transducer.

The re-entry port 1118 is just proximal of the proximal end of the ultrasound transducer. Therefore, when the re-entry wire exits the re-entry port it will enter into the region imaged by the ultrasound transducer. This allows the operator to ensure that the re-entry wire exits into a desired area of the true lumen as verified by the ultrasound image just taken. In some examples, the ultrasound beam angle is the same as the re-entry wire port angle. In other examples, the ultrasound beam angle may not be the same as the re-entry wire port angle. In other examples, the re-entry wire exits the re-entry port at an angle that is transverse to the ultrasound beam angle.

Figure 11T:
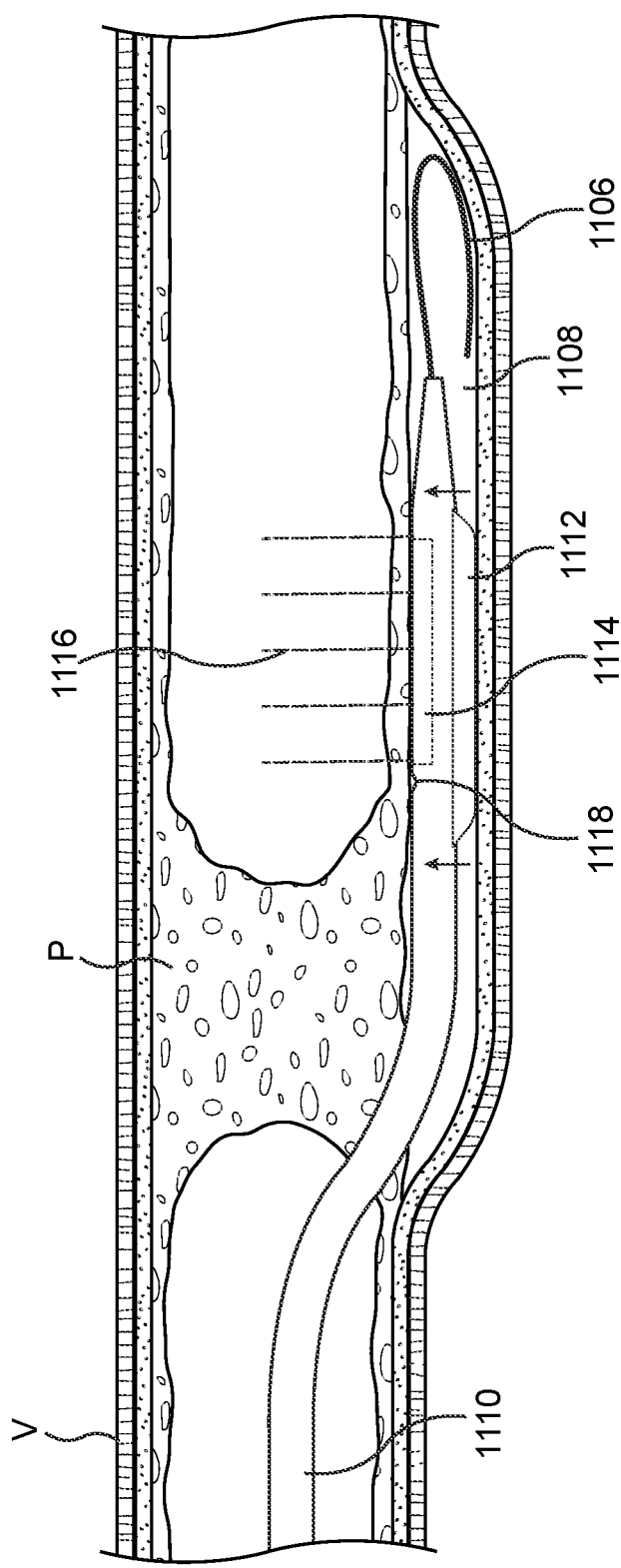

FIG. 11T shows that once the re-entry port has been disposed in a desired position to ensure that the re-entry wire will exit into a desired portion of the true lumen, the balloon 1112 may be expanded with fluid such as dilute contrast media, saline, a gas, or mixtures thereof. Because the balloon is disposed asymmetrically on only one side of the catheter, and may be centered opposite the re-entry port, expansion of the balloon displaces the distal portion of the catheter radially inward away from the vessel wall and so that the re-entry port is apposed with the tissue or remaining plaque in the vessel. This anchors the catheter distal portion and prevents unwanted movement and further ensures that the re-entry wire will enter the true lumen in the desired location. The desired position may be where the remaining plaque is the thinnest or softest and where the true lumen may be the largest size. Optional further imaging with the ultrasound transducer will reconfirm proper positioning and placement of the re-entry port. In particular, the ultrasound imaging will allow optimal balloon expansion, such that the re-entry port is apposed with the plaque but not inflated to a point that the balloon inflation creates a compression of the targeted true lumen.

Figure 11U:
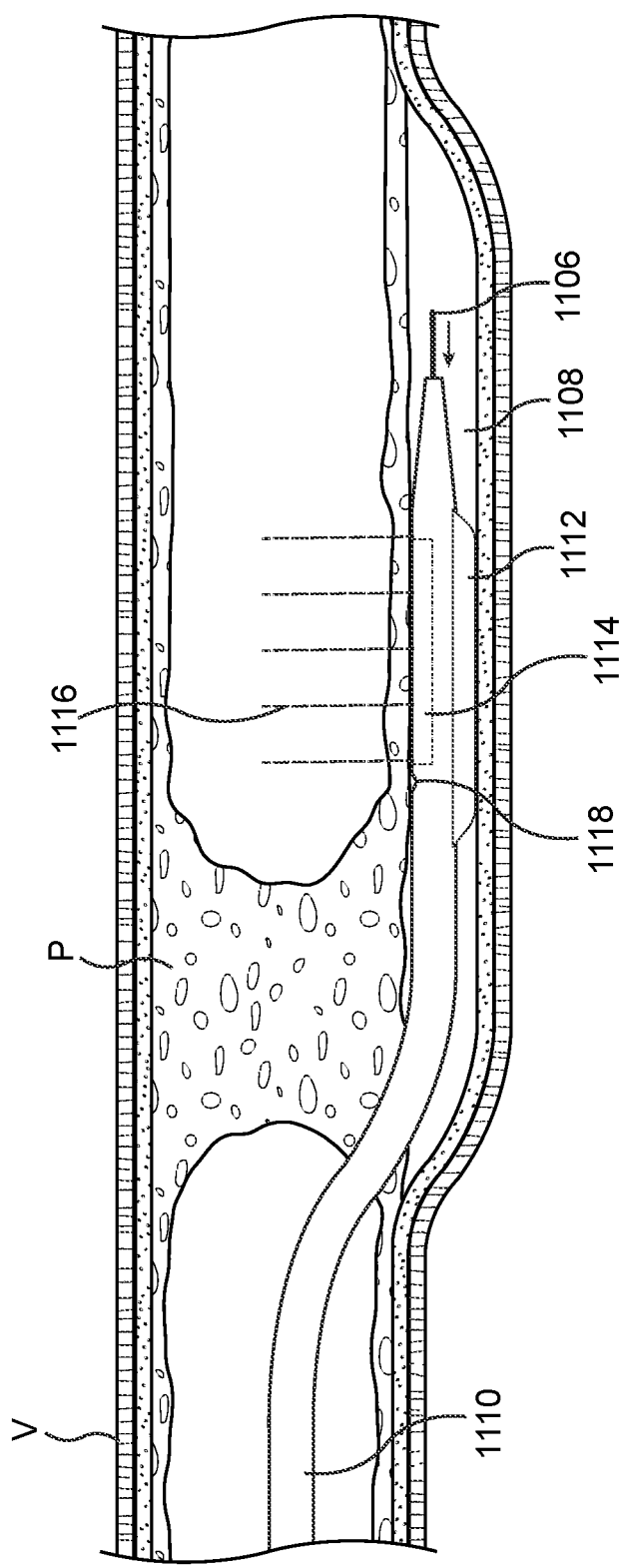

FIG. 11U shows that once the re-entry catheter has been properly positioned relative to the occlusive plaque P and anchored with the balloon (if used), the knuckle wire (or delivery wire) 1106 may be proximally retracted and removed from the re-entry catheter 1110. Here, the re-entry port 1118 and ultrasound transducer 1114 are distal of the occlusive plaque P. In some cases, the knuckle wire may have been replaced earlier with another guidewire and therefore in that situation, that guidewire will be removed rather than the knuckle wire. The balloon may remain inflated to anchor the catheter and prevent unwanted movement during proximal retraction of the knuckle wire (or other guidewire if previously replaced). Ultrasound imaging 1116 may be continued at any time if desired in order to confirm that unwanted movement has not occurred.

Figure 11V:
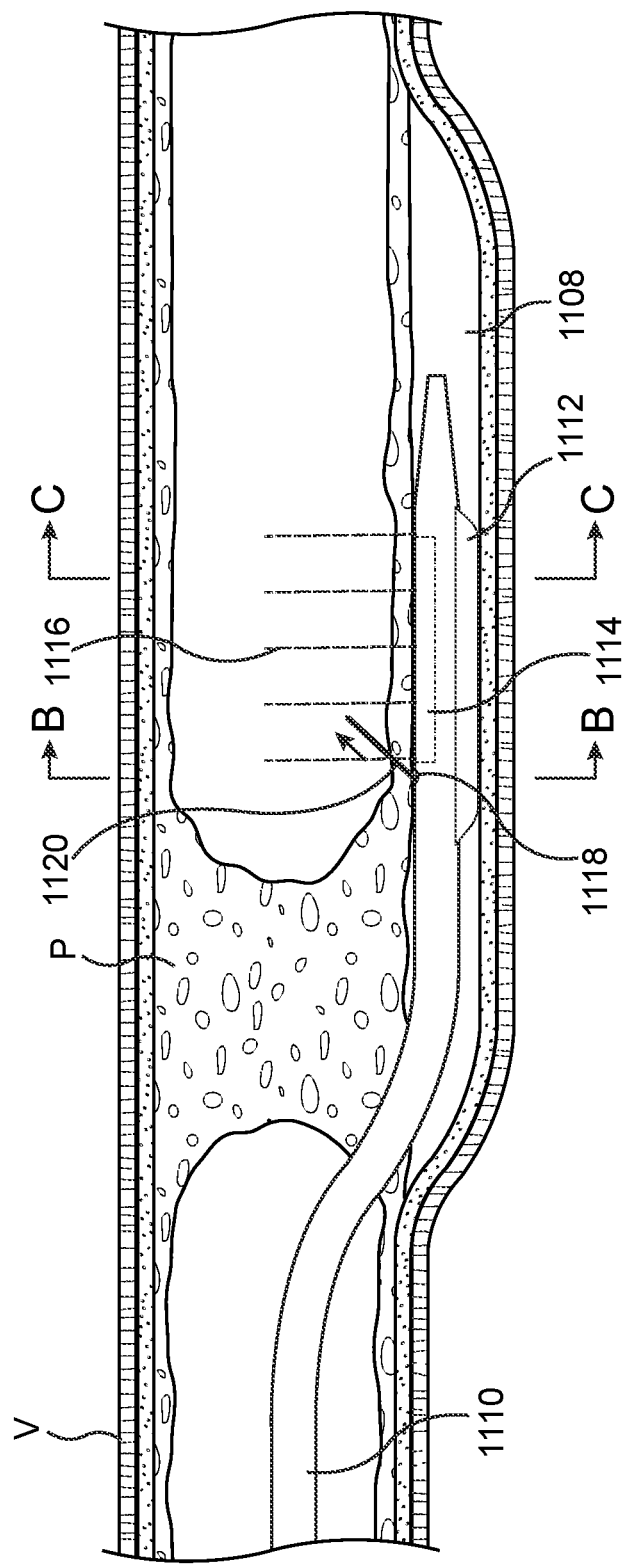

FIG. 11V shows a re-entry wire 1118 advanced distally through the central lumen of the catheter which is now free of the knuckle wire. The re-entry wire 1120 is advanced until it exits the re-entry port 1118. The re-entry wire will exit the re-entry port 1118 at an angle that that can be observed with the ultrasound. Therefore, the re-entry wire will follow a path that has been imaged by the ultrasound transducer and determined to be acceptable by the operator and ensures that the re-entry wire will properly re-enter the true lumen of the blood vessel. The re-entry wire may be stiffer than the knuckling wire so that it will more easily pass back into the true lumen through any tissue and plaque.

Figure 11X:
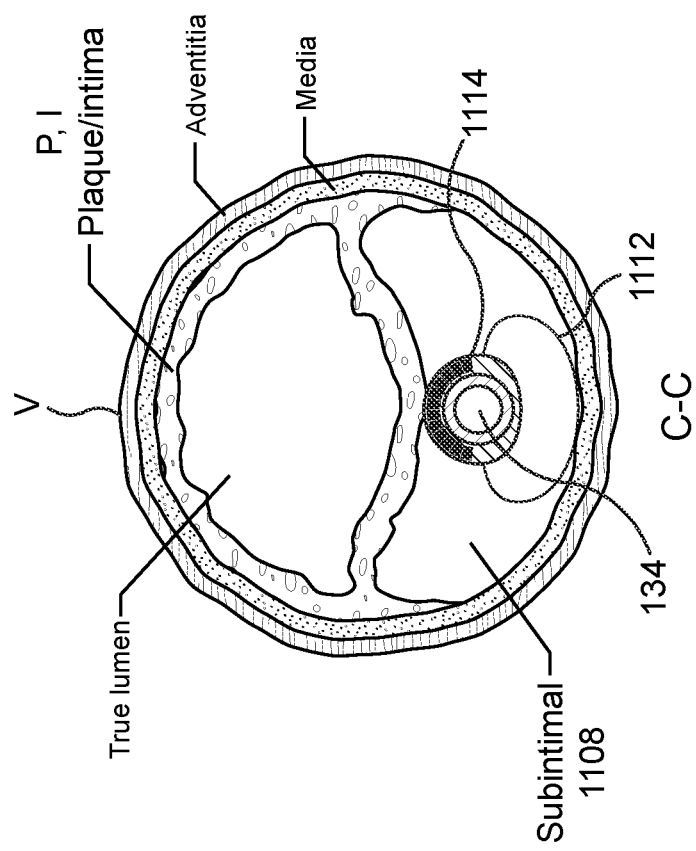
Figure 11W:
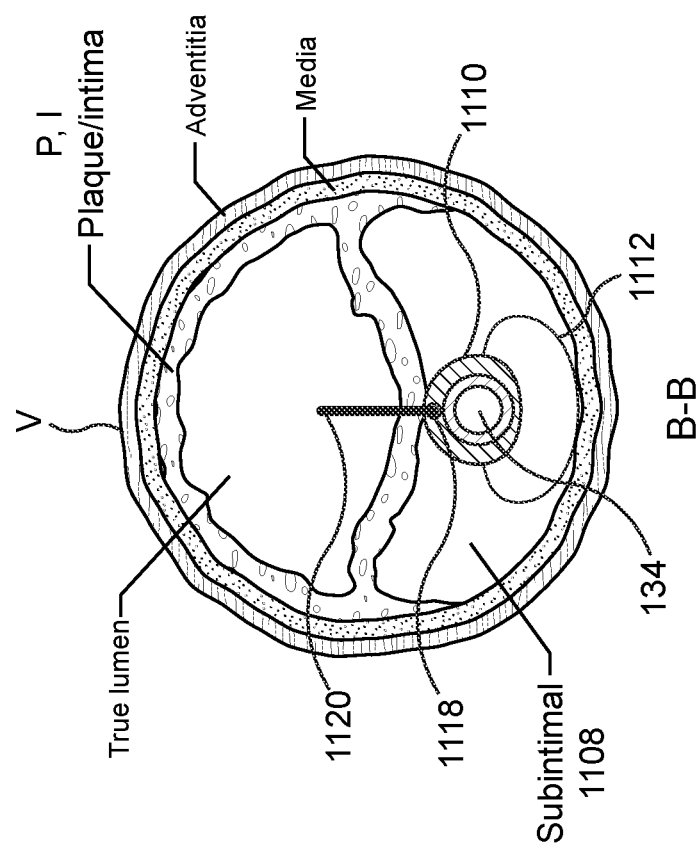

FIGS. 11W-11X show various cross-sections taken along the longitudinal axis of the blood vessel and catheter shown in FIG. 11V.

FIG. 11W is a cross-section taken along the line B-B in FIG. 11V. Here, the re-entry wire 1120 is clearly shown exiting the re-entry port 1118 from lumen 134 of the catheter 1110 and passing from the subintimal space or false lumen (pocket) 1108 back into the true lumen of the vessel. The inflated balloon 1112 moves the re-entry port radially inward and away from the vessel wall to ensure that the re-entry port is properly positioned.

FIG. 11X is a cross-section taken along the line C-C in FIG. 11V which is slightly distal of the cross-section in FIG. 11W. Here the ultrasound transducer 1114 is clearly seen along with the inflated balloon 1112 which moves the catheter radially inward and away from the vessel wall to help anchor it and position the re-entry wire port into a desired position, and provides backup anchoring of the catheter to enhance the wire re-entry.

Figure 11Y:
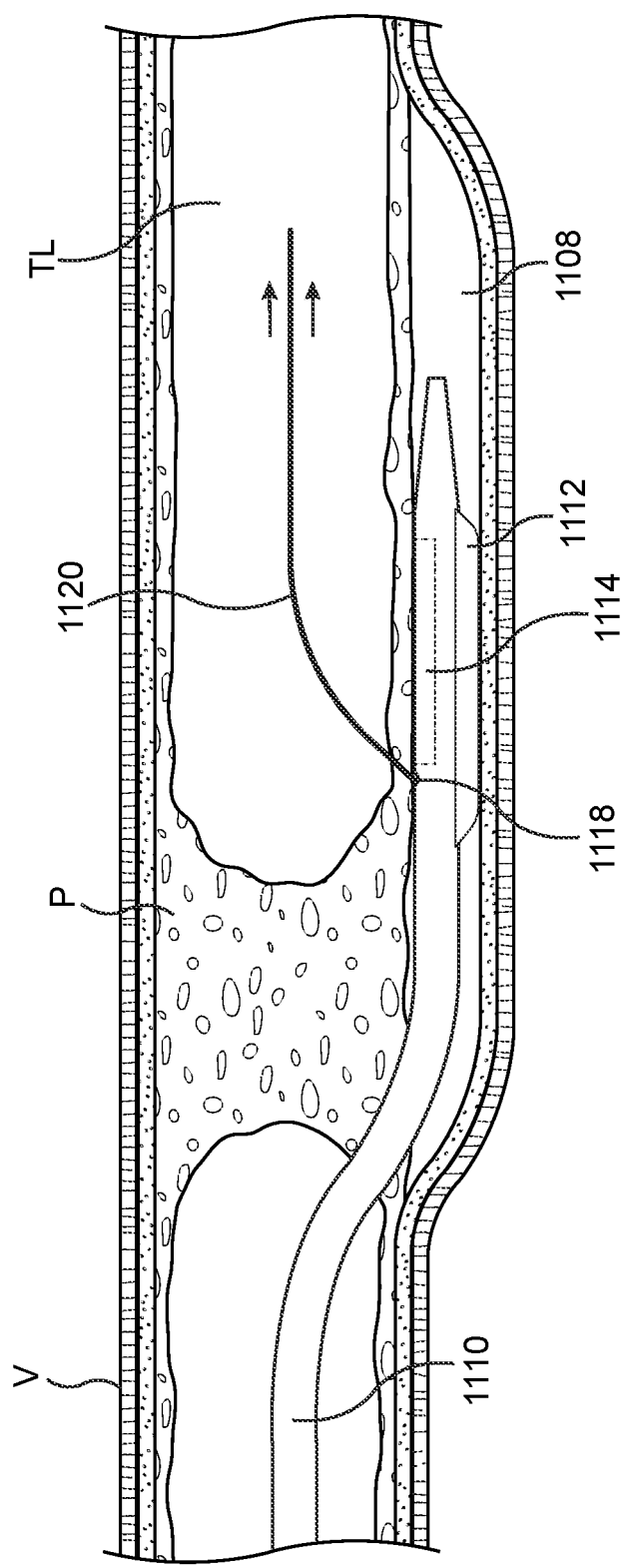

FIG. 11Y illustrates that once the re-entry port 1118 has been properly positioned and the re-entry wire 1120 exits the re-entry port 1118 into the true lumen of the vessel, the re-entry wire is further advanced distally into the true lumen TL of the vessel. Advancement of the re-entry wire may be observed under ultrasound guidance as needed (not illustrated here).

Figure 11Z:
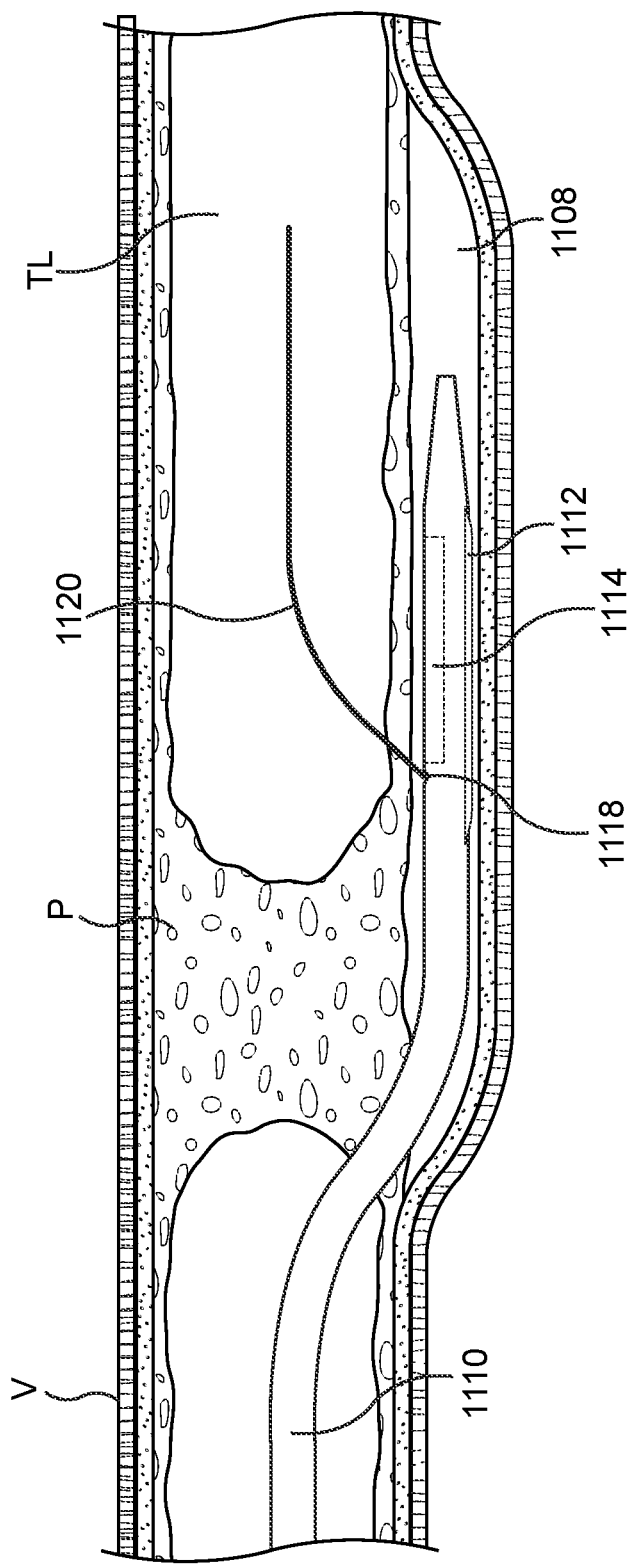
Figure 11A:
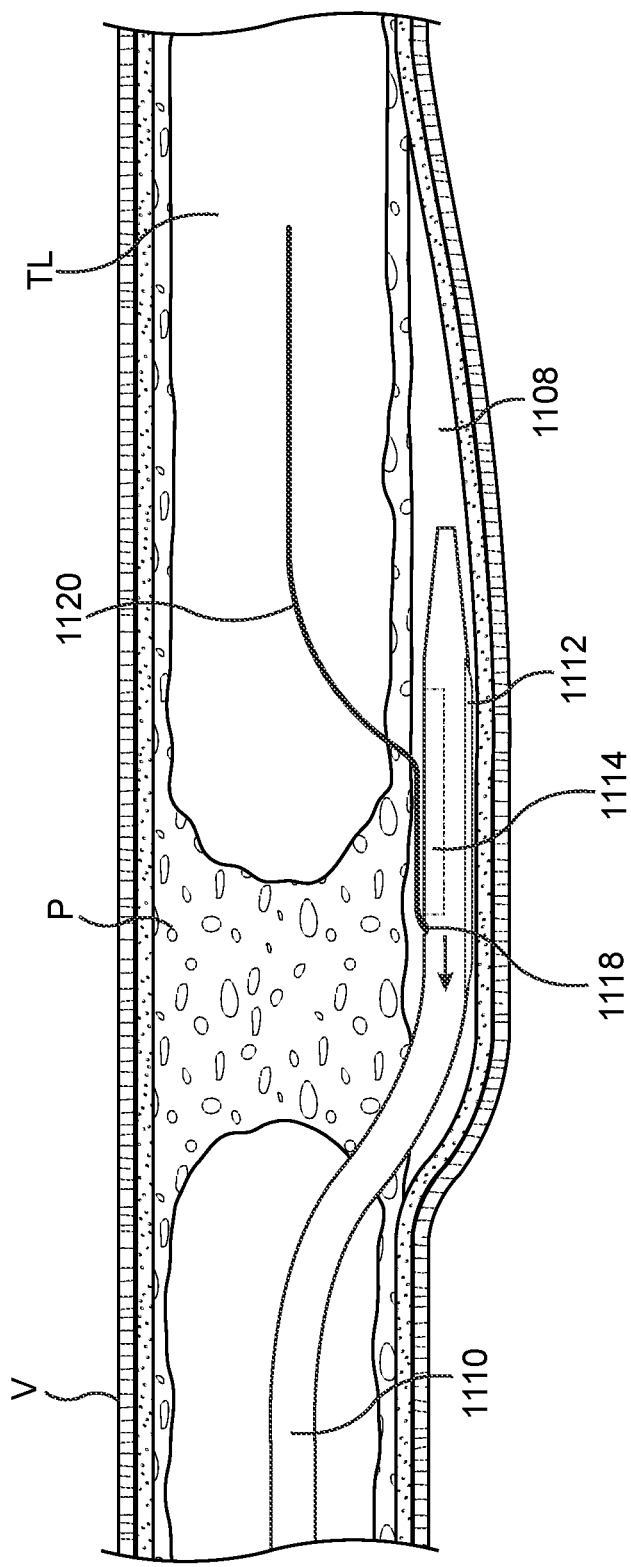
Figure 11A:
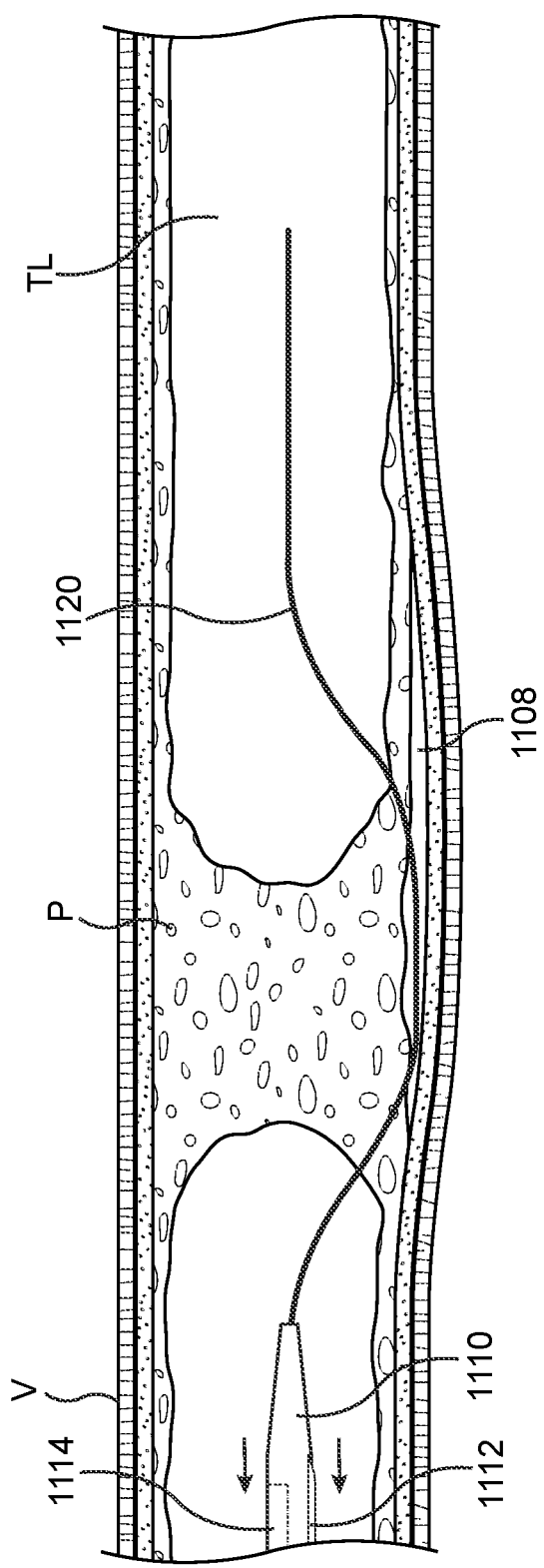
Figure 11A:
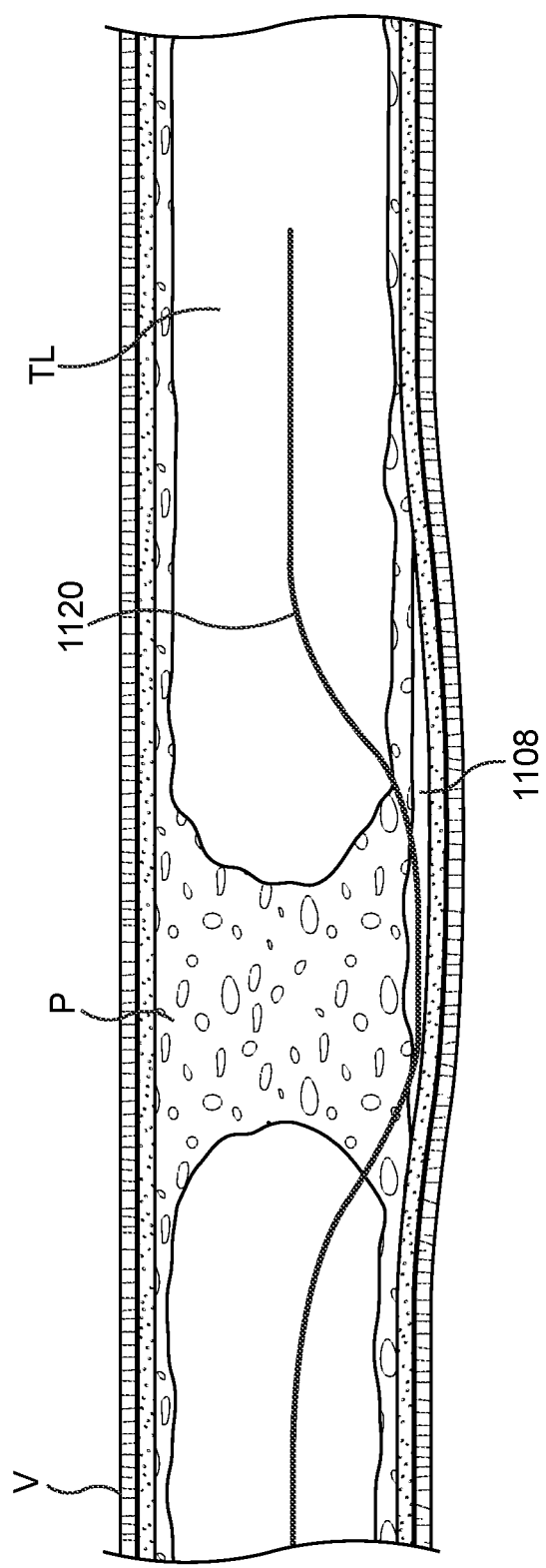
Figure 11A:
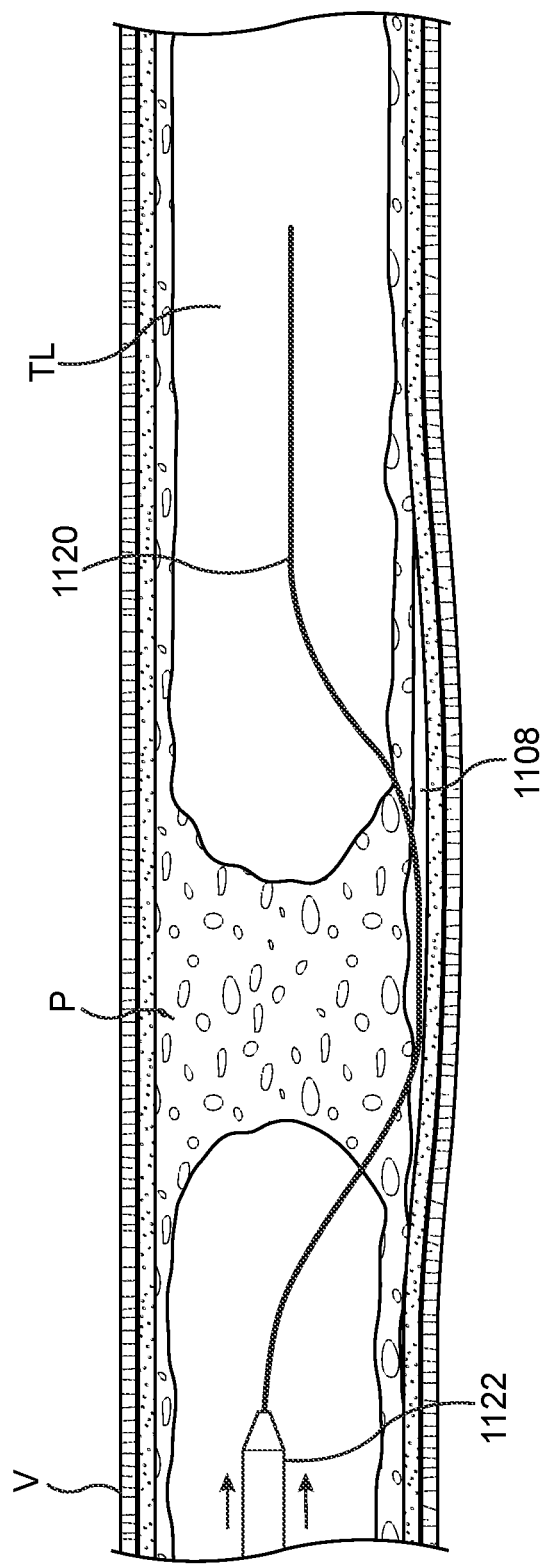
Figure 11A:
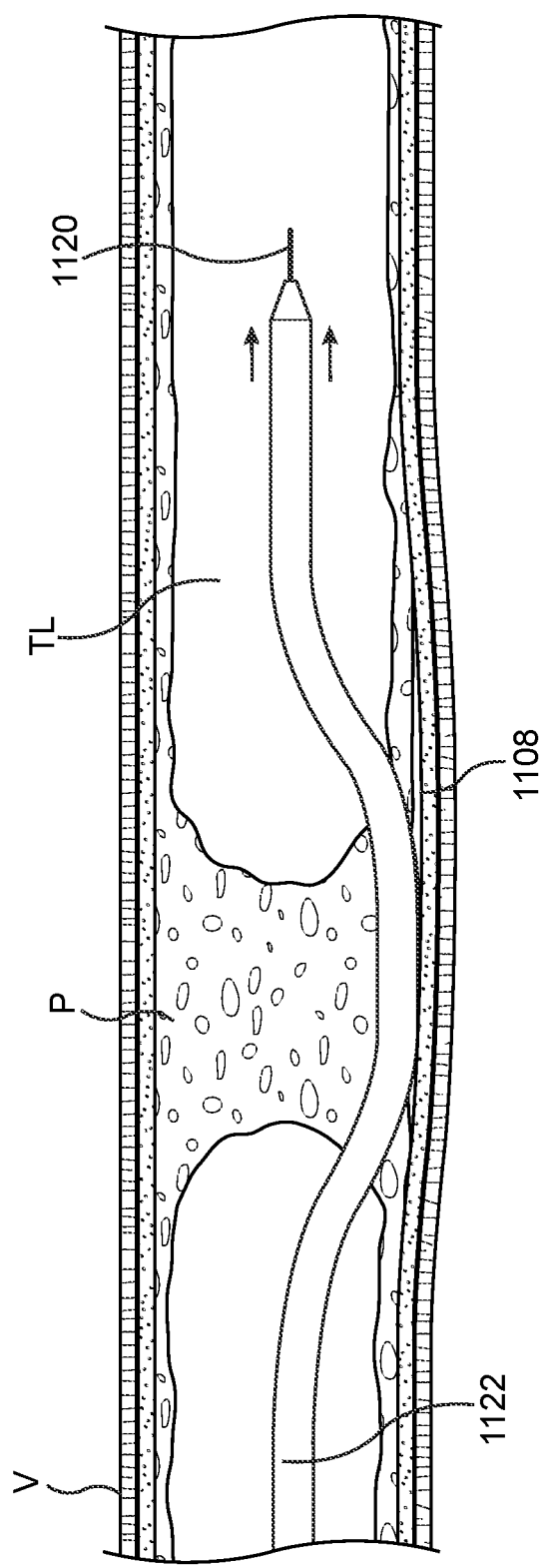
Figure 11A:
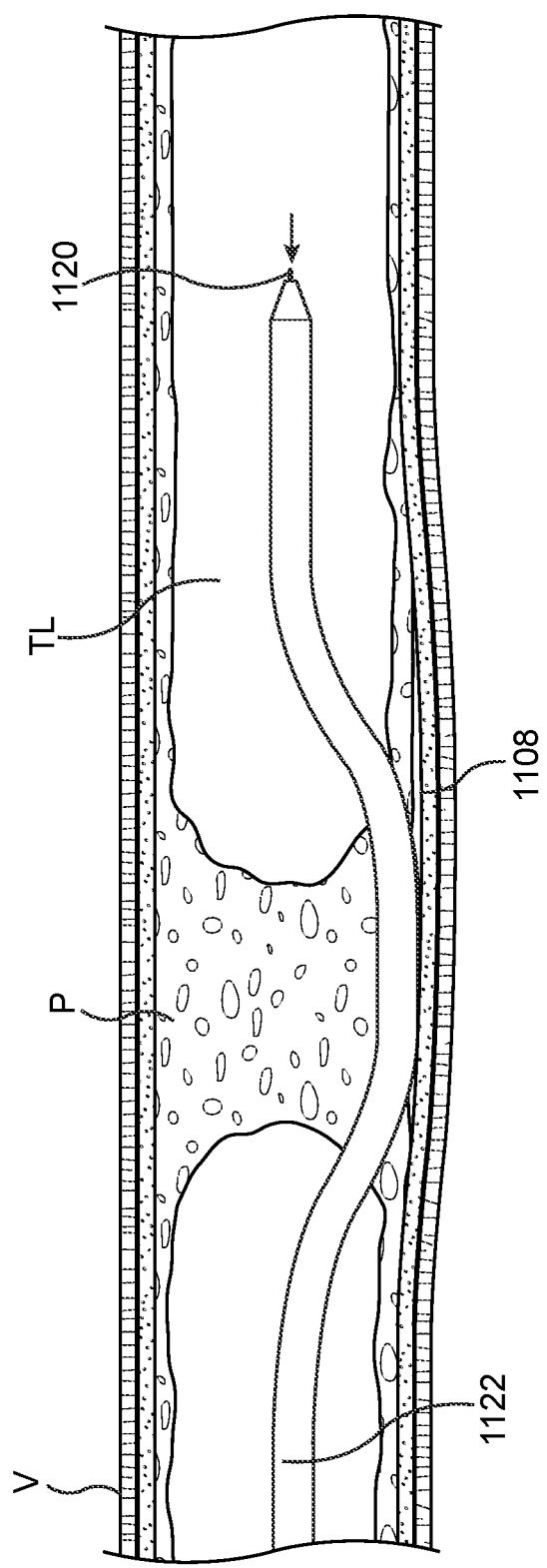
Figure 11A:
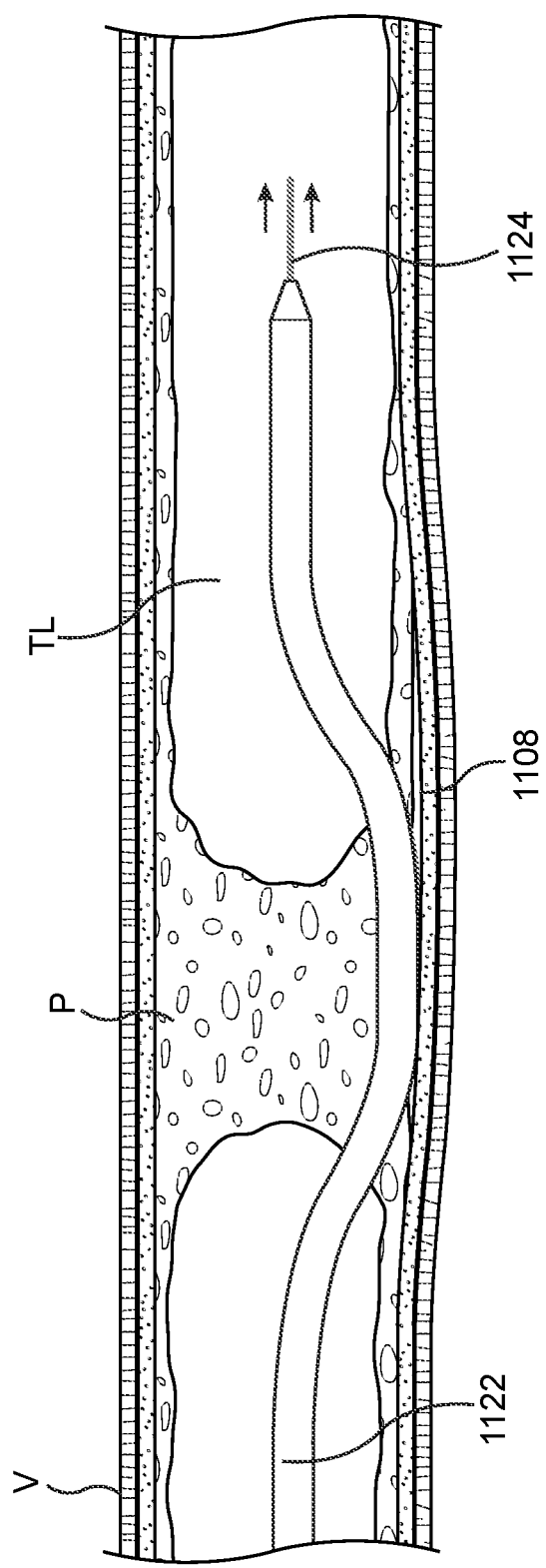
Figure 11A:
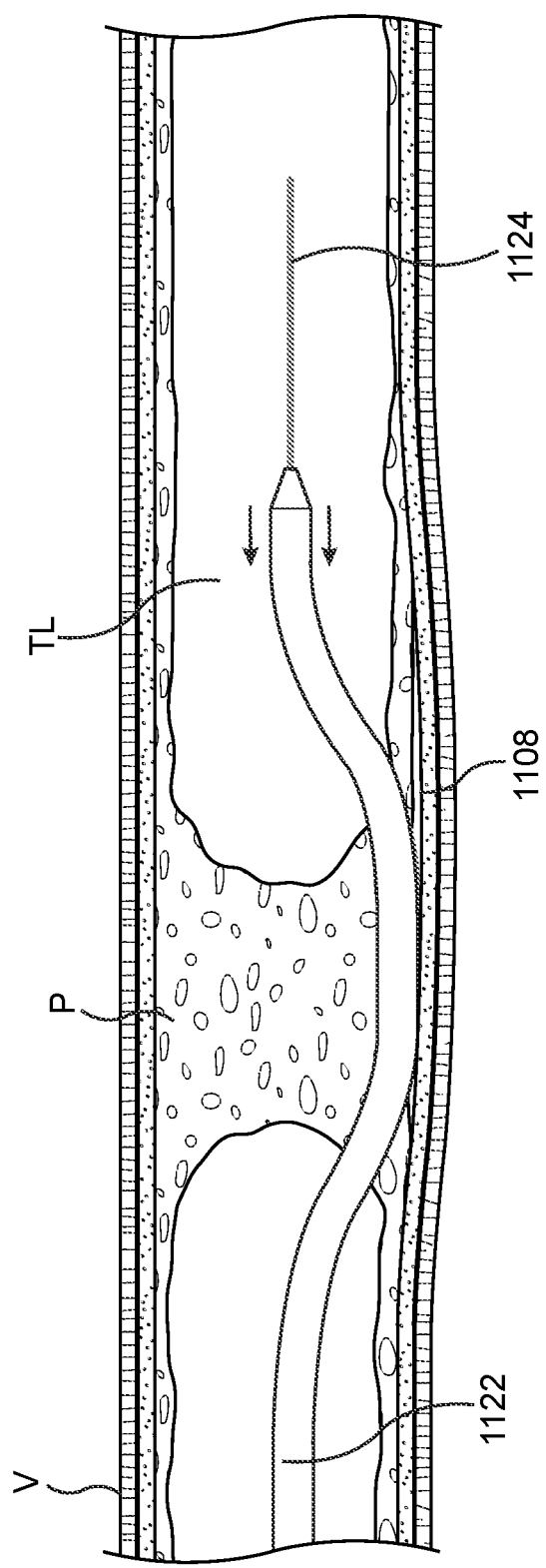
Figure 11A:
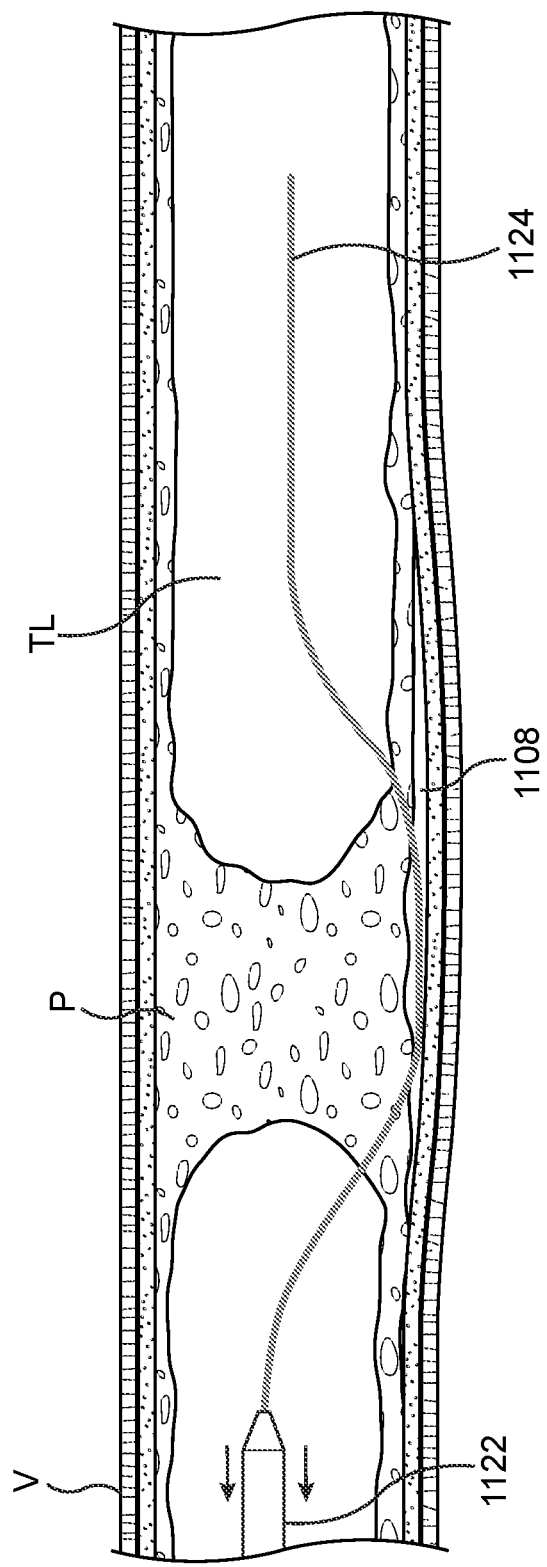
Figure 11A:
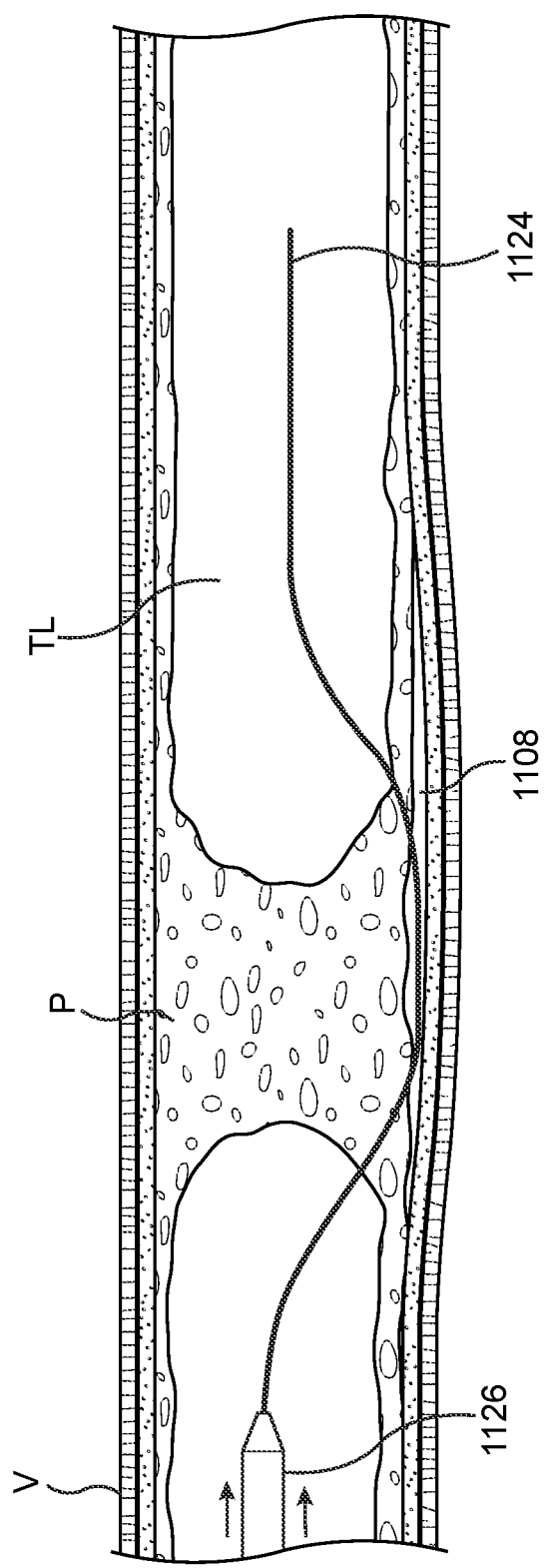
Figure 11A:
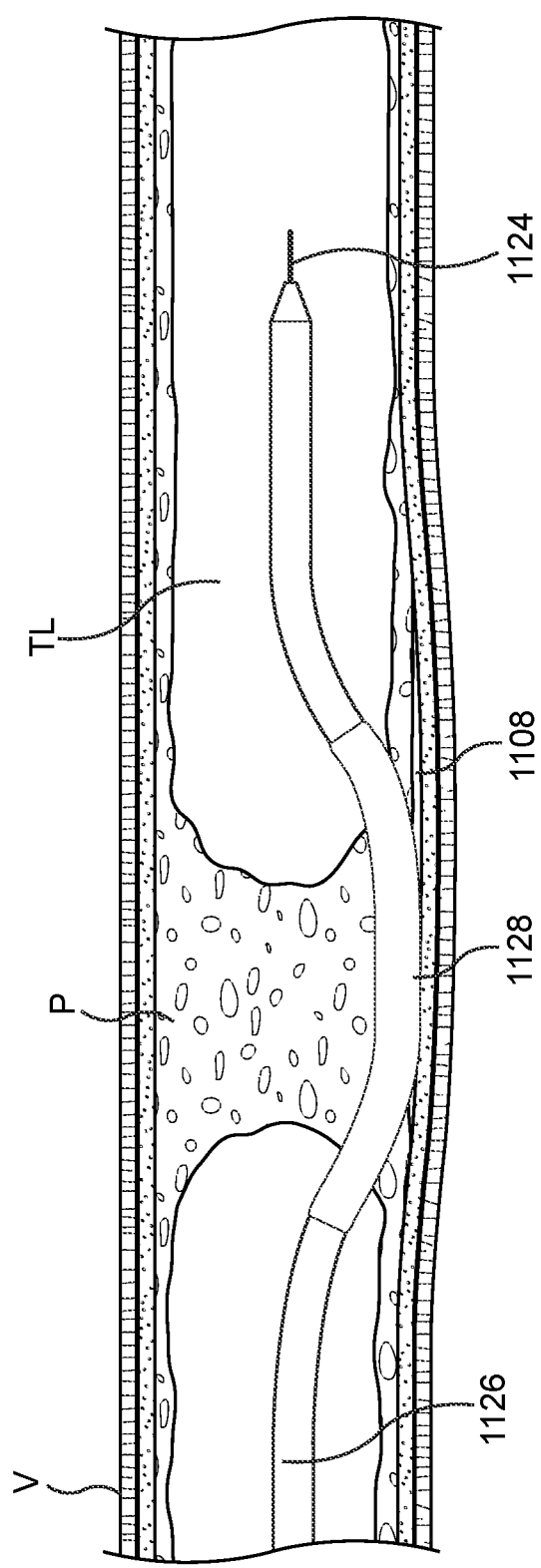
Figure 11A:
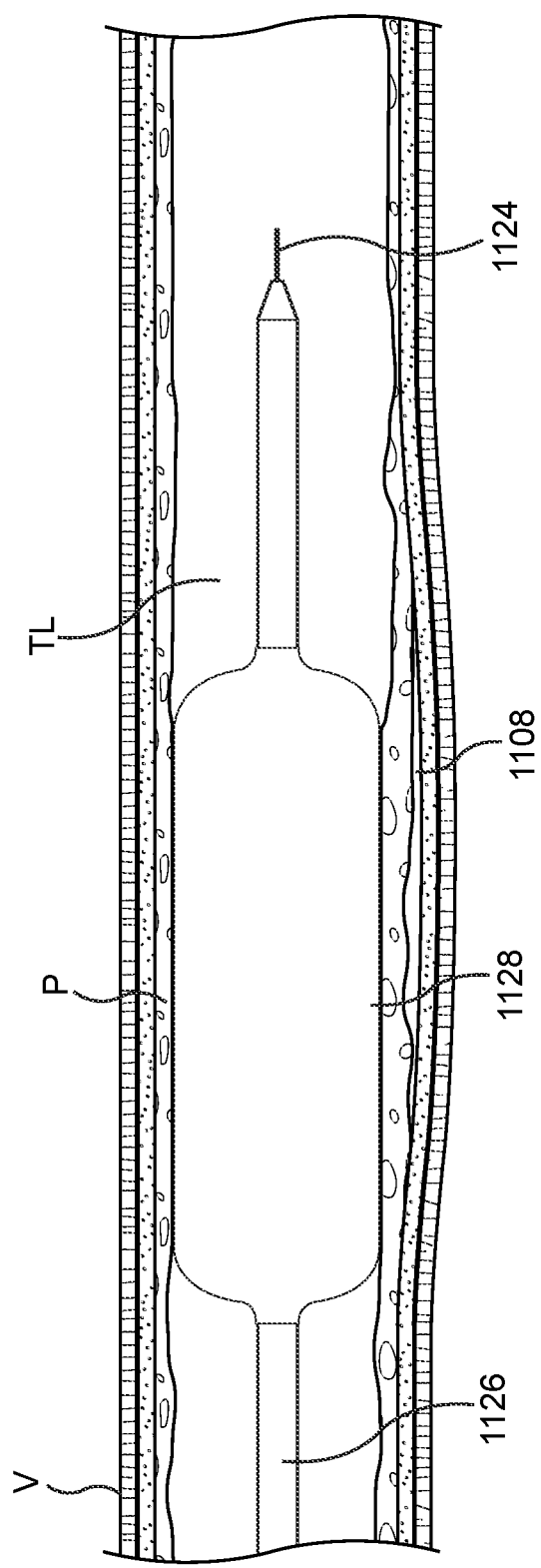
Figure 11A:
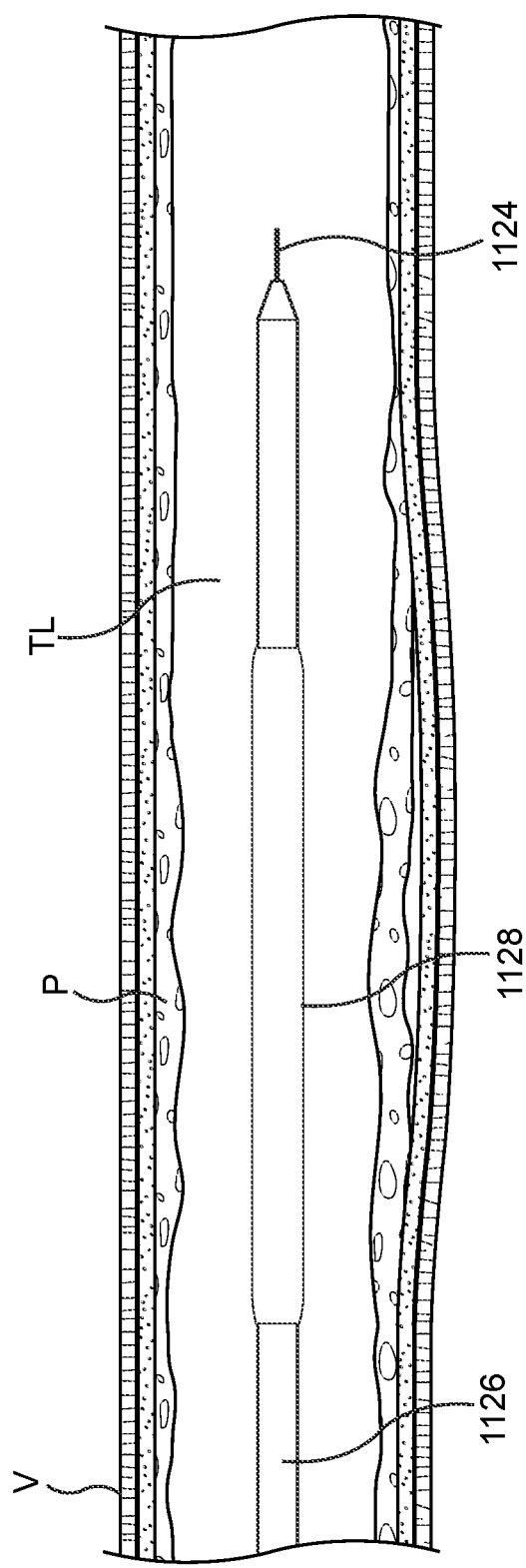
Figure 11A:
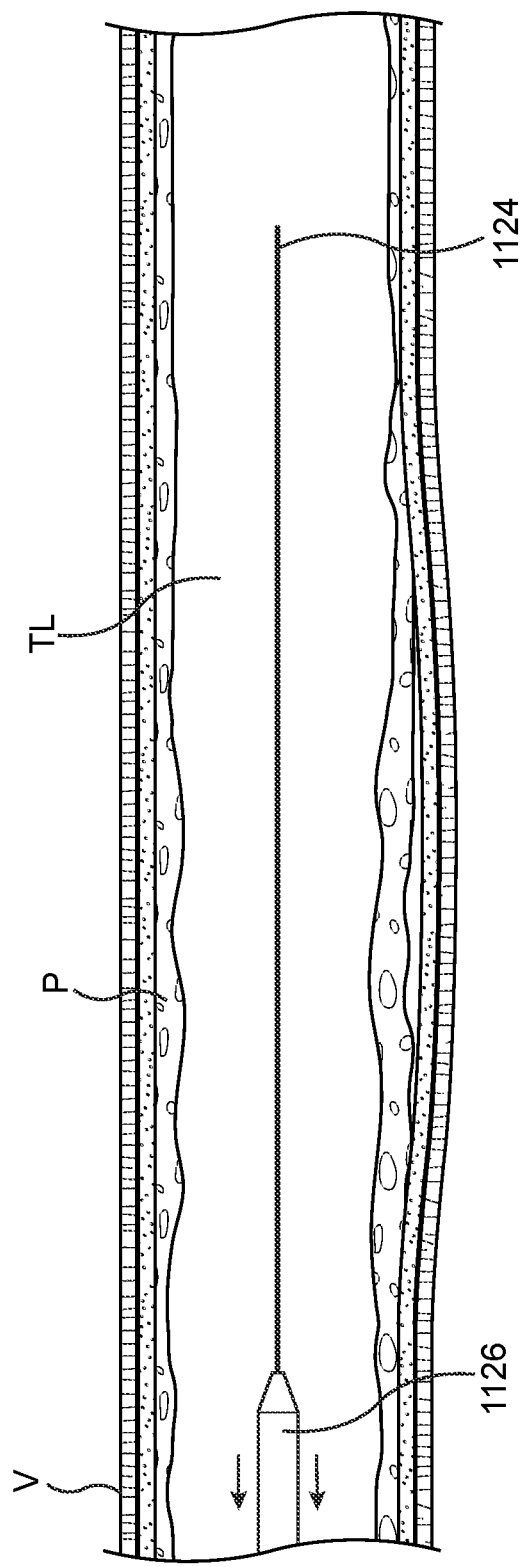
Figure 11A:
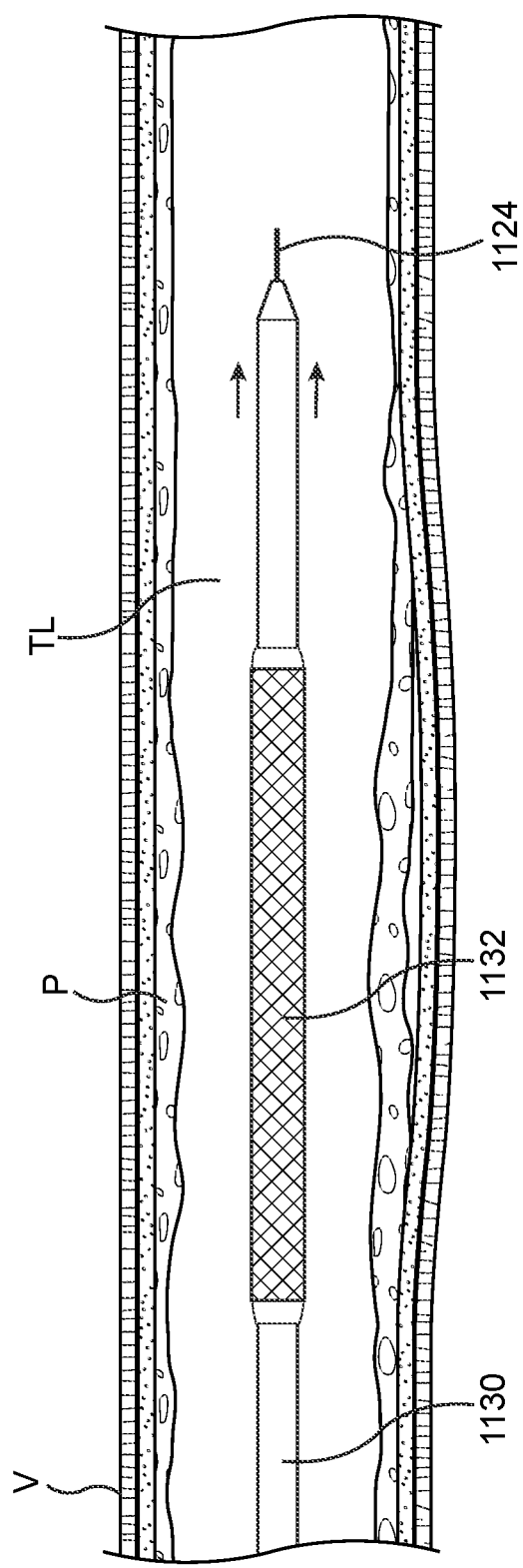
Figure 11A:
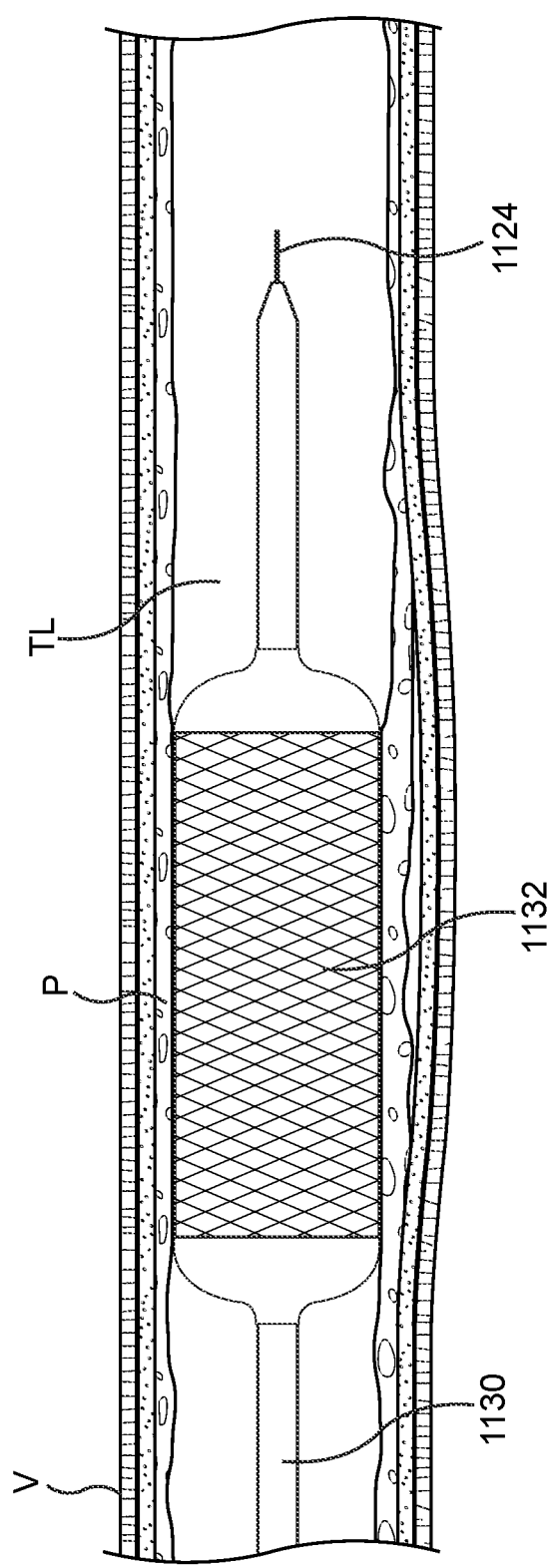
Figure 11A:
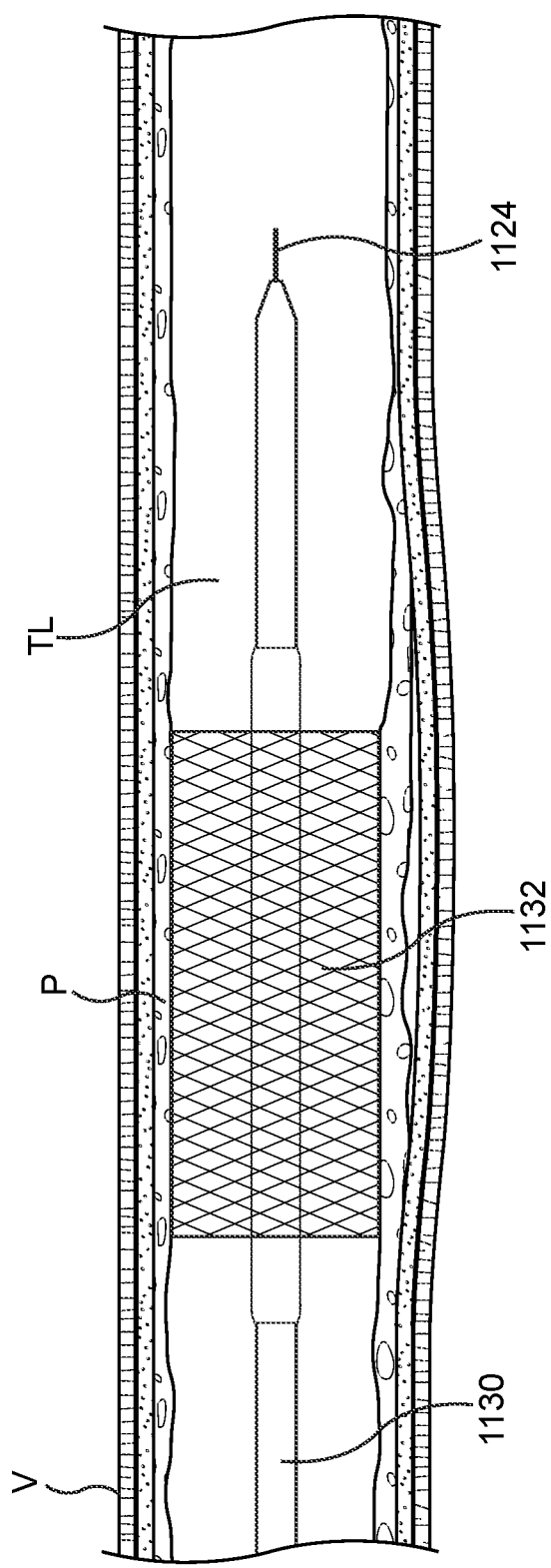
Figure 11A:
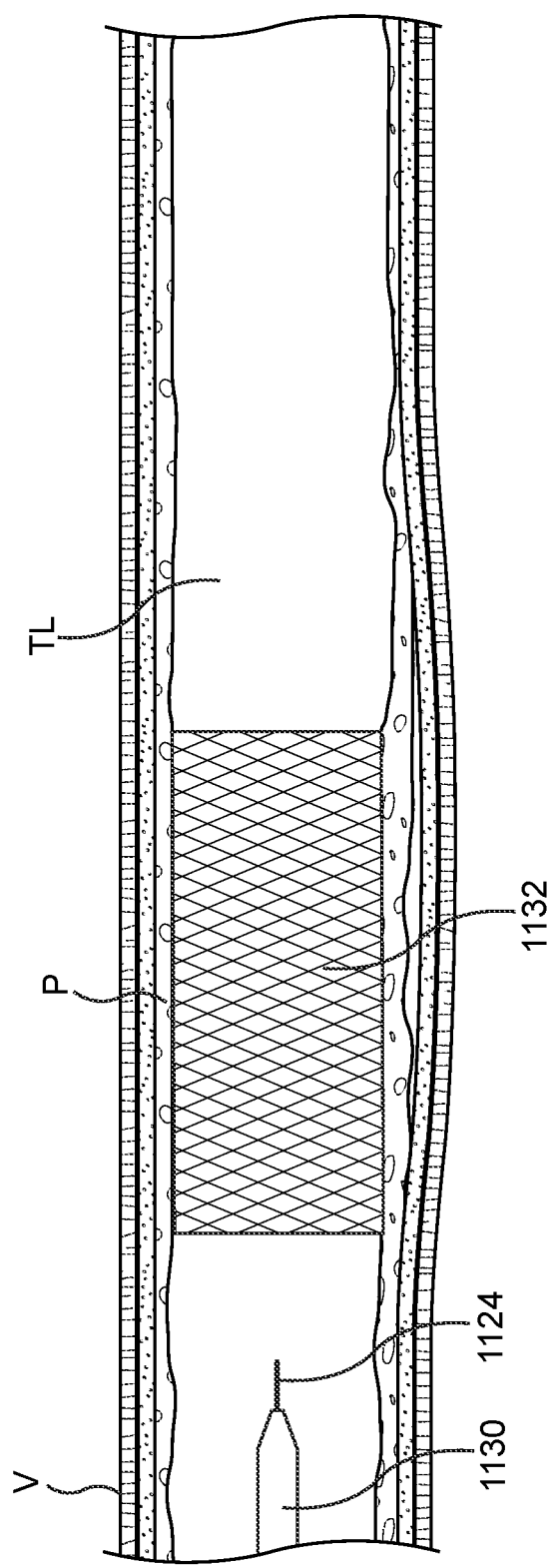

FIG. 11Z shows that after the re-entry wire 1120 has been advanced distally to a desired distal position in the true lumen TL, the balloon or other expandable member 1112 may be collapsed releasing the anchoring of the distal portion of the catheter 1110.

FIG. 11AA shows proximal retraction of the re-entry catheter 1110 to remove the catheter 1110 from the false lumen or pocket 1108 while the re-entry wire 1120 remains in position.

In FIG. 11AB, the re-entry catheter 1110 is further retracted proximally so that the catheter is removed from the pocket 1108 and eventually removed from the patient.

FIG. 11AC shows that once the re-entry catheter 1110 is removed from the vessel V and the patient, only the re-entry wire 1120 remains in place. Here, the re-entry wire passes through the blood vessel V, travels past the occlusive plaque P in the subintimal space 1108, and finally exits the subintimal space and re-enters the true lumen TL of the blood vessel distal of the occlusive plaque P. Now, a path exists across the obstructive plaque and this will allow a therapeutic catheter such as an angioplasty catheter or stent deliver system to be delivered to the treatment site. In some situations, the stick and swab method may be used where a stiff re-entry wire is used to re-enter the true lumen and then it may be replaced with another wire having desired mechanical properties (e.g. a softer wire) to avoid damage to the vessel and surrounding tissue.

FIG. 11AD shows an optional step where a microcatheter or other wire exchange catheter 1122 is advanced distally over the re-entry wire 1120.

FIG. 11AE illustrates continued distal advancement of the microcatheter or other wire exchange catheter 1122 over the re-entry wire 1120 so that the microcatheter is advanced through the subintimal space or pocket 1108 created by the knuckling wire earlier, and past the occlusive plaque P where the microcatheter then re-enters the true lumen TL.

FIG. 11AF shows that after the microcatheter or wire exchange catheter 1122 has been properly positioned, the re-entry wire 1120 may be proximally retracted through the wire exchange catheter 1122 and removed from the patient. The re-entry wire may then be replaced with a new guidewire that has more desirable mechanical properties for the remainder of the procedure. The new guidewire may be referred to as a workhorse wire and may be less stiff than the re-entry wire and therefore be less traumatic and therefore safer to use.

FIG. 11AG shows the new workhorse guidewire 1124 disposed in the microcatheter or wire exchange catheter 1122 and exiting the distal end of the microcatheter 1122. Thus, the new workhorse guidewire 1124 extends through the vessel, crosses the occlusive plaque P by passing through the subintimal space created by the knuckling wire and then re-enters the true lumen distal of the occlusive plaque P.

FIG. 11AH illustrates removal of the microcatheter or other wire exchange catheter 1122. After the new workhorse guidewire 1124 has been positioned, the microcatheter or other wire exchange catheter 1120 is proximally retracted over the new workhorse guidewire 1124.

FIG. 11AI show further proximal retraction of the microcatheter 1122 pulls the microcatheter proximally so that it passes under the occlusive plaque P via subintimal space 1108 and is removed from the patient.

Once the microcatheter is removed, FIG. 11AJ shows that an optional balloon angioplasty catheter 1126 may be advanced over the workhorse wire 1124 distally toward the occlusive plaque P. The balloon angioplasty catheter may optionally be a drug eluting balloon that delivers an antirestenosis drug to the treatment area. Examples of therapeutic agents are disclosed later in this application.

In FIG. 11AK the balloon catheter 1126 is advanced distally over the workhorse guidewire 1124 through the subintimal pocket 1108 and past the occlusive plaque P. The distal tip of the angioplasty catheter re-enters the true lumen of the blood vessel distal of the occlusive plaque. The angioplasty catheter is then positioned so that the balloon 1128 is disposed under the occlusive plaque P.

FIG. 11AL shows expansion of the balloon 1128 on the angioplasty catheter 1126 which compresses the occlusive plaque P and re-opens the lumen. If the balloon is a drug eluting balloon, the drug is delivered to the treatment site.

After balloon dilation has been completed, the balloon 1128 may be deflated as shown in FIG. 11AM.

In FIG. 11AN, after the balloon has been deflated, the angioplasty catheter 1124 may be proximally retracted over the workhorse guidewire 1124 and removed from the patient.

Optionally, FIG. 11AO shows that once the balloon catheter has been removed, a stent delivery system 1130 may be advanced over the workhorse guidewire 1124 to the treatment site. The stent delivery system is positioned so that the stent 1132 is aligned with the angioplastied plaque. The stent may be delivered through the true lumen of the vessel since lumen patency has been restored and delivery via the subintimal space is not required.

FIG. 11AP shows expansion of the stent 1132 to provide scaffolding that supports the vessel wall and the angioplastied plaque region which used to the occlusive plaque P. Optionally, the stent may carry a therapeutic agent that is eluted into the stenotic lesion to help prevent restenosis. Any of the therapeutic agents disclosed herein may be used in this example.

The balloon 1128 on the stent delivery catheter 1130 is deflated in FIG. 11AQ and the stent 1132 is left in place.

FIG. 11AR shows proximal retraction of the stent delivery catheter 1130 so that it is removed from the patient and the stent 1132 is left behind. In this example, the stent is balloon expandable, but in other examples a self-expanding stent may be used instead. In all cases it is intended that with one or more stents one connects the proximal true lumen to the distal true lumen, thus re-creating a luminal connection from the proximal to the distal vessel restoring antegrade blood flow.

FIGS. 11A-11AR show an example of a method using a re-entry catheter with the optional balloon. In some examples, the catheter may not have a balloon. The method of using a re-entry catheter such as the one described in FIGS. 1-9 but without a balloon is generally the same as previously described above in FIGS. 11A-11AR with the exception that the balloon is absent and therefore a balloon is never expanded or collapsed. FIGS. 22A-22D show major steps that are different when using a re-entry catheter without a balloon as compared to the method described in FIGS. 11A-11AR. Other aspects of the method are generally the same.

Figure 22A:
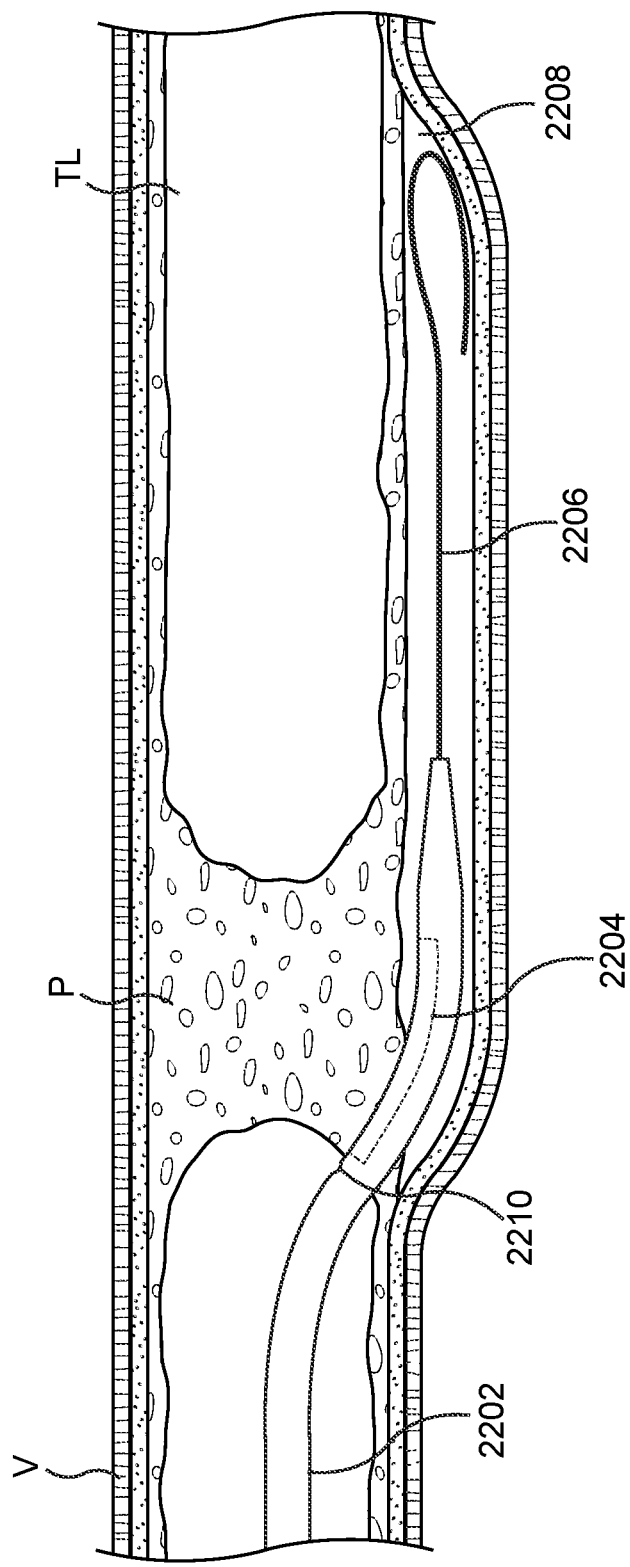
FIGS. 22A-22D show an example of a method of treating an obstruction in a vessel using a catheter without a balloon.

FIG. 22A shows that after the knuckling wire 2206 has been inserted into the vessel V and advanced subintimally past the occlusive plaque P through the pocket 2208 as previously described above, the re-entry catheter 2202 may be advanced over the knuckling wire and moved distally so that the re-entry catheter 2202 passes the occlusive plaque P subintimally through the pocket 2208. The re-entry catheter includes an ultrasound transducer 2204 for imaging the vessel and confirming the re-entry point of the re-entry wire. The re-entry catheter does not include a balloon.

Figure 22B:
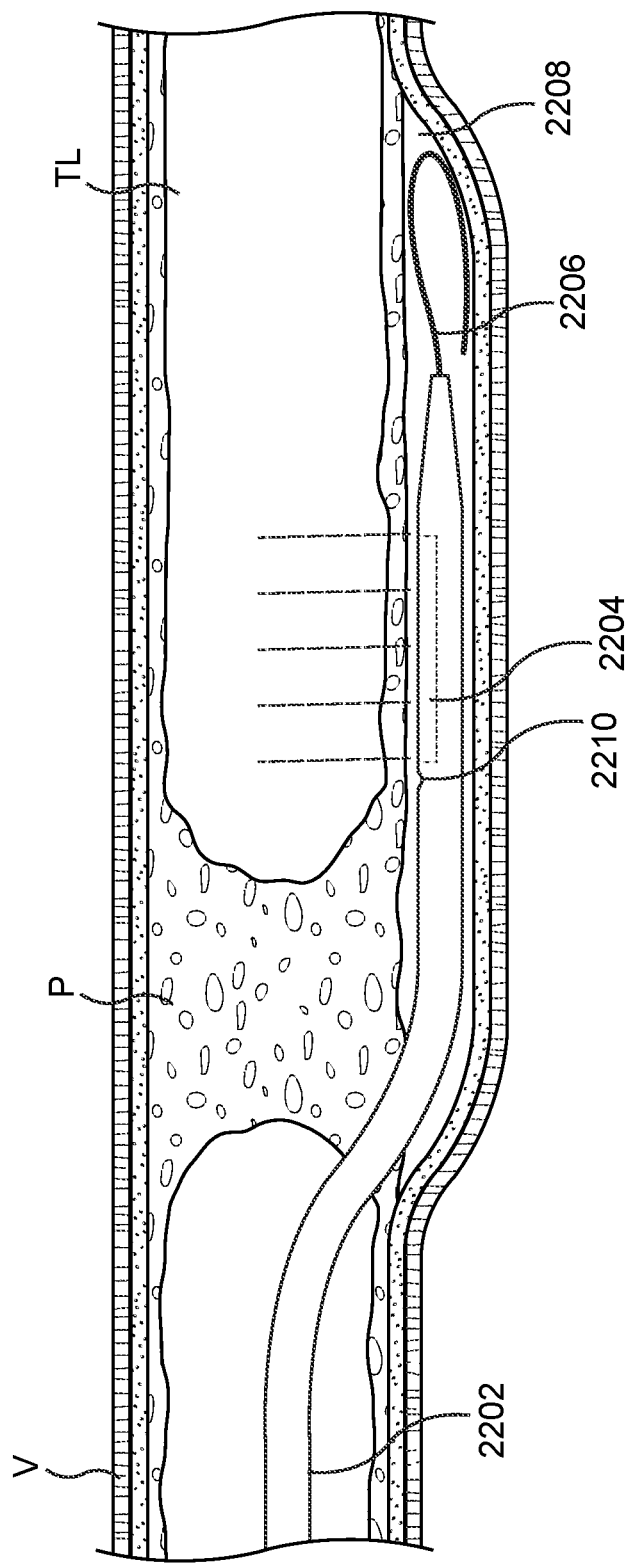

In FIG. 22B the re-entry catheter 2202 is advanced further distally until the ultrasound transducer 2204 is distal of the occlusive plaque P based on the operator's judgement. The transducer may be used to image the vessel and ensure that the re-entry port 2210 is also distal of the occlusive plaque P. The ultrasound transducer emits a beam of ultrasound at an angle relative to the longitudinal axis of the catheter and has been discussed previously above.

The re-entry port also has an exit angle that assures that the re-entry wire exits the re-entry port at a desired angle as previously discussed above. This ensures that the ultrasound beam will form an ultrasound image that can be used to visualize the vessel and ensure that the re-entry port will allow the re-entry wire to clear the plaque and re-enter the true lumen TL.

Figure 22C:
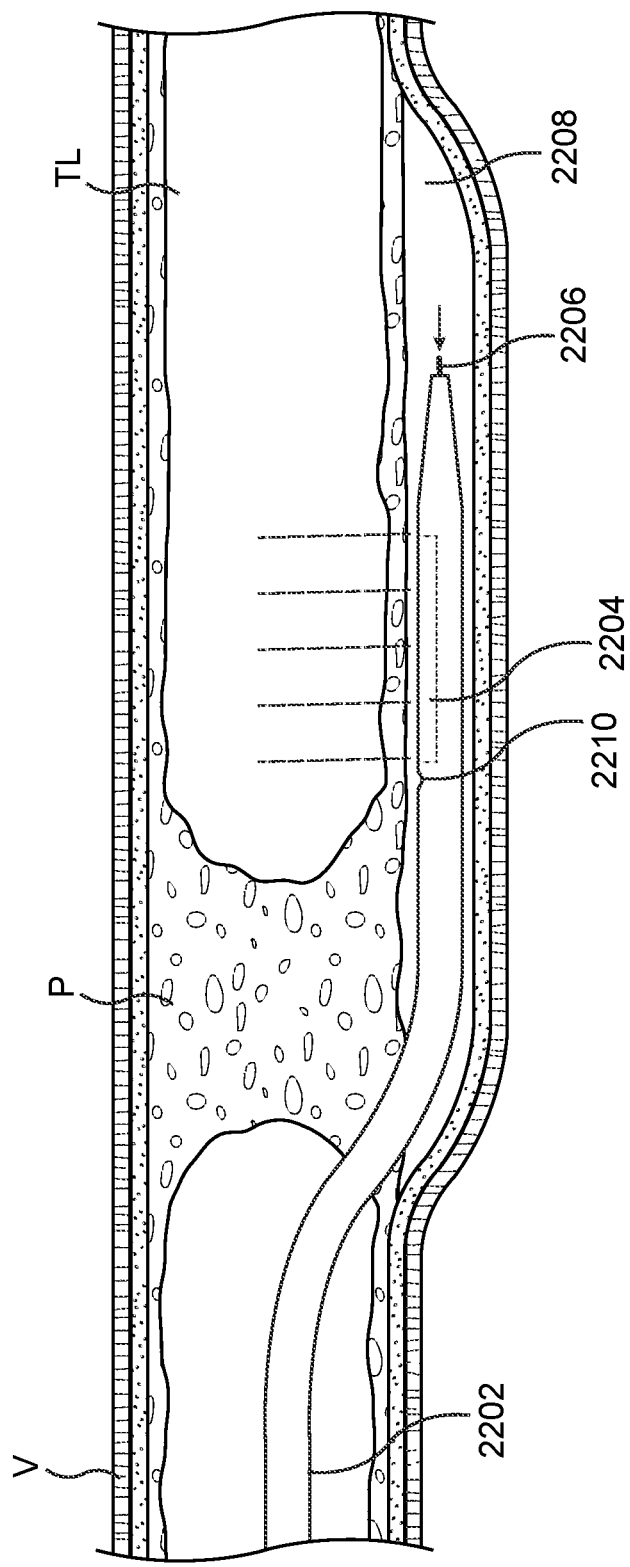

FIG. 22C shows that once the desired position of the re-entry catheter has been achieved to ensure that the re-entry wire will exit the re-entry port and re-enter the true lumen, the knuckling wire 2206 may be proximally retracted and removed from the re-entry catheter.

Figure 22D:
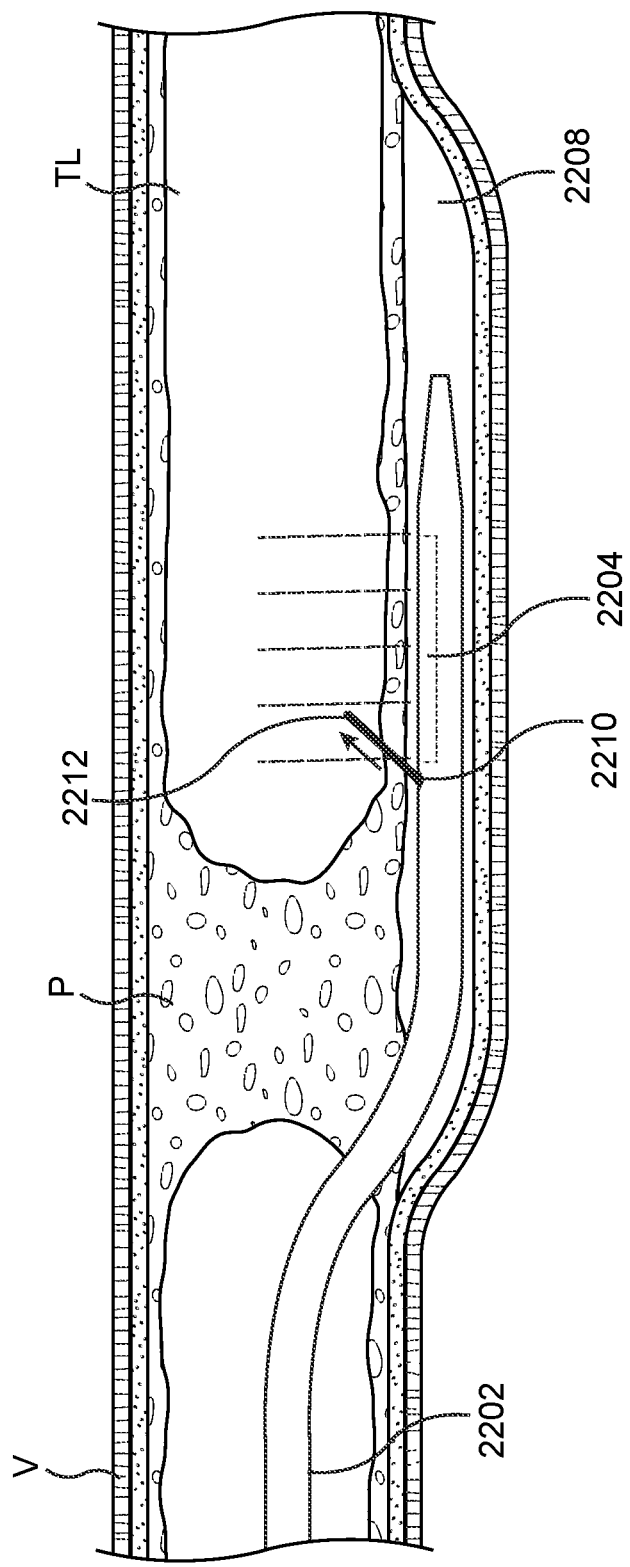

FIG. 22D shows advancement of the re-entry wire 2212 through the lumen that has been cleared of the knuckling wire and advanced distally until the re-entry wire 2212 exits the re-entry port 2210. The re-entry wire exits the re-entry port at any of the angles previously described above and the ultrasound beam similarly is emitted at any of the angles previously disclosed above ensuring that the region of the vessel in the image formed by the ultrasound transducer will be the same region into which the re-entry wire re-enters the true lumen TL. Since there is no balloon in this example, there is no inflation of the balloon to anchor the catheter. As before, if the re-entry catheter requires additional positioning, it may be advanced or retracted axially, or it may be rotated in order to obtain the desired orientation.

Once the re-entry wire has been properly delivered, it may be used to deliver an angioplasty catheter and/or a stent delivery catheter to treat the occluded vessel as previously described in FIGS. 11A-11AR. In this example or any example of the method of use, the re-entry wire may be replaced with a workhorse wire which is better suited to delivery of a therapeutic catheter such as an angioplasty catheter or stent delivery catheter. Optional replacement of the knuckling wire with a workhorse wire is described below in FIGS. 21A-21X. Other aspects of this example of using a re-entry catheter are generally the same as previously described above.

Re-Entry Device Example 2

The previous examples include a single common lumen used to slidably receive the guidewire (also referred to as a delivery guidewire or delivery wire) and the re-entry wire sequentially one after the other. In some situations, it may be advantageous to provide a catheter that has a separate lumen for the delivery guidewire and a separate lumen for the re-entry wire.

FIG. 12 show an example of a catheter used to introduce a re-entry wire and that has separate lumens for the delivery guidewire and re-entry wire. The catheter 1202 includes an elongate shaft having a distal end 1204 and a proximal end 1206. Adjacent the distal end 1204 of the catheter, there may be a tapered distal tip to facilitate delivery of the catheter through the blood vessel and that also provides an atraumatic tip that prevents tissue damage. The distal tip may include a distal port through which a guidewire may pass or through which fluid may be infused or aspirated. The re-entry wire port 1208 is also on a distal portion of the catheter along with an optional expandable member 1210 such as a balloon, which may be disposed on a side opposite of the re-entry port. The catheter also includes an ultrasound transducer (best seen in FIG. 13). The proximal end 1206 of the elongate shaft is coupled with a connector hub 1224, and an optional strain relief 1214 may be included to prevent unwanted wear and tear on the elongate shaft (e.g. kinking).

Here, the connector hub 1224 has four fingers in order to accommodate the various lumens and electrical cables in the catheter. A first finger 1218 on the hub allows the electrical cable 1216 to be connected with a connector that can be releasably or fixedly be coupled to other electrical cables or equipment such as an ultrasound imaging system, electrical power, or a screen for viewing the image. Cable 1216 is electrically coupled with the ultrasound transducer to provide power to the transducer and to transmit the ultrasound signal back to the ultrasound equipment so that it may be processed into an image which can be viewed by the physician or operator. The three other fingers may include connectors such as Luer connectors which allow the two lumens and the optional inflation lumen (when there is a balloon) to be releasably coupled with other tubing, equipment, inflation devices, etc. For example, the second finger 1220 may be fluidly coupled with either the guidewire lumen which allows a guidewire to exit the distal port, or the second finger may be fluidly coupled with the re-entry lumen which allows a re-entry wire to exit the re-entry port 1208. The third finger 1222 may be fluidly coupled to the other of the guidewire lumen or the re-entry lumen, depending on what the second finger is coupled to. The fourth finger 1226 may be fluidly coupled to an inflation lumen in the catheter that allows the optional balloon to be inflated and deflated. In the example where there is no balloon, the connector hub would only have three fingers since no inflation lumen is needed.

FIG. 13 highlights the distal portion of the catheter 1202 circled in phantom in FIG. 12. Here, the distal port 1230 is visible and this allows a guidewire (may also be referred to as a delivery guidewire or delivery wire, throughout this application) that passes through guidewire lumen 1232 to exit the distal end of the catheter. Thus the distal port is fluidly coupled with the guidewire lumen. Additionally, the re-entry wire port 1208 is also more clearly visible and this allows a re-entry wire that passes through the re-entry wire lumen 1236 to exit the catheter through the re-entry wire port 1208. Thus, the re-entry port is fluidly coupled with the re-entry wire lumen. The ultrasound transducer 1234 coupled to the catheter is also visible in this view. The guidewire lumen is separate and discrete from the re-entry wire lumen and they do not fluidly communicate with one another. Other aspects of FIG. 13 are the same as in FIG. 12.

Figure 14:
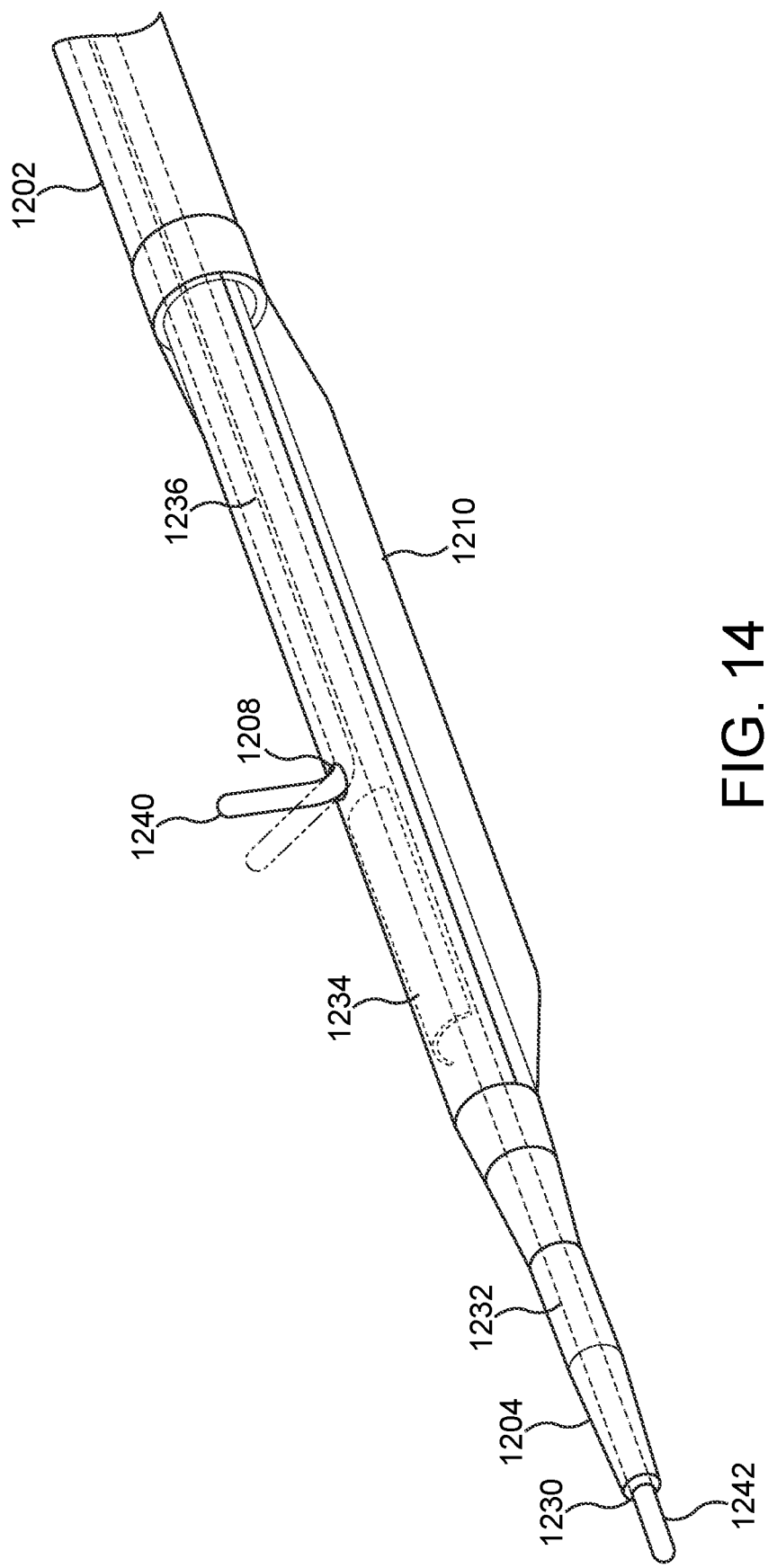
FIG. 14 is a perspective view of a distal portion of the catheter in FIG. 12.

FIG. 14 shows a perspective view of the distal portion of the catheter 1202 in FIG. 12. FIG. 14 is the same as FIG. 13 with the exception that the guidewire 1242 is shown disposed in the guidewire lumen 1232 and partially exiting the distal port 1230. Similarly, re-entry wire 1240 is shown in re-entry wire lumen 1236 and partially exiting re-entry wire port 1208. As discussed previously, the re-entry wire 1240 may have a straight or curved tip and when the curved tip is rotated, this will steer the distal tip into a different position as shown the by the re-entry wire shown in phantom. Here, it is clear that the catheter 1202 has a separate lumen for the guidewire and a separate lumen for the re-entry wire, therefore both wires may be disposed in the catheter simultaneously, unlike the previous example where there is only a single lumen that accommodates the guidewire and re-entry wire so that only one wire may be disposed in the catheter at a time. In this example the delivery guidewire lumen may be an over the wire (OTW) lumen or a rapid exchange (RX) lumen, and similarly the re-entry wire lumen may be an over the wire lumen or a rapid exchange lumen. Thus, any of the four possible combinations of RX and OTW lumens are possible. As discussed previously, an over the wire lumen has a distal port and a proximal port that is closer to the proximal end of the catheter than the distal end of the catheter. And a rapid exchange catheter also has a distal port and a proximal port, but here the proximal port is closer to the distal end of the catheter than the proximal end of the catheter. These configurations will be discussed further later on in this specification.

Figure 15:
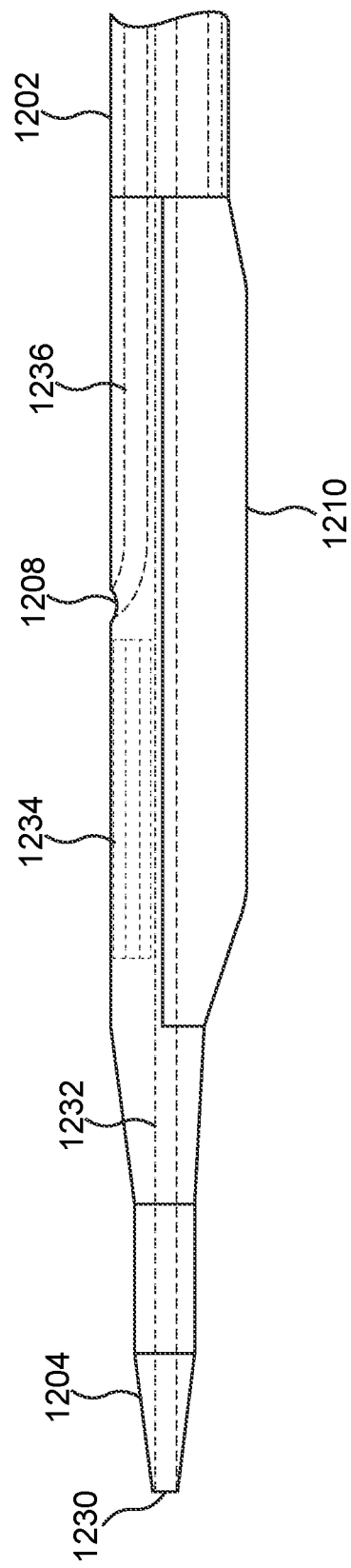
FIG. 15 is a side view of a distal portion of the catheter in FIG. 12.

FIG. 15 shows a side view of the distal portion of the catheter seen in FIGS. 12-14 but with the guidewire and re-entry wires removed from the catheter. The ultrasound transducer may be a phased array which is partially or fully disposed circumferentially around the catheter. The ultrasound transducer may provide a beam that images a sector of any size, for example an arc of greater than 0 degrees up to 360 degrees, or greater than 0 degrees to 180 degrees, or 10 degrees to 180 degrees, or any range between 0 degrees and 360 degrees.

The ultrasound transducer images the blood vessel and has an imaging axis that may be any angle relative to the longitudinal axis of the catheter such as 0 degrees to 180 degrees. For example, the ultrasound beam angle may be 90 degrees. An ultrasound imaging axis angle of 0 to less than 90 degrees is distally facing, while an angle of 90 degrees is perpendicular to the longitudinal axis of the catheter (or side firing), and an angle of greater than 90 degrees up to 180 degrees is proximally facing. In any example, the ultrasound angle may be from 0 degrees to 135 degrees. The ultrasound beam angle allows an ultrasound image to be obtained that not only shows the anatomy around the re-entry point of the vessel, but also shows the re-entry point where a re-entry wire exits the subintimal space and re-enters the vessel true lumen and shows the re-entry wire as it is advanced distally, thereby allowing the operator to observe the re-entry wire to ensure that it is properly advanced and does not puncture the vessel or propagate the dissection that was used to create the subintimal pocket.

In other examples, the ultrasound transducer may be a flat planer ultrasound transducer coupled to the catheter. Other aspects of the transducer may take the form of the transducer previously described above, including the rotational ultrasound transducer. Optionally in this example or any example disclosed herein, the catheter may include a marker either radiopaque or echogenic that allows the operator to see where the re-entry port is relative to the native anatomy and other features on the catheter using either ultrasound or fluoroscopy. Additional details about markers are disclosed below. Other aspects of FIG. 15 are generally the same as in FIGS. 13-14.

Figure 16:
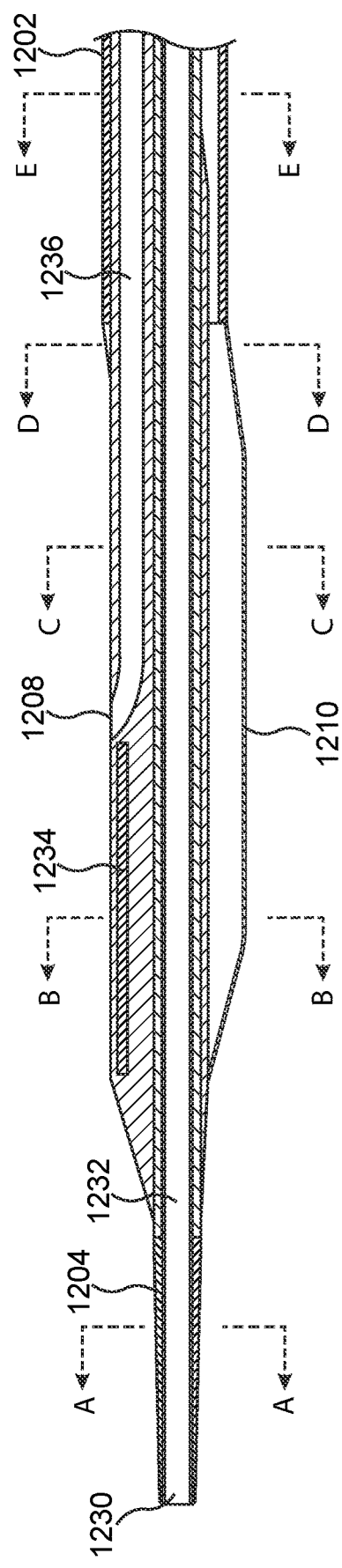
FIG. 16 is a cross-section of a distal portion of the catheter in FIG. 12.

FIG. 16 shows a cross-section of the catheter 1202 from FIGS. 12-15 without the guidewire or re-entry wire disposed in their respective lumen. The guidewire lumen 1232 may be formed from a separate tube in the catheter or it may be integrally formed as a lumen in the catheter tubing during extrusion. Similarly, the re-entry wire lumen 1236 may be a separate tube in the catheter or it may be a lumen integrally formed in the catheter during extrusion. Other aspects of FIG. 16 are generally the same as previously described above with respect to FIGS. 12-15.

FIGS. 17A-17E show various cross-sections taken along the longitudinal axis of catheter 1202 in FIG. 16.

FIG. 17A shows a cross-section taken along the line A-A in FIG. 16 and shows the distal tip of the catheter with guidewire lumen 1232 formed in tube 1702 (which may be a microliner) and surrounded by an outer tube 1704 or material which may form the tapered distal portion of the catheter.

FIG. 17B shows a cross-section taken along the line B-B in FIG. 16 and includes the features of FIG. 17A as well as the optional expandable member 1210 which in this example is a balloon, as well as ultrasound transducer 1234. In other examples, the optional balloon may be replaced with any of the other examples of expandable members disclosed herein. The ultrasound transducer may be a phased array that partially or fully circumferentially wraps around the catheter, or it may be flat planer transducer coupled to the catheter. Additional aspects of the ultrasound transducer have previously been disclosed above. Adhesive or another tube or material 1706 is used to fill the spaces between tubing and other components and hold them in a desired orientation, as well as providing desired mechanical properties to the catheter.

FIG. 17C is a cross-section of the catheter in FIG. 16 taken along the line C-C. Here, FIG. 17C includes all of the features of FIG. 17B except the ultrasound transducer and also includes electrical cable 1708 that is coupled with the transducer, as well as including re-entry lumen 1710. The electrical cable 1708 may be disposed in a separate lumen in the catheter, or the cable may be co-extruded with the catheter and be integral with the catheter. Re-entry lumen 1710 may be a separate tube that is disposed in the catheter, or the lumen may be formed integrally with the catheter during extrusion.

FIG. 17D is a cross-section of the catheter in FIG. 16 taken along the line D-D. FIG. 17D includes all of the features of FIG. 17C except the balloon, but also shows when the optional balloon is included with the catheter, the inflation balloon inflation lumen 1712 may be crescent shaped and is formed in the annular space between the outer tube of the catheter and the inner tubes, or the inflation lumen may be formed as a separate integral lumen with the catheter. Additionally, optional braiding 1714 may be included in the outer catheter shaft in order to provide desired mechanical properties to the catheter, such as pushability, torquability, kink resistance, etc.

FIG. 17E is a cross-section taken along the line E-E in FIG. 16. All of the features of FIG. 17D are included in FIG. 17E with the major difference being that the crescent shaped inflation lumen 1712 transitions into a full circular lumen. Other aspects of FIG. 17E are generally the same as in FIG. 17D.

Figure 18:
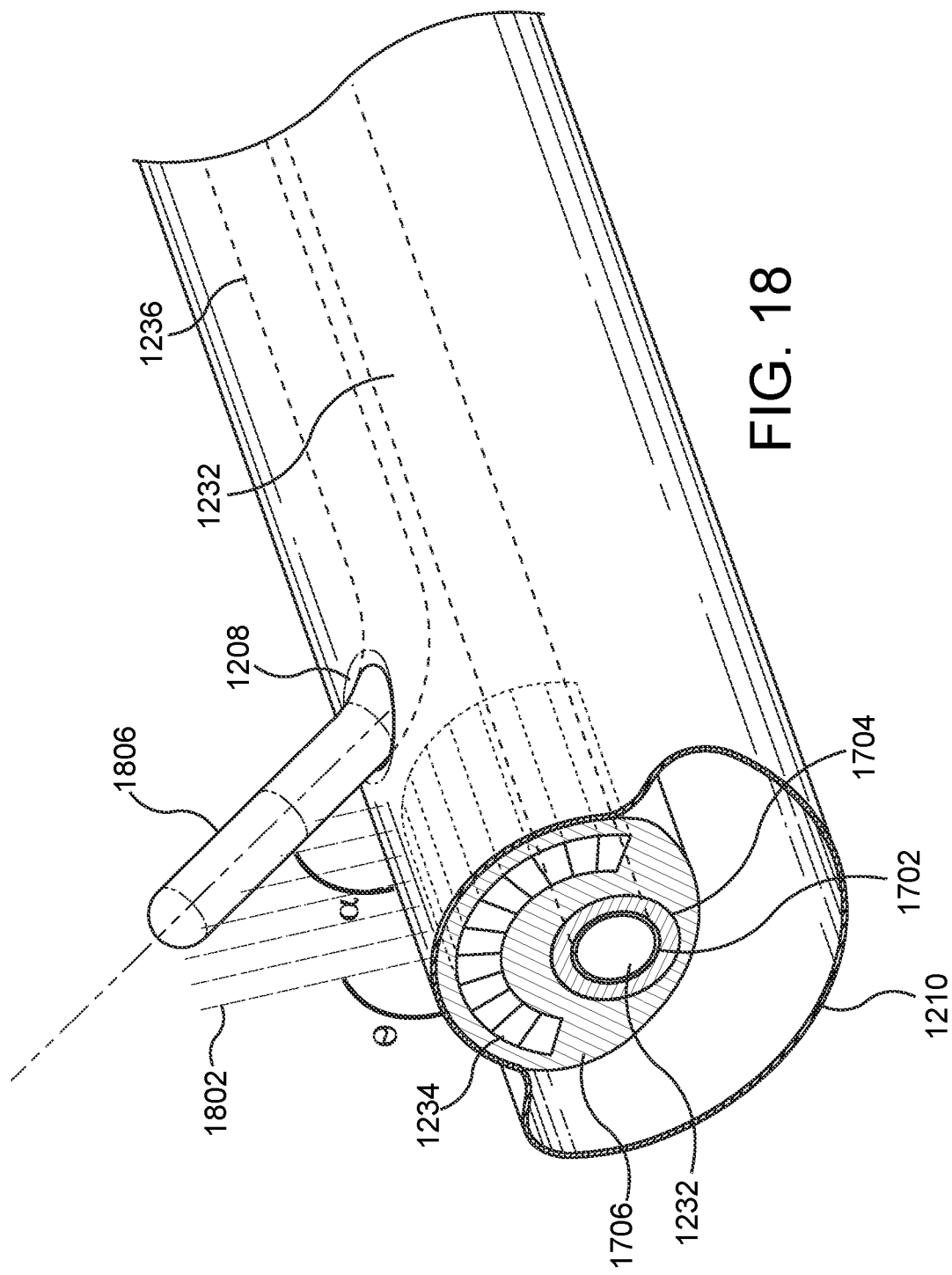
FIG. 18 shows a perspective cross-section of a distal portion of the catheter in FIG. 12.

FIG. 18 shows a perspective view of a portion of the distal end of the catheter 1202 in FIG. 12. Here, the optional balloon 1210 is shown partially circumferentially disposed around the catheter and ultrasound transducer 1234 is also partially circumferentially disposed around the catheter, although the transducer may be fully circumferentially disposed around the catheter or a flat planar transducer. Similarly, the balloon may optionally be fully circumferentially disposed around the catheter. Here, re-entry wire 1806 is shown disposed in re-entry lumen 1236 and extending out of re-entry port 1208 at a re-entry angle relative to the longitudinal axis of the catheter, angle alpha. The re-entry angle alpha may take the same form as previously discussed above, and therefore may be distally facing, where angle alpha is between 0 and 90 degrees, or the wire may exit orthogonally to the longitudinal axis of the catheter at 90 degrees, or the wire may exit proximally facing at an angle alpha of greater than 90 to 180 degrees. Thus, the re-entry wire angle alpha may be any desired angle but, in some examples, may be between 0-90 degrees, or between 60-80 degrees, and in other examples may be 30 degrees, 45 degrees, or 60 degrees.

Similarly, the ultrasound beam 1802 exits the transducer at an angle theta which may take the same form as previously discussed above. Thus, in this example, the ultrasound transducer may provide a beam that images a sector of any size, for example an arc of greater than 0 degrees up to 360 degrees, or greater than 0 degrees to 180 degrees, or 10 degrees to 180 degrees, or any range between 0 degrees and 360 degrees. The ultrasound transducer images the blood vessel and has an imaging axis that may be any angle theta relative to the longitudinal axis of the catheter such as 0 degrees to 180 degrees. For example, the angle theta may be 90 degrees. An ultrasound imaging axis angle theta of 0 to less than 90 degrees is distally facing, while an angle theta of 90 degrees is perpendicular to the longitudinal axis of the catheter (or side firing), and an angle theta of greater than 90 degrees up to 180 degrees is proximally facing. The ultrasound beam angle allows an ultrasound image to be obtained that not only shows the anatomy around the re-entry point of the vessel, but also shows the re-entry point where a re-entry wire exits the subintimal space and re-enters the vessel true lumen and shows the re-entry wire as it is advanced distally, thereby allowing the operator to observe the re-entry wire to ensure that it is properly advanced and does not puncture the vessel or propagate the dissection that was used to create the subintimal pocket. Top and side views of FIG. 18 are substantially the same as shown in FIG. 17A-17B with the exception that there would be two lumens instead of the single common lumen. Other aspects of the catheter are generally the same as previously discussed above in FIGS. 12-17B.

In this example, there is only a single re-entry wire exit port. However, in this example or any example, the re-entry catheter may have multiple re-entry wire exit ports. This may help the operator guide the re-entry wire to a desired re-entry position by selecting an exit port that is more appropriate. Additional details about multiple re-entry ports that may apply to any example of a re-entry catheter disclosed herein, are discussed below.

Examples of Hubs

Figure 19:
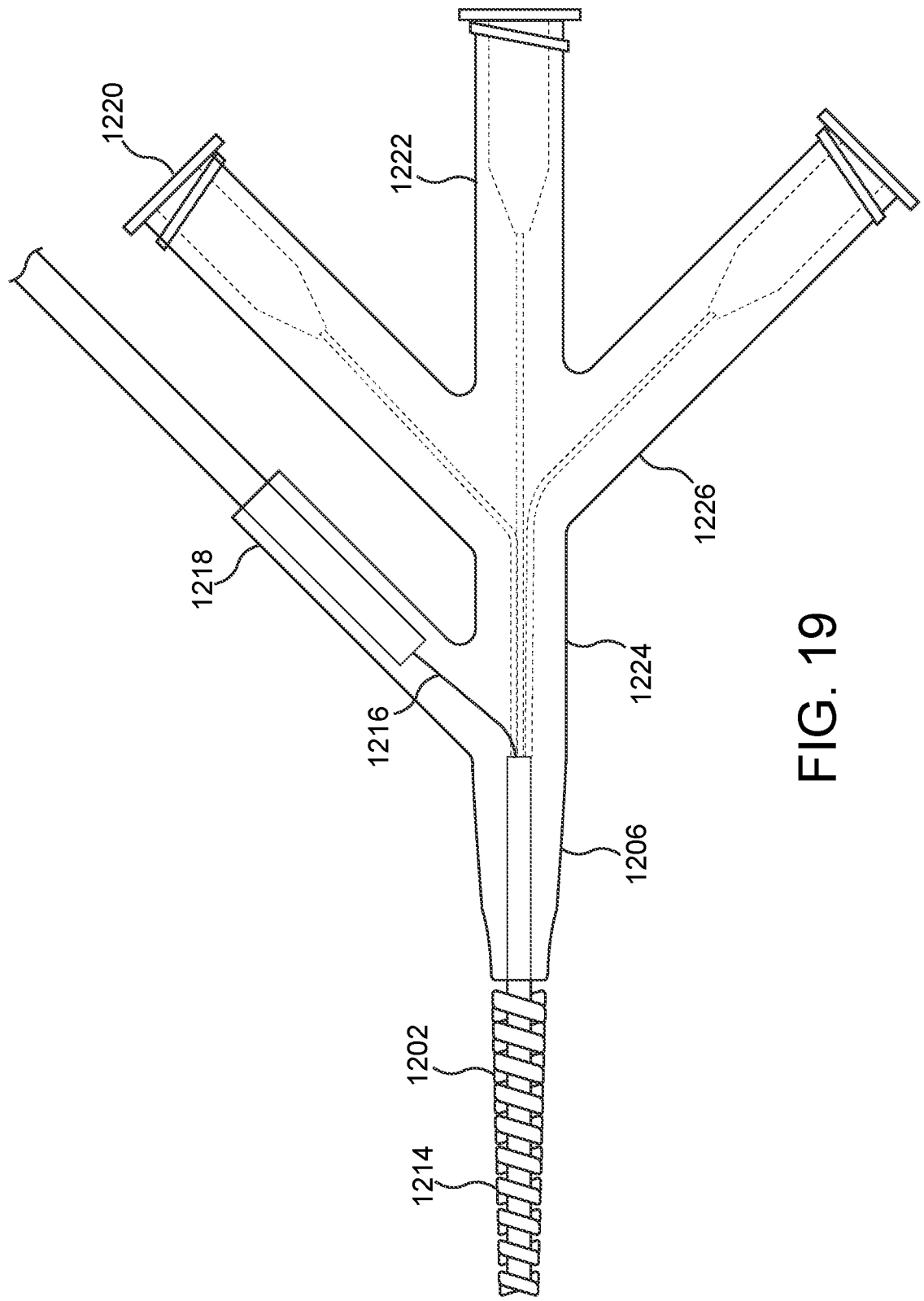
FIG. 19 shows an example of a proximal end of the catheter in FIG. 12.

FIG. 19 illustrates an example of a proximal end of the catheter in FIG. 12 when the catheter includes the optional balloon. The catheter therefore includes an electrical cable, a guidewire lumen, a re-entry wire lumen, and a balloon inflation lumen. Therefore, the proximal end of the catheter may be coupled with a connector hub having four fingers. Each finger may have a connector for releasably coupling the electrical cable or lumen in that finger with additional equipment such as tubing, a balloon inflation device, or other parts of a system.

The proximal end 1206 of the catheter 1202 is coupled with a connector hub 1224, and an optional strain relief 1214 may be included to prevent unwanted wear and tear on the catheter (e.g. kinking). Here, the connector hub 1224 has four fingers. A first finger 1218 on the hub allows the electrical cable 1216 to be joined to a connector that may be releasably or fixedly connected to other electrical cables or equipment such as ultrasound imaging machine or a screen for viewing the image. Cable 1216 is electrically coupled with the ultrasound transducer to provide power to the transducer and to transmit the ultrasound signal back to the ultrasound equipment so that it may be processed into an image which can be viewed by the physician or operator. The three other fingers may include connectors such as Luer connectors which allow the two lumens and the optional inflation lumen (when there is a balloon) to be releasably coupled with other tubing, equipment, inflation devices, etc. For example, the second finger 1220 may be fluidly coupled with either the guidewire lumen which allows a guidewire to exit the distal port, or the second finger may be fluidly coupled with the re-entry lumen which allows a re-entry wire to exit the re-entry port 1208. The third finger 1222 may be fluidly coupled to the other of the guidewire lumen or the re-entry lumen, depending on what the second finger is coupled to. The fourth finger 1226 may be fluidly coupled to an inflation lumen in the catheter that allows the optional balloon to be inflated and deflated. When there is no balloon, the connector hub would only have three fingers since no inflation lumen is needed, as will be illustrated next.

Figure 20:
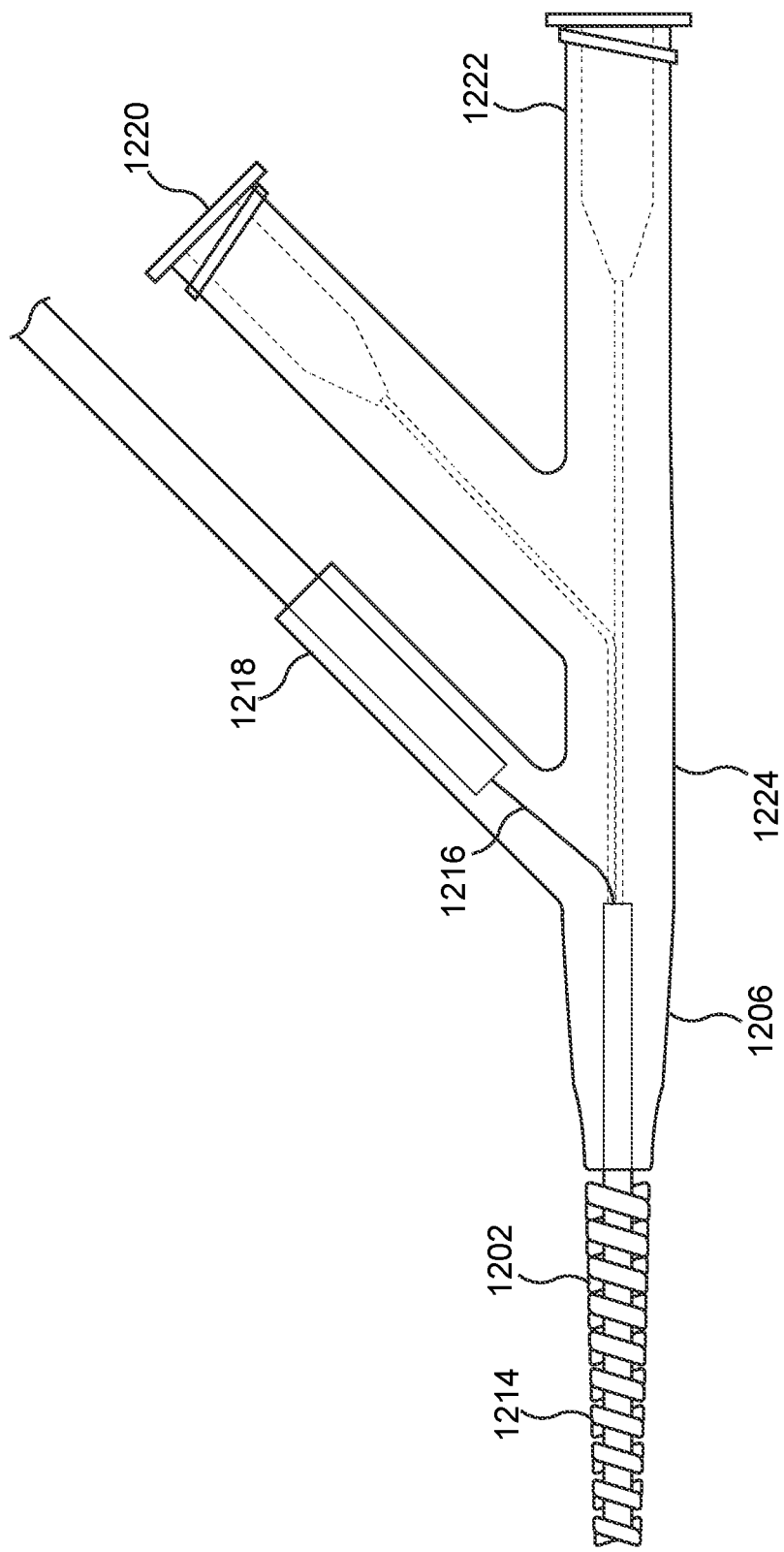
FIG. 20 shows another example of a proximal end of the catheter in FIG. 12.

FIG. 20 shows an example of a proximal connector hub 1224 that is generally the same as the hub in FIG. 19 but without a fourth finger since there is no balloon and hence no inflation lumen. Other aspects of FIG. 20 are substantially the same as FIG. 19 where there is optional braiding for a strain relief 1214, a connector finger 1218 for the electrical wire 1216, and two connector fingers 1220, 1222 for the guidewire lumen and the re-entry wire lumen. Either finger may accommodate either lumen. In the examples of FIGS. 19-20, because the proximal ports are disposed at the proximal-most end of the catheter, these configurations are over the wire configurations, however as previously disclosed, either rapid exchange or over the wire configurations are contemplated and will be illustrated below.

Example of Method

Figure 21A:
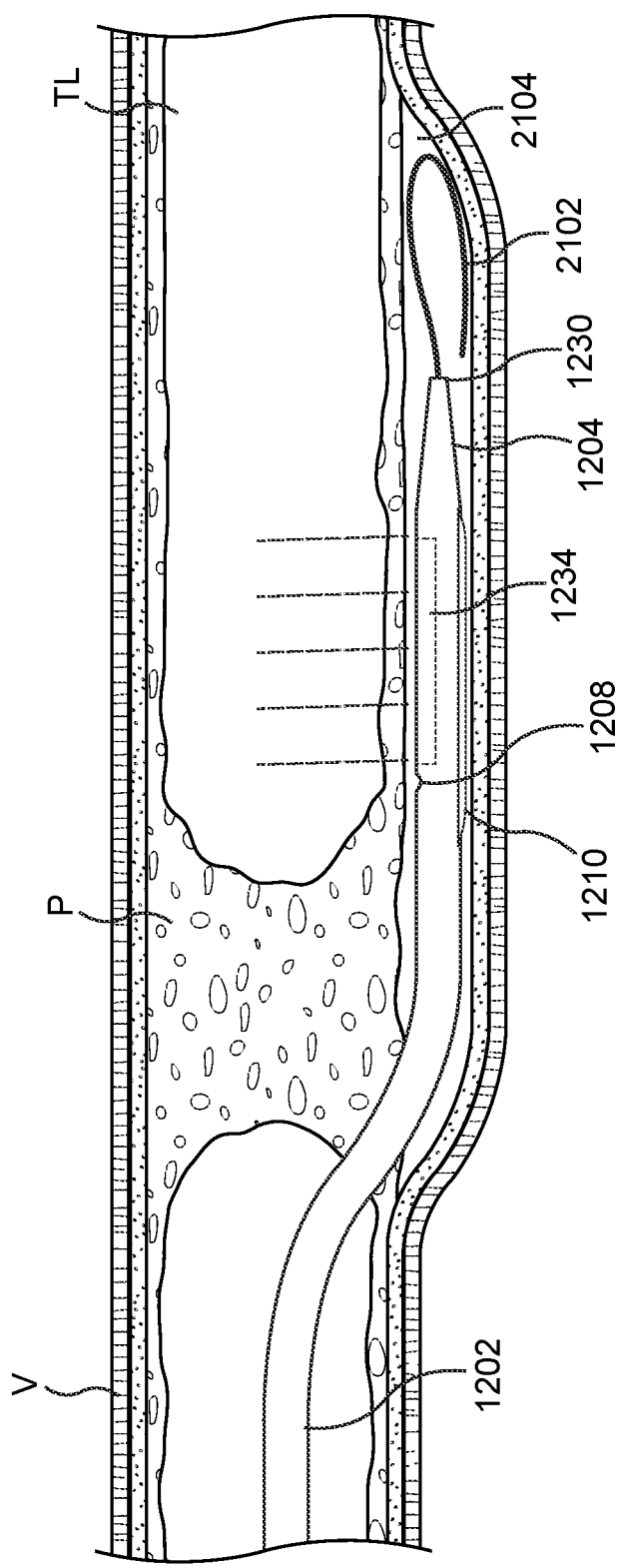
FIGS. 21A-21X show another example of a method of treating an obstruction in a vessel.
Figure 21B:
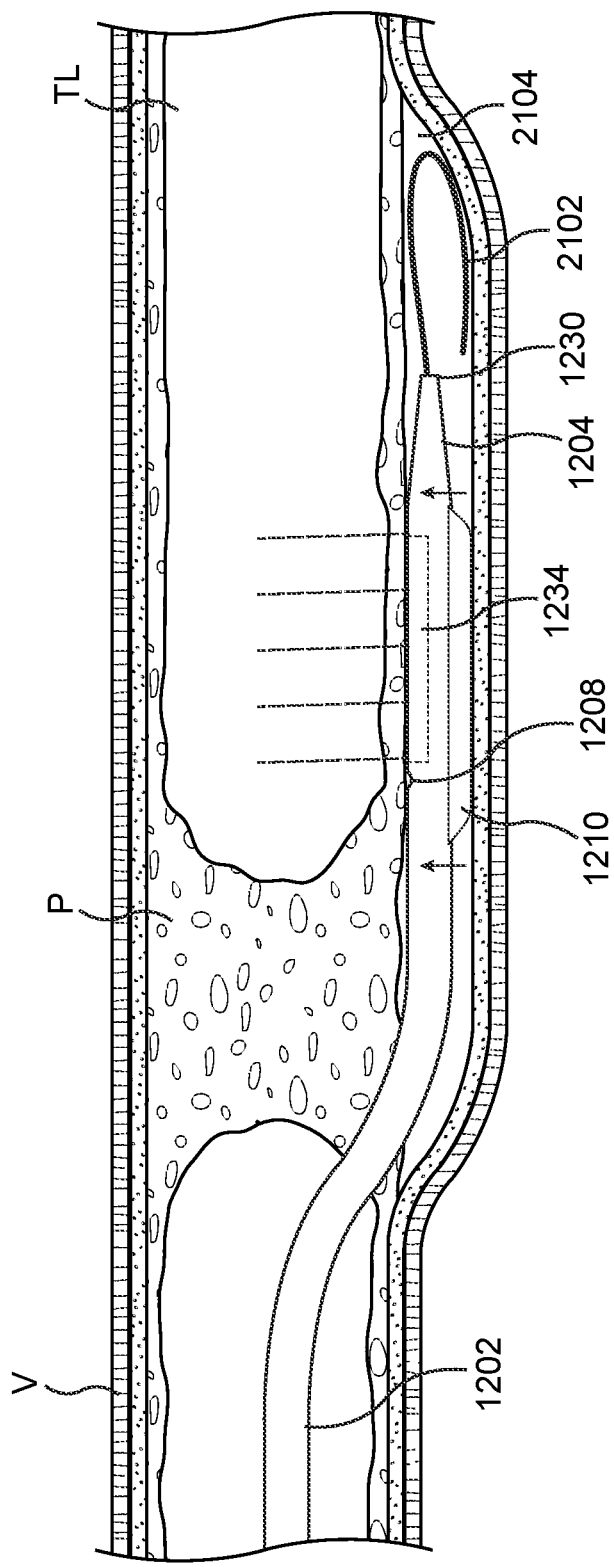
Figure 21C:
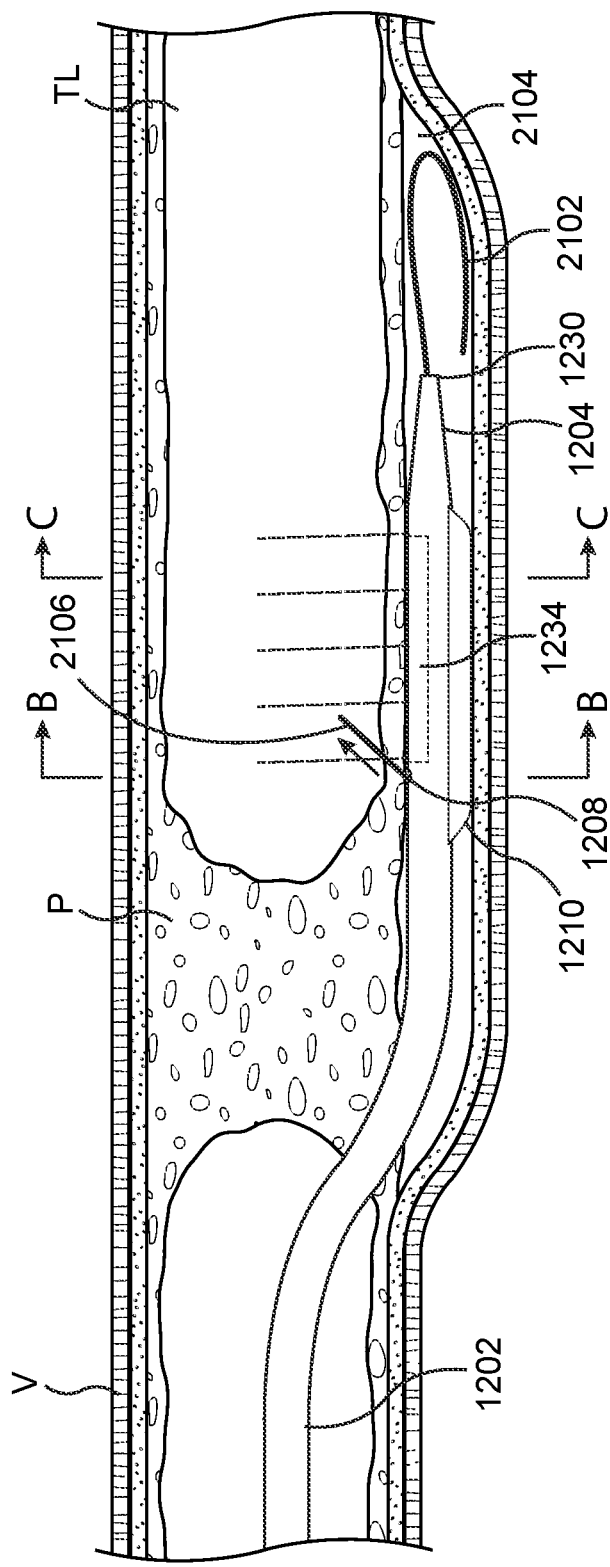
Figure 21E:
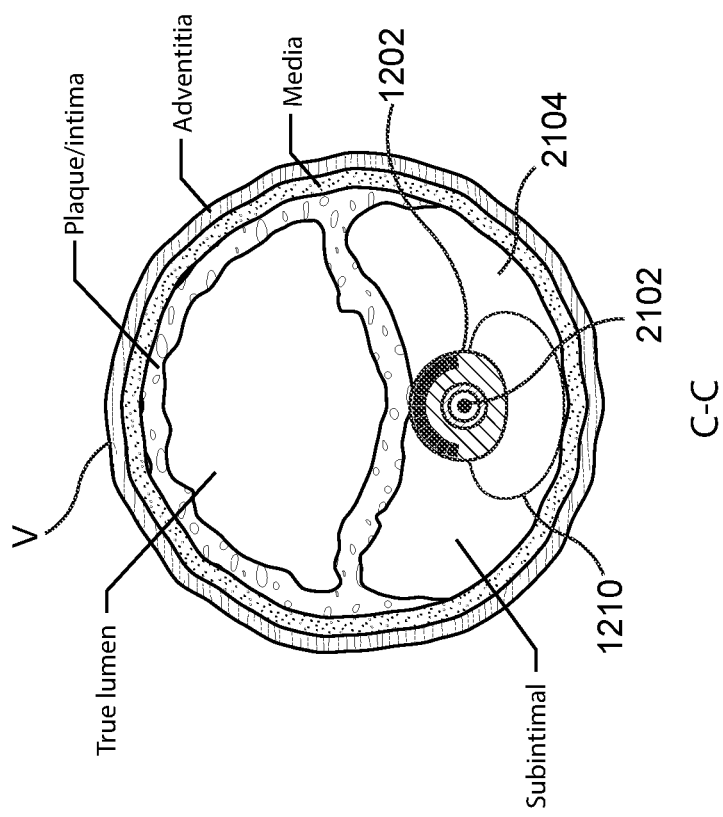
Figure 21D:
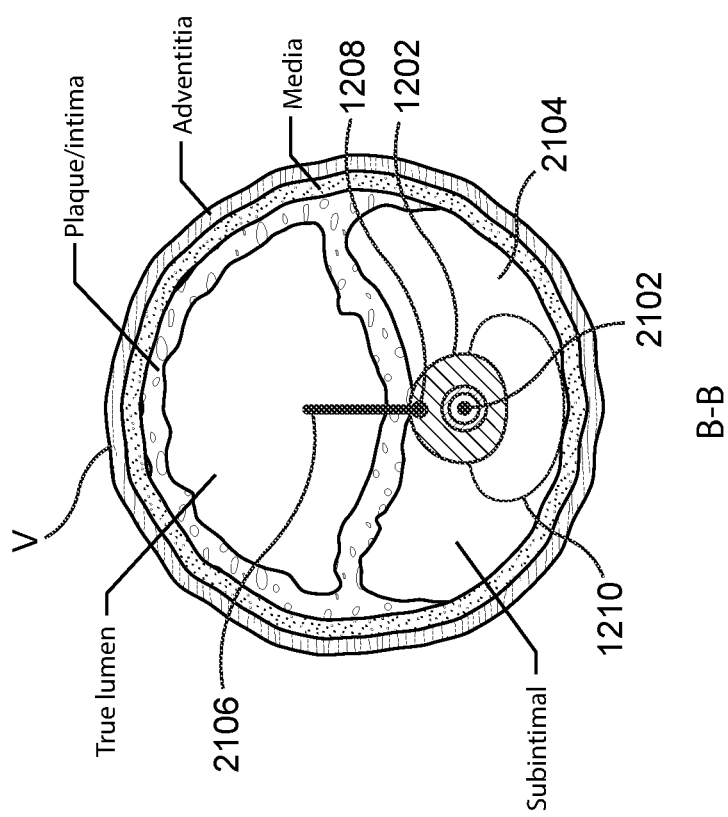
Figure 21F:
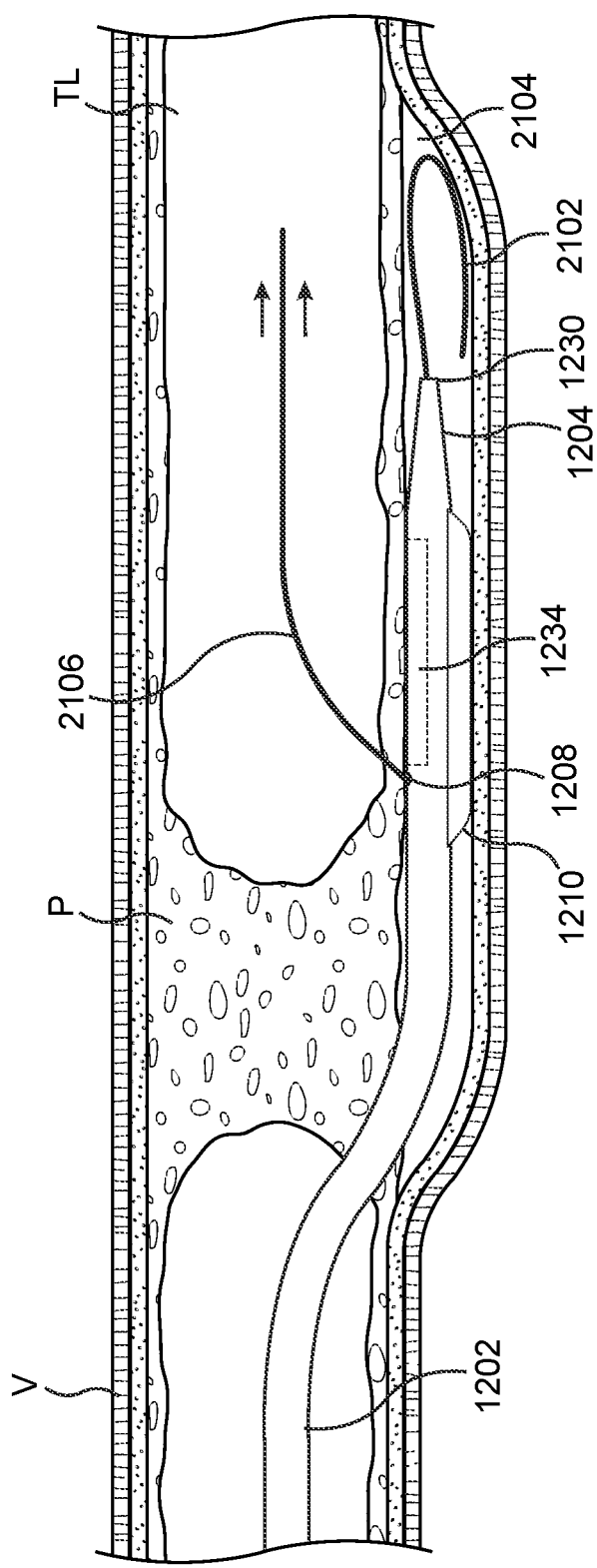
Figure 21G:
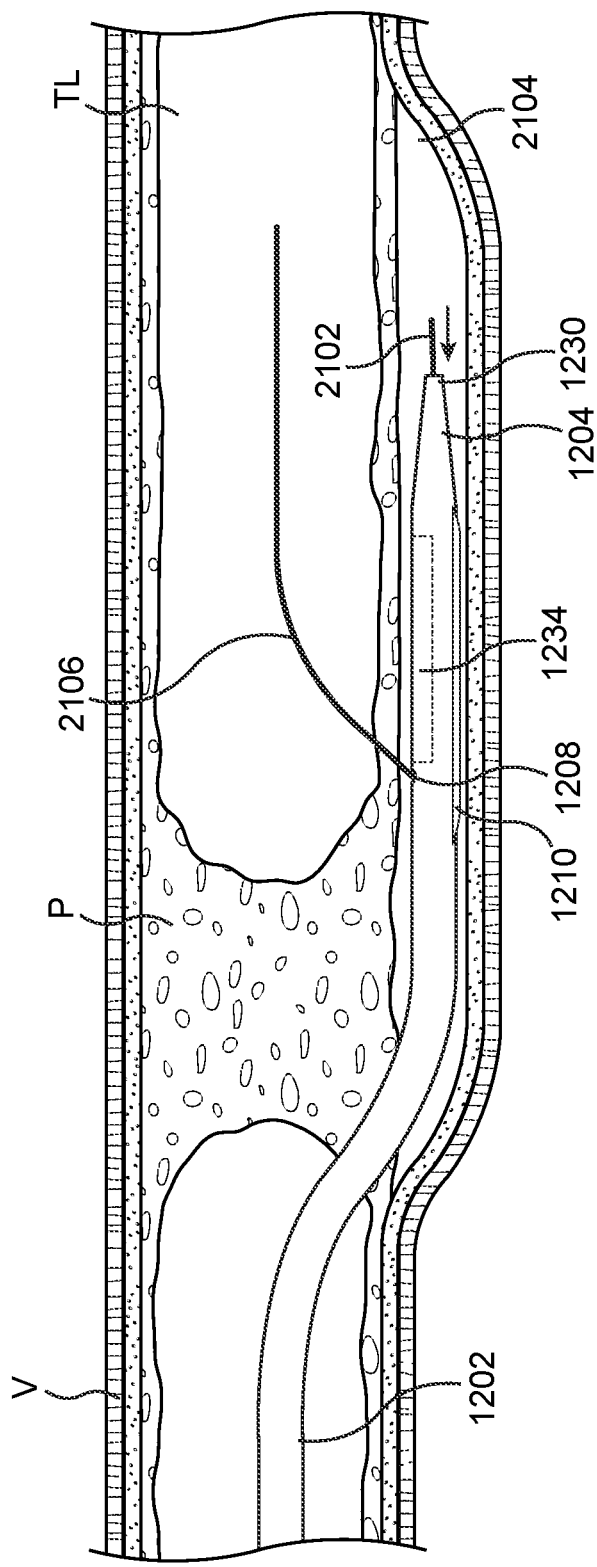
Figure 21H:
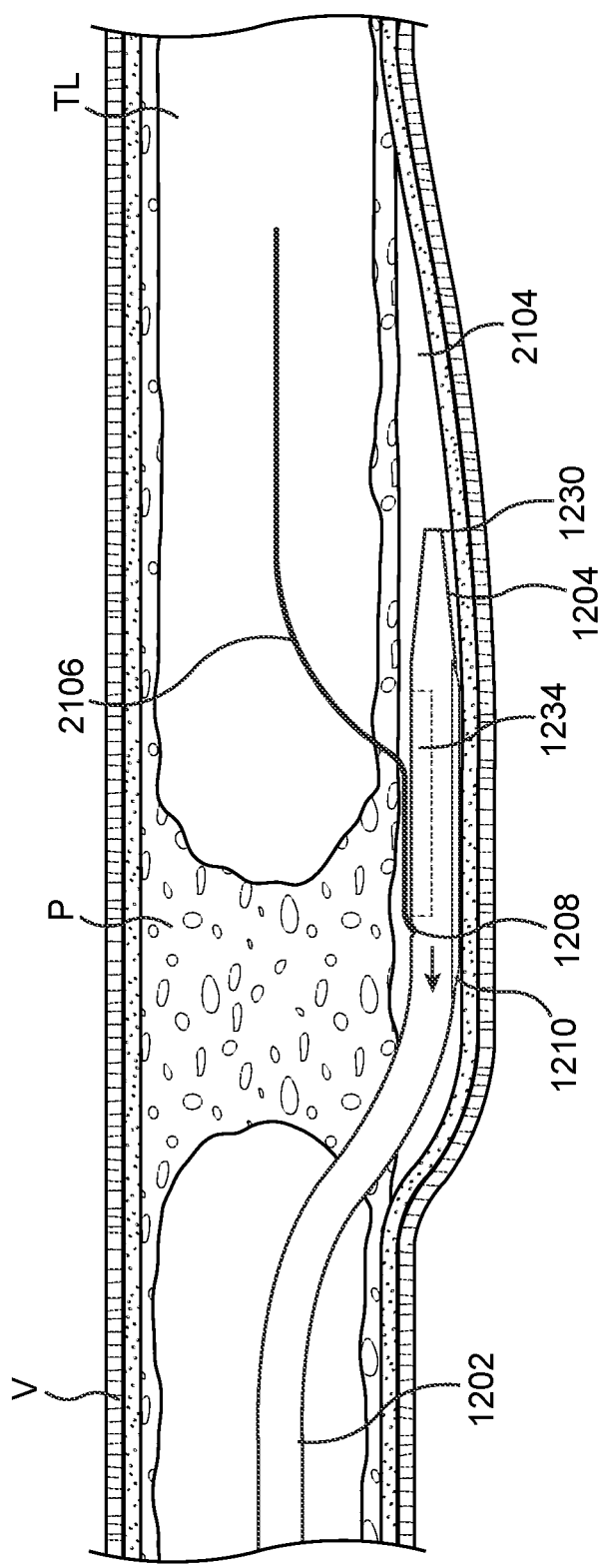
Figure 21I:
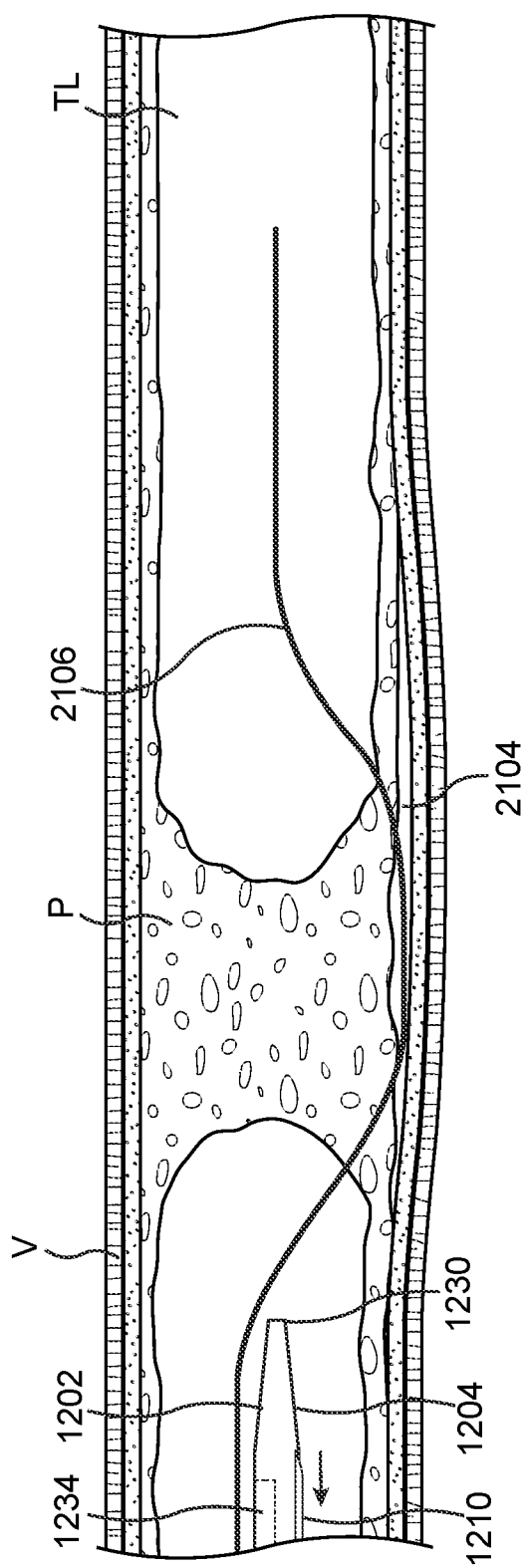
Figure 21J:
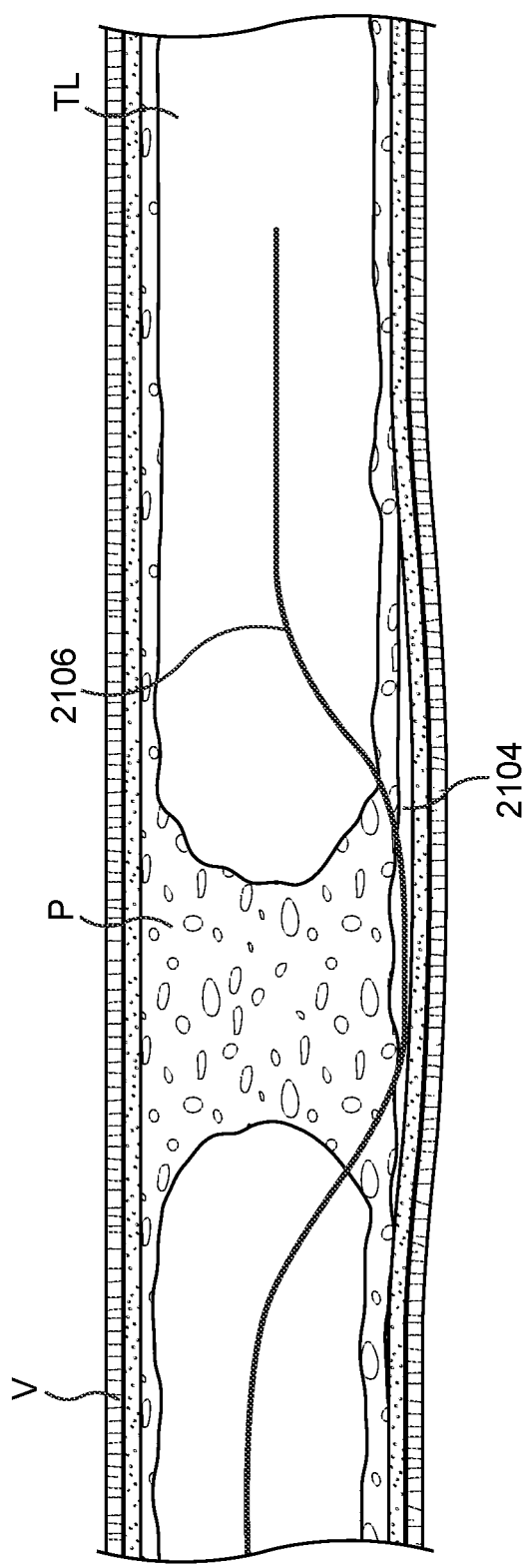
Figure 21K:
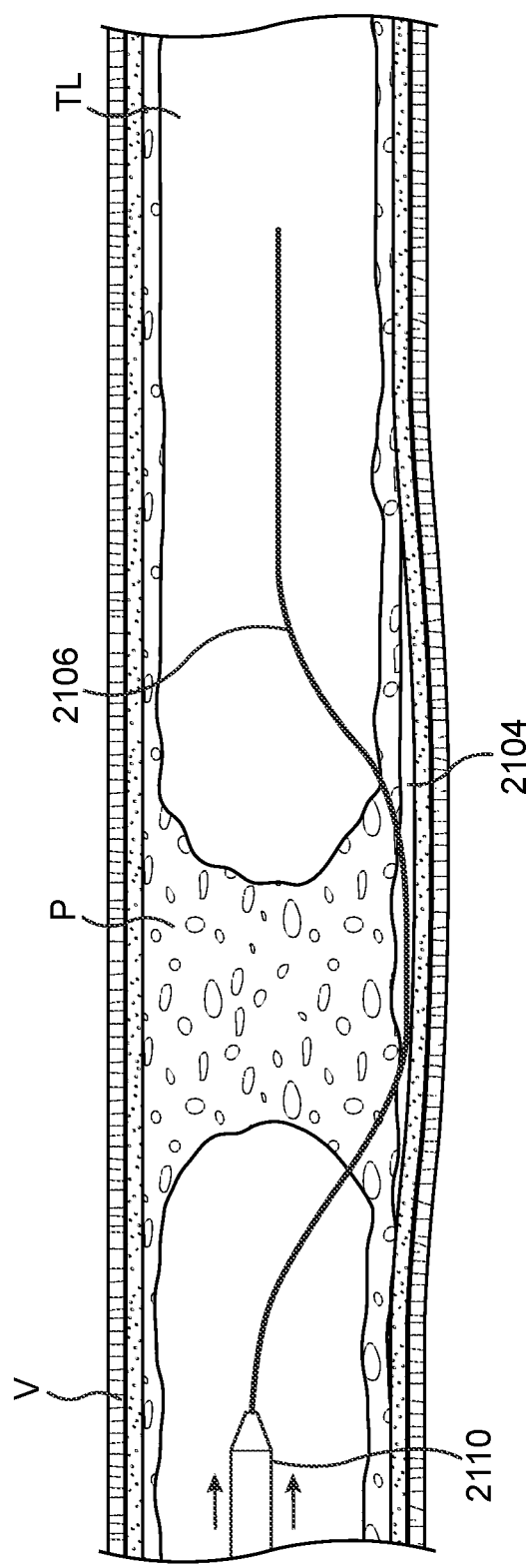
Figure 21L:
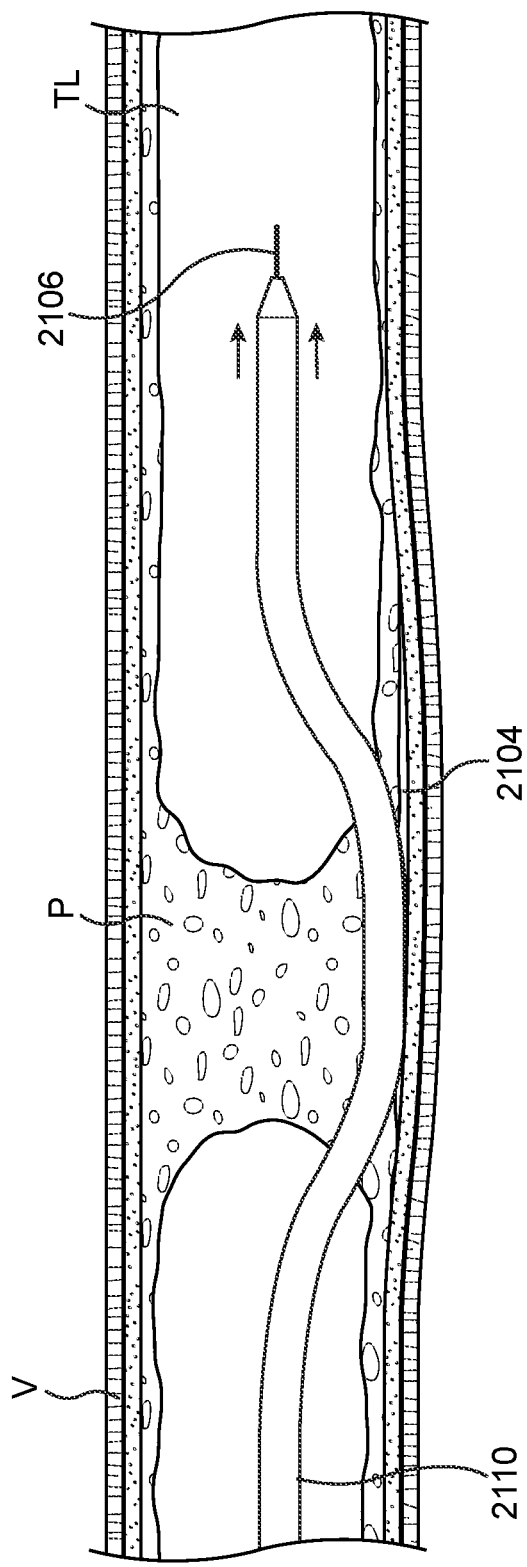
Figure 21M:
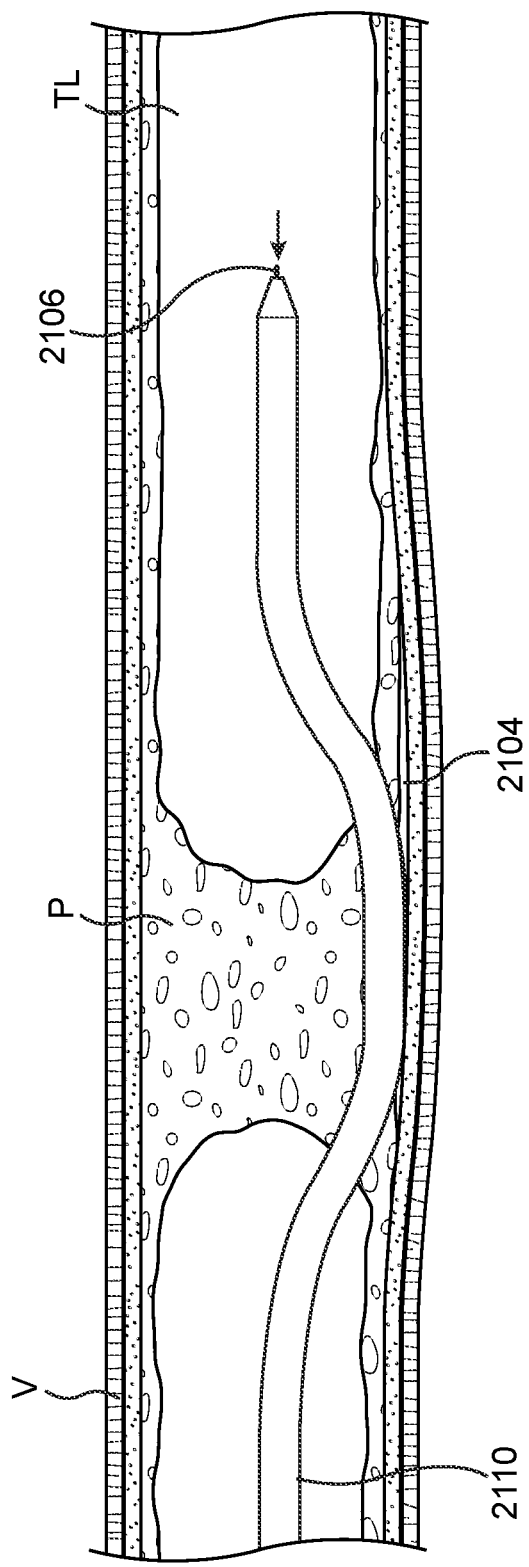
Figure 21N:
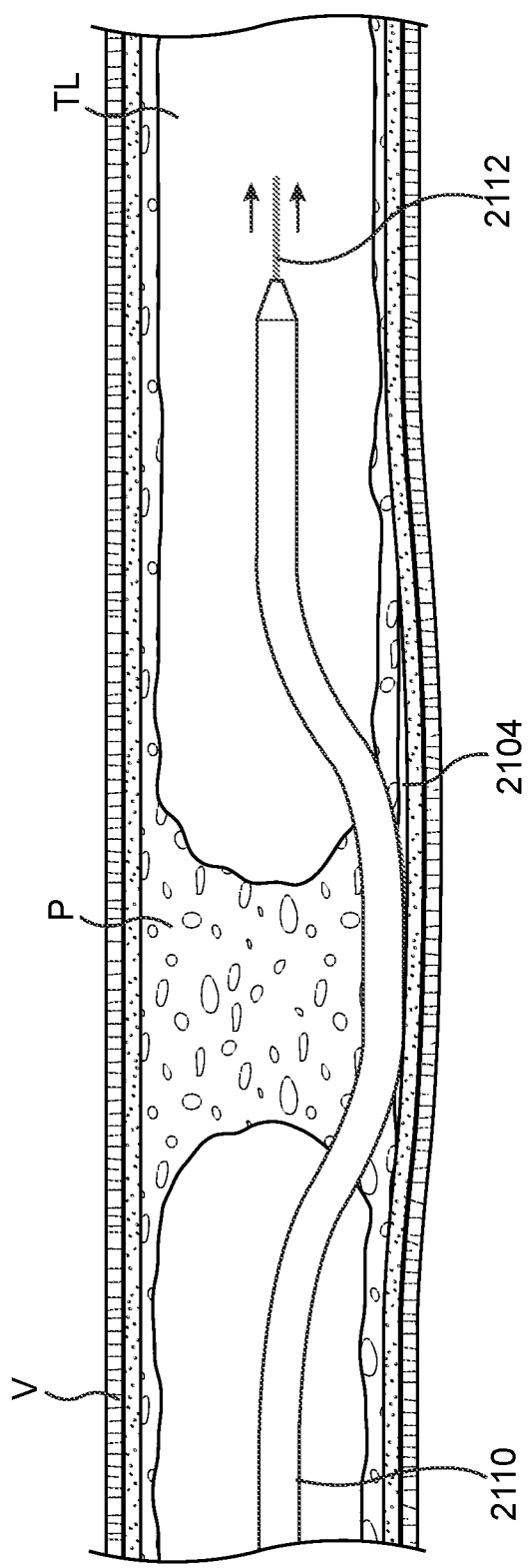
Figure 21O:
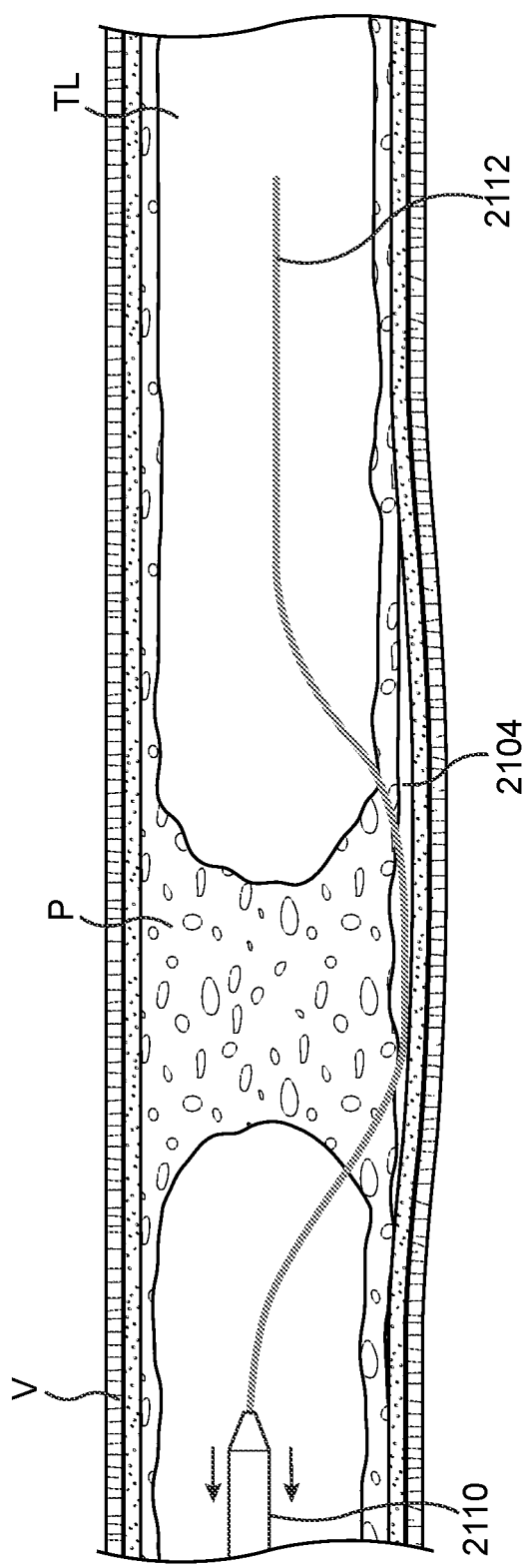
Figure 21P:
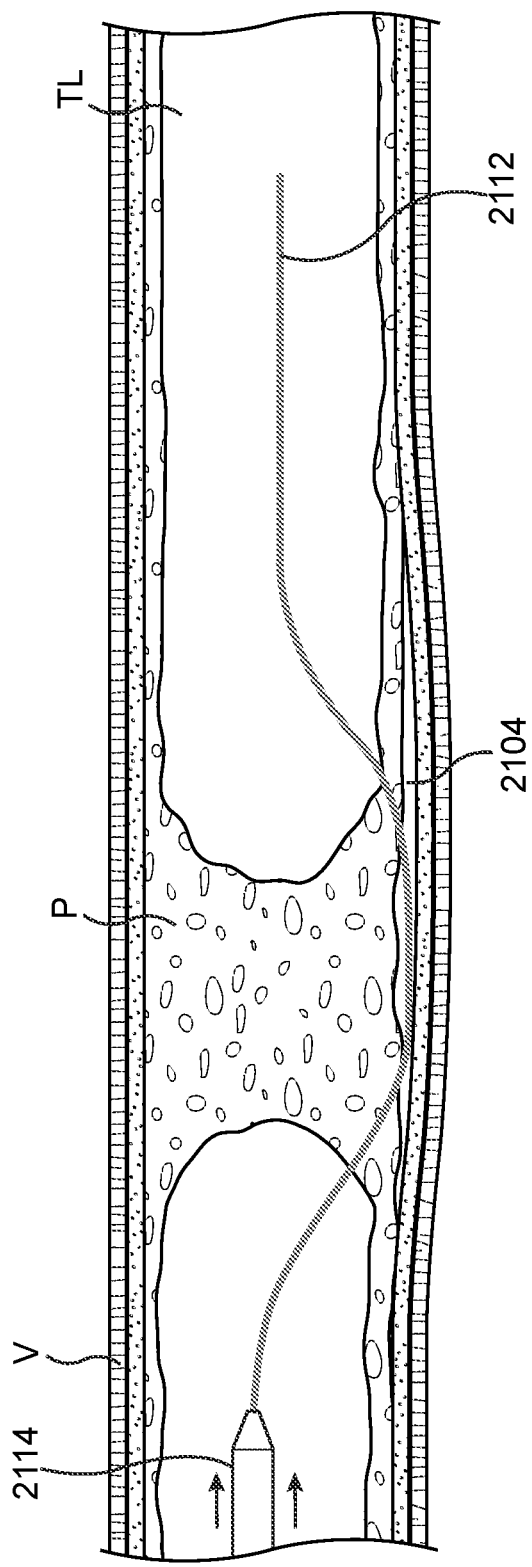
Figure 21Q:
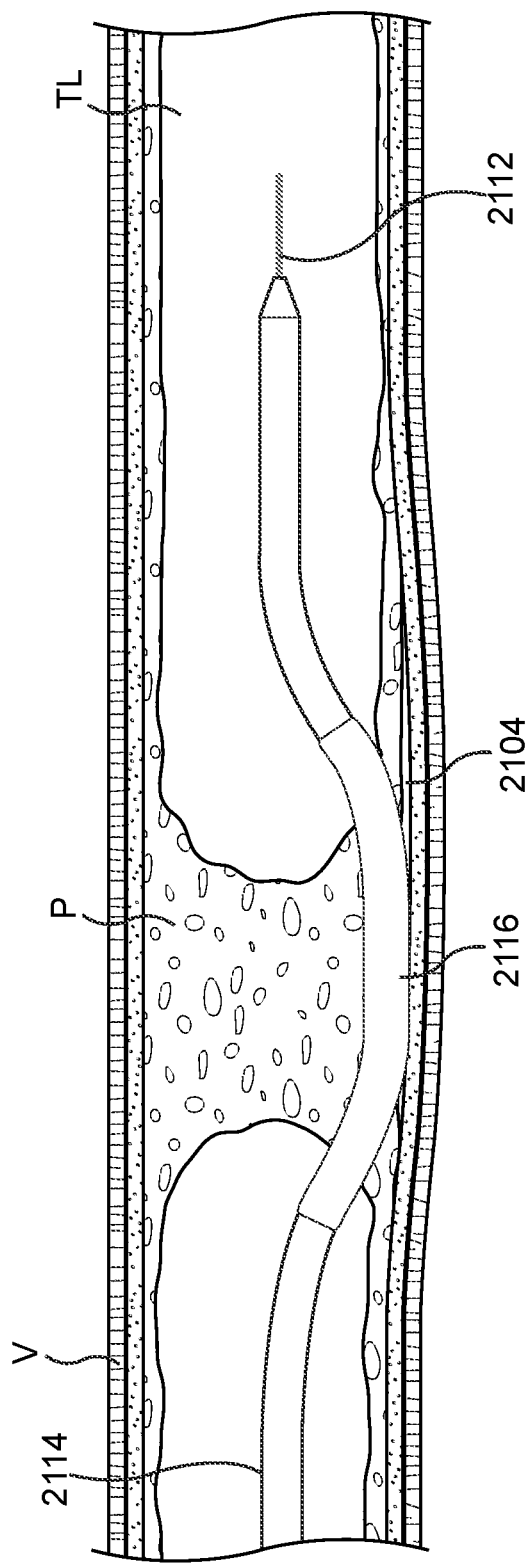
Figure 21R:
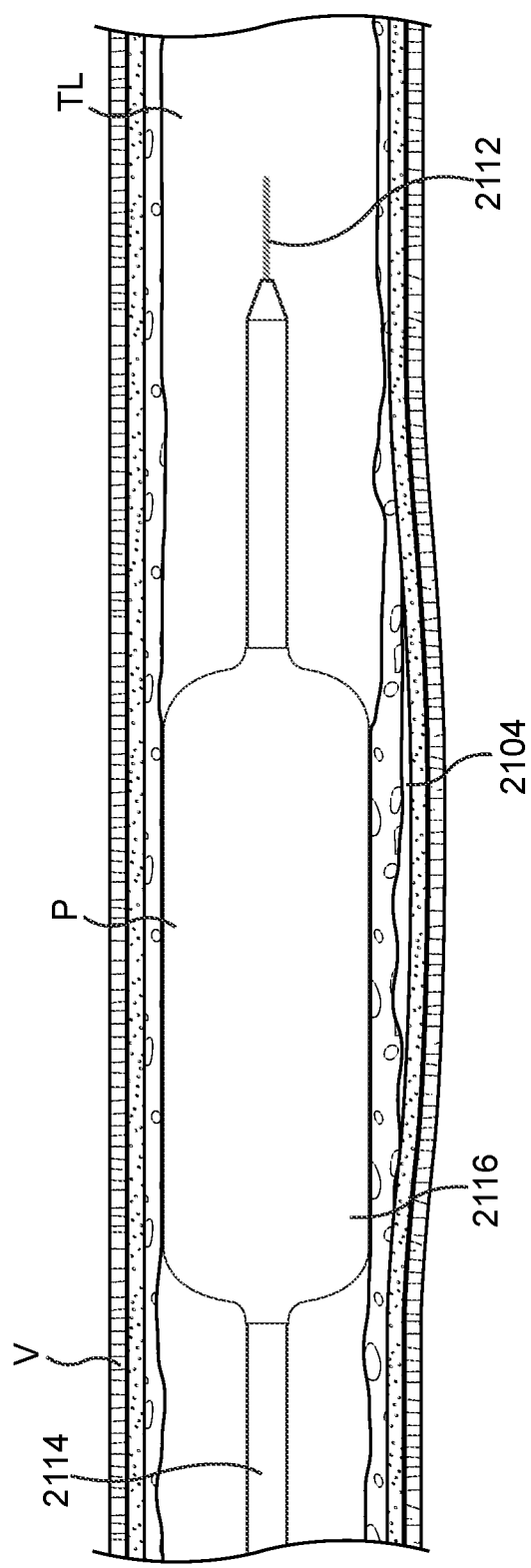
Figure 21S:
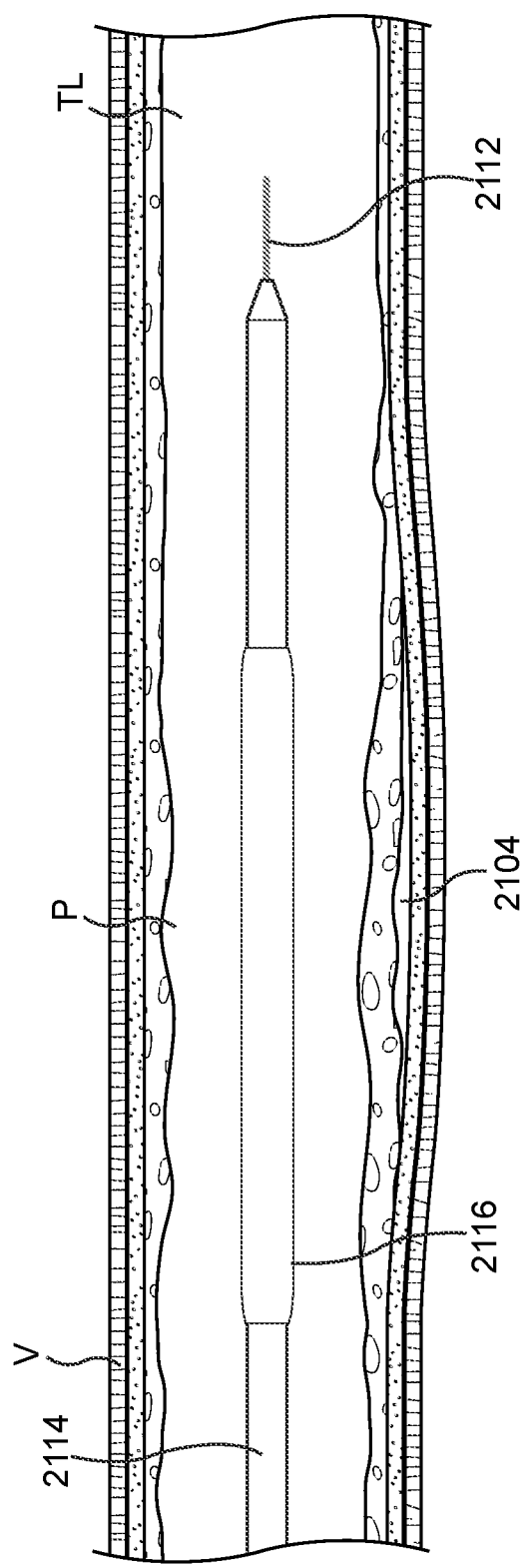
Figure 21T:
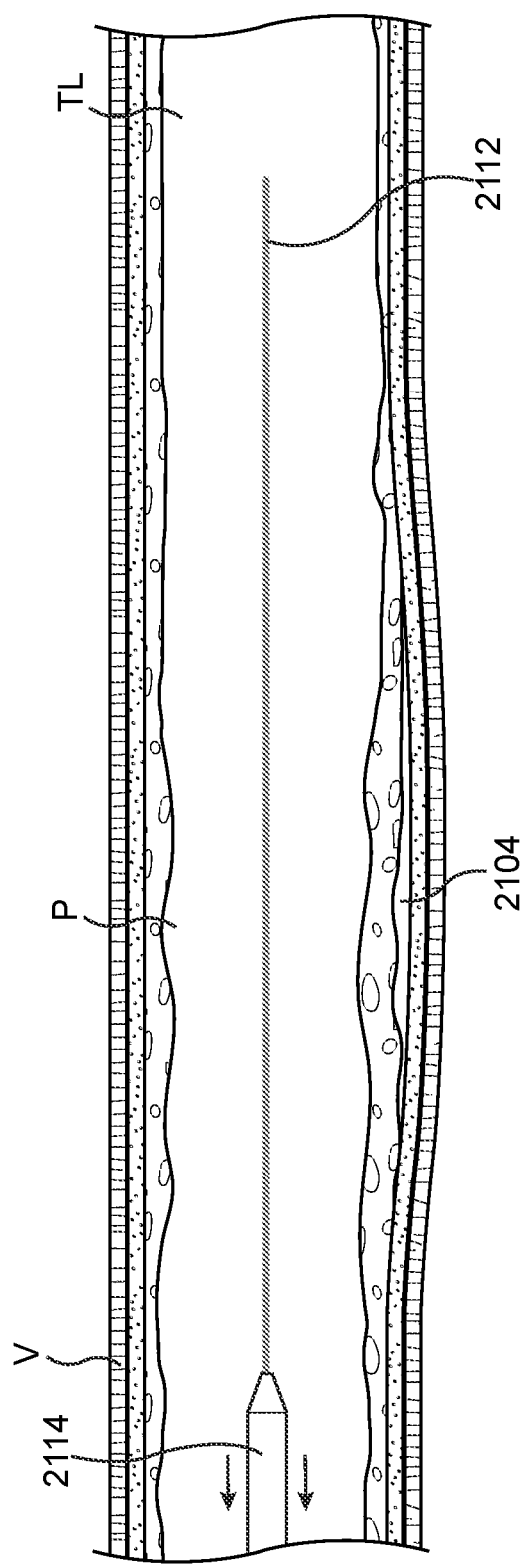
Figure 21U:
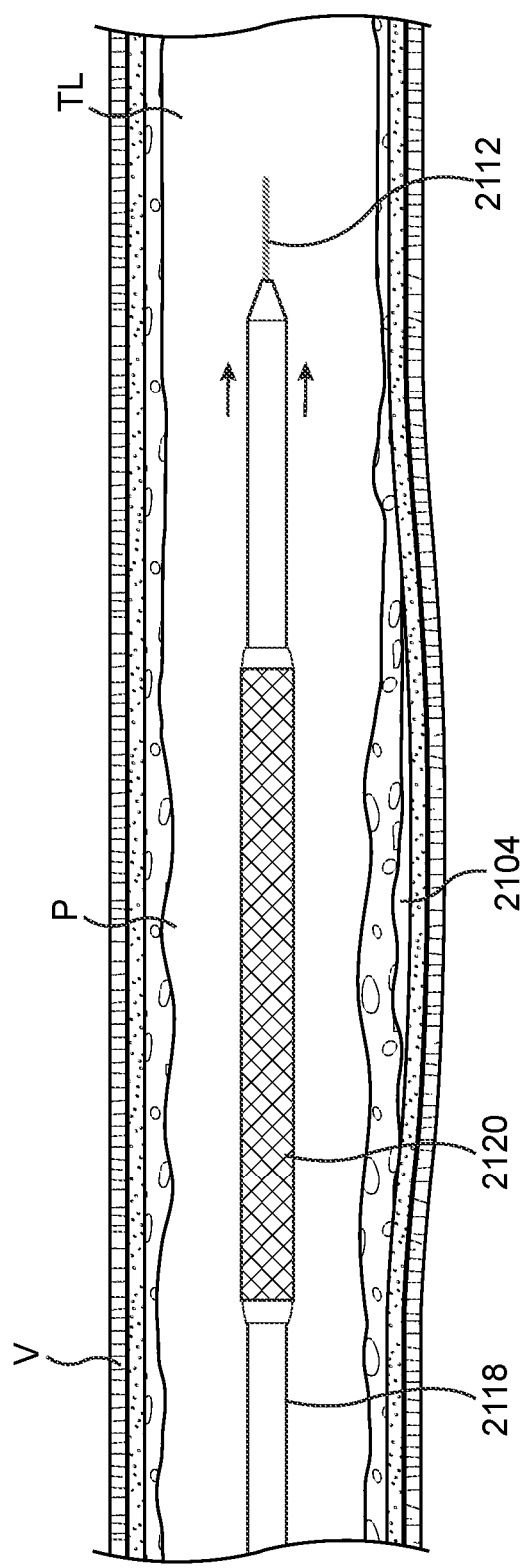
Figure 21V:
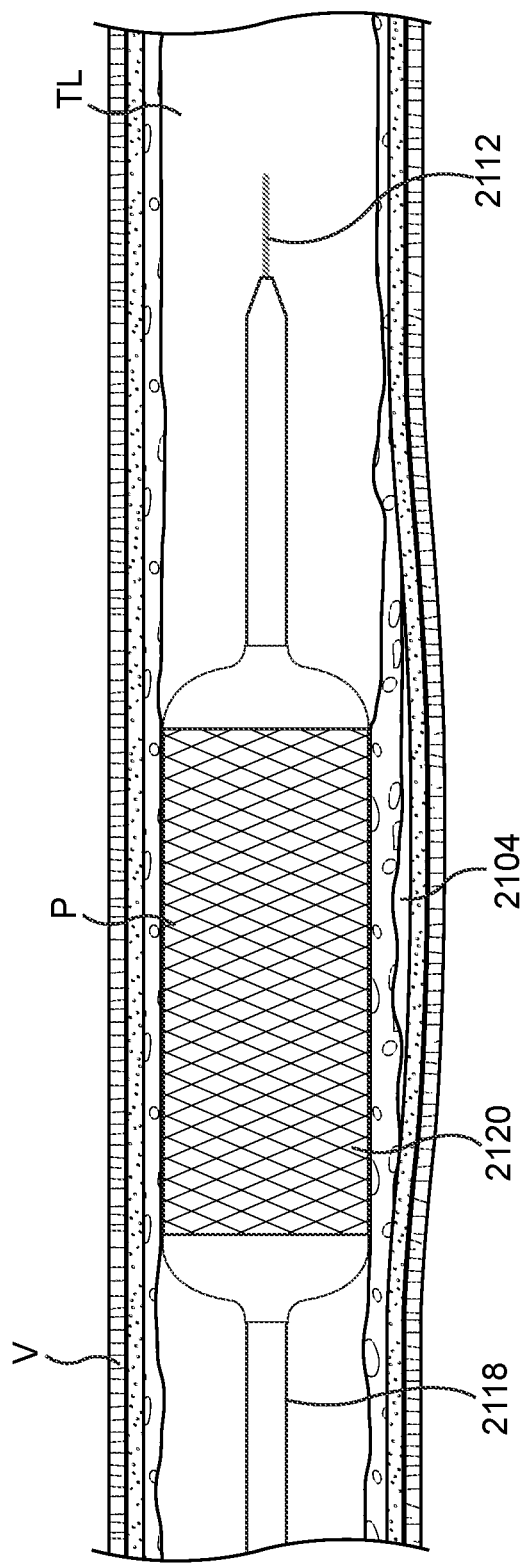
Figure 21W:
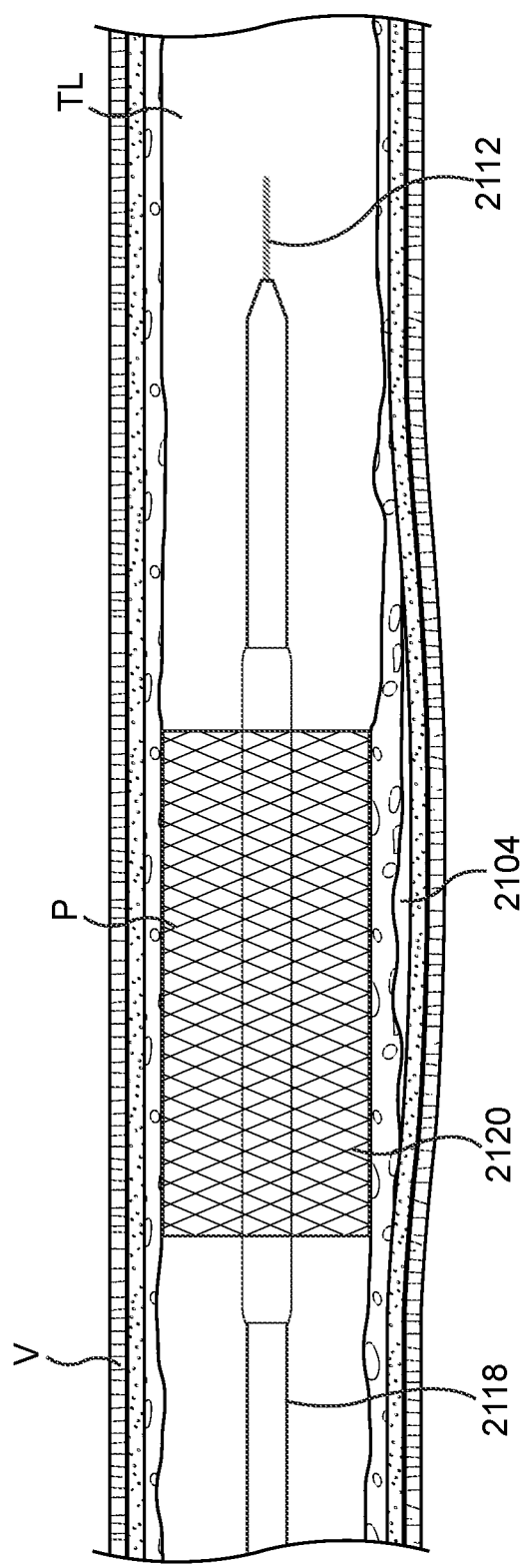
Figure 21X:
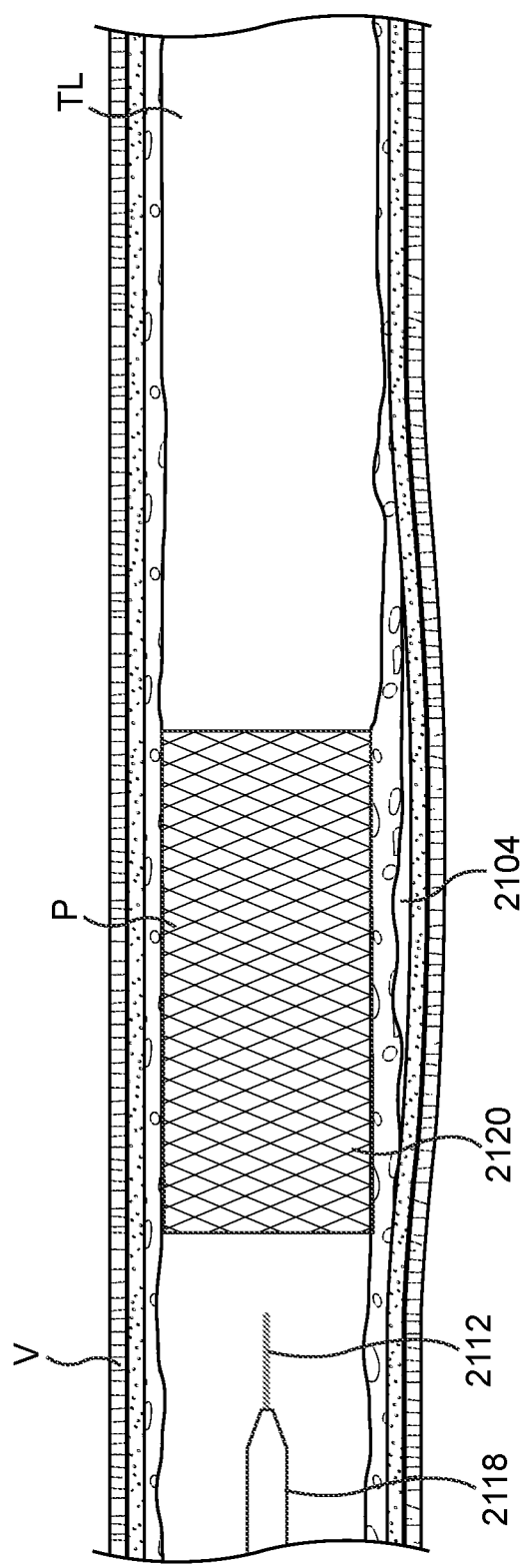

FIGS. 21A-21X illustrate an example of a method of using a catheter to accurately deliver and introduce a re-entry wire into a true lumen of an occluded blood vessel that cannot be crossed using standard techniques. The catheter may be any of the catheters disclosed herein but will focus on using the catheter in FIG. 12 to treat a vessel V obstructed by an obstructive plaque P such as in the case of a chronic total occlusion of a coronary artery or a peripheral artery. The method is similar to the method previously described above with respect to FIGS. 11A-11AR with the major difference being that instead of using a catheter with a common lumen that is used to deliver both the guidewire and the re-entry wire, here the catheter has two separate lumens, one for the guidewire (also referred to as a delivery wire or delivery guidewire) and one for the re-entry wire. Thus, the method is the same as shown in FIGS. 11A-11T in order to deliver the re-entry catheter to the treatment site. FIGS. 11U-11V show removal of the knuckling wire and replacing it with the re-entry wire which is not required in this example because the knuckling wire may remain disposed in the re-entry catheter and also disposed in the false lumen or pocket 2104 formed by the knuckling wire. After use of the knuckling wire is complete to cross the occlusive plaque P the re-entry wire may be introduced while the knuckling wire remains in the re-entry catheter, or alternatively in some examples the knuckling wire may be removed as previously described.

FIG. 21A shows the knuckling wire 2102 remaining in the re-entry catheter 1202 after the re-entry catheter has been advanced over the knuckling wire and advanced subintimally across the occlusive plaque P until the re-entry port 1208 is distal of the occlusion. The distal portion of the knuckling wire 2102 has folded over itself forming a J-shaped or knuckled tip. The ultrasound transducer 1234 is used to provide the physician or operator an image that confirms that the re-entry port will allow the re-entry wire to re-enter the true lumen TL at a position distal of the occlusive plaque P and at the correct angle to properly re-enter the true lumen and advance distally through the true lumen. As before, the ultrasound transducer emits a beam of energy that images a sector of any size, for example an arc of greater than 0 degrees up to 360 degrees, or greater than 0 degrees to 180 degrees, or 10 degrees to 160 degrees, or any range between 0 degrees and 360 degrees. The ultrasound transducer images the blood vessel and has an imaging axis that may be any angle relative to the longitudinal axis of the catheter such as 0 degrees to 180 degrees. For example, the ultrasound beam angle may be 90 degrees. An ultrasound imaging axis angle of 0 to less than 90 degrees is distally facing, while an angle of 90 degrees is perpendicular to the longitudinal axis of the catheter (or side firing), and an angle of greater than 90 degrees up to 180 degrees is proximally facing. Other examples of ultrasound angles include 0 degrees to 135 degrees. The ultrasound beam angle allows an ultrasound image to be obtained that not only shows the anatomy around the re-entry point of the vessel, but also shows the re-entry point where a re-entry wire will exit the subintimal space and re-enter the vessel true lumen, as well as showing the re-entry wire as it is advanced distally, thereby allowing the operator to observe the re-entry wire to ensure that it is properly advanced and does not puncture the vessel or propagate the dissection that was used to create the subintimal pocket.

FIG. 21B shows that once the ultrasound image has been taken and confirms that the re-entry port is in the desired position, the optional balloon 1210 may be inflated and expanded in order to anchor the distal portion of the catheter and prevent unwanted movement. Balloon expansion may be achieved with a fluid such as contrast media, saline, a gas, dilute contrast media, or mixtures thereof. This ensures that the re-entry port position is maintained and does not move. The balloon also displaces the re-entry port radially inward in the vessel so the re-entry port is apposed with the tissue and plaque where the re-entry wire will be advanced from the re-entry port through the subintimal pocket 2104 and through any tissue or plaque back in the true lumen TL.

FIG. 21C shows the re-entry wire 2106 being advanced from the re-entry lumen of the catheter 1202 out the re-entry port 1208. The re-entry wire can exit the re-entry port at any angle, for example when the re-entry wire exits the re-entry port in a distally facing direction, the re-entry angle would be from 0 degrees to less than 90 degrees. If the re-entry wire exits perpendicular to the longitudinal axis of the catheter, then the re-entry wire would exit at a 90 degree angle relative to the longitudinal axis of the catheter. In some examples, the re-entry wire may exit the re-entry port facing proximally in which case the re-entry angle would be greater than 90 degrees up to 180 degrees. The ultrasound imaging axis is selected so that its angle cooperates with the re-entry angle and allows visualization of the re-entry wire. In some examples, the re-entry angle may be 30 degrees, 45 degrees, 60 degrees, or 90 degrees relative to the longitudinal axis of the catheter and the ultrasound imaging axis may be perpendicular (e.g. 90 degrees) or distally facing (e.g. 0 degrees to 90 degrees). These features of the ultrasound transducer may be used in this example or any of the examples of re-entry catheter disclosed herein that include an ultrasound transducer. Any of the other ultrasound beam angles disclosed herein may also be applied in this example.

In this example, the re-entry wire re-enters the true lumen TL in an extra-plaque region of the vessel V while the knuckling wire remains in the guidewire lumen of the catheter and disposed in the subintimal space or pocket 2104. Optionally, the knuckling wire may be removed just before, during, or after introduction of the re-entry wire if desired.

FIGS. 21D-21E show various cross-sections of the vessel V taken at various axial positions in FIG. 21C.

FIG. 21D shows a cross-section taken along the line B-B in FIG. 21C. Here, the re-entry wire 2106 is clearly seen exiting re-entry port 1208 on catheter 1202 and passing through the subintimal space to re-enter the true lumen. Balloon 1210 is also shown inflated to anchor the distal portion of catheter 1202 and to position the re-entry port close to or to abut the re-entry port with the tissue through which the re-entry wire re-enters the true lumen. In some examples, the balloon may be proximal to the re-entry port so that when the balloon is inflated it will block the subintimal space and prevent blood from filling the subintimal space that may create a hematoma that can make re-entry more difficult because the blood that fills the subintimal space may compress the true lumen.

FIG. 21E shows a cross-section taken along the line C-C in FIG. 21C. Here, the ultrasound transducer is observed just distal of the re-entry port to ensure that the image provided by the ultrasound transducer shows a clear path for the re-entry wire to exit the re-entry port and re-enter the true lumen.

FIG. 21F shows further distal advancement of the re-entry wire 2106 through the re-entry lumen in the catheter, exiting the re-entry port 1208 and the re-entry wire re-enters the true lumen TL distal of the occlusive plaque P and is advanced distally. Ultrasound imaging may be continued as desired.

FIG. 21G shows that after the re-entry wire has been delivered to a desired position distal of the occlusive plaque P, the balloon 1210 may be deflated and the knuckling wire 2102 may be proximally retracted through the guidewire lumen and removed from the catheter 1202.

FIG. 21H shows that after the knuckling wire has been removed from the patient, the re-entry catheter 1202 may be proximally retracted and removed from the pocket 2104 until the entire catheter is proximal of the obstructive plaque P. In any of the steps where the catheter is disposed in the pocket 2104, blood or other fluid may be aspirated from the pocket by using one of the lumens, e.g. the re-entry wire lumen or the guidewire lumen to draw fluid proximally to a reservoir, syringe or other device that is coupled to that lumen. The optional balloon may be inflated to help prevent additional blood from filling the subintimal space.

FIG. 21I shows further proximal retraction of catheter 1202 so the entire catheter is removed from the subintimal space and only the re-entry wire 2106 remains in the pocket P in the subintimal space and a distal portion of the re-entry wire extends distally past the occlusive plaque P in the true lumen.

In FIG. 21J, the entire re-entry catheter has been removed from the vessel V and from the patient leaving only the re-entry wire 2106 crossing the obstructive plaque P by passing the plaque in the subintimal pocket 2104 so that the distal end of the re-entry wire is distal of the obstructive plaque.

FIG. 21K shows an optional step where a microcatheter, sheath, or other wire exchange catheter 2210 is advanced distally over the re-entry wire 2106 towards the obstructive plaque P. The wire exchange catheter is often a microcatheter and it will be used to exchange the re-entry wire for a more appropriate guidewire (sometimes referred to as a workhorse guidewire) that can be used to help guide and deliver a diagnostic or therapeutic device to the target treatment region. The workhorse wire has more desirable mechanical properties for the rest of the procedure such as less stiffness so as to be more atraumatic and therefore safer to use.

FIG. 21L shows further distal advancement of the microcatheter, sheath, or other wire exchange catheter 2110 distally so that it crosses the obstructive plaque P by passing subintimally through the pocket 2104 formed by the re-entry wire and the microcatheter re-enters the true lumen TL where the re-entry wire re-enters the true lumen. The wire exchange catheter 2110 is then advanced so that its distal tip is distal of the obstructive plaque P in the extra-plaque region of the vessel.

In FIG. 21M, after the wire exchange catheter 2110 has been advanced distally to a desired position distal of the obstructive plaque P the re-entry wire 2106 may be retracted proximally and removed from the wire exchange catheter and removed from the patient.

FIG. 21N shows that once the re-entry wire has been removed, it may be replaced with a more appropriate guidewire, sometimes referred to as a workhorse wire 2112. The workhorse wire is advanced distally through the wire exchange catheter 2110 across the obstructive plaque P through the subintimal space and then exits the distal end of the wire exchange catheter distal of the obstructive plaque in the extra-plaque region of the vessel and in the true lumen TL. As previously discussed, optionally, the stick and swab technique may be used where the re-entry wire is a stiffer wire used to re-enter the true lumen and then it may be replaced with another wire that has more desirable mechanical properties (e.g. a softer wire) to prevent damage to the vessel and surrounding tissue.

In FIG. 21O, once the new workhorse wire 2112 has been delivered and replaces the re-entry wire, the microcatheter, sheath, or other wire exchange catheter 2110 may be proximally retracted and removed from the blood vessel and removed from the patient leaving only the workhorse wire 2112 in the vessel and crossing the obstructive plaque P.

Replacement of the re-entry wire for a workhorse wire is optional and the previous replacement steps may be omitted if the operator wishes to proceed straight to introducing a therapeutic device using the re-entry wire.

FIG. 21P shows advancement of a therapeutic device, here an angioplasty catheter 2114 distally over the workhorse wire 2112.

FIG. 21Q shows further distal advancement of the angioplasty catheter 2114 until the radially expandable member, here a balloon 2116 is in the subintimal space centered under the obstructive plaque P. The distal end of the angioplasty catheter is disposed distal of the obstructive plaque P in the extra-plaque region in the true lumen TL.

FIG. 21R shows radial expansion of the radially expandable member 2116, here a balloon. The balloon is expanded by inflating it with a fluid such as saline, contrast media, a gas, or mixtures thereof (e.g. dilute contrast media). Radial expansion compresses the obstructive plaque P and re-opens the lumen so that it is patent and blood flow can be restored. The balloon may be any of the drug eluting balloons disclosed herein.

After successful balloon angioplasty has been performed and the lumen is patent, the balloon 2116 may be collapsed by deflating it as seen in FIG. 21S.

In FIG. 21T, the angioplasty catheter is proximally retracted away from the former obstructive plaque P and removed from the patient leaving only the workhorse wire 2112 left in the vessel V which now has a patent lumen.

FIG. 21U shows that after the angioplasty catheter has been removed from the patient, a stent delivery catheter 2118 may be advanced distally over the workhorse guidewire 2112 so that the stent 2120 is centered along the location of the previous obstructive plaque P.

In FIG. 21V the stent 2120 is radially expanded by inflating a balloon on the stent delivery catheter. The balloon may be inflated by inflating with a fluid such as saline, contrast media, a gas, or combinations thereof (e.g. dilute contrast media). The stent 2120 provides a scaffolding which supports the vessel wall and prevents it from collapsing or moves dissection flaps out of the lumen and holds them against the vessel wall. In this example or any example disclosed herein, the stent may be a balloon expandable stent or a self-expanding stent which does not require balloon inflation. The stent here, or in any example may also be a drug eluting stent which delivers a therapeutic agent to prevent restenosis. Some examples of anti-restenosis drugs may include Paclitaxel or mTOR inhibitors such as the limus drugs (e.g. sirolimus, everolimus, zotarolimus, biolimus etc.). Other drugs may include anti-thrombosis drugs such as those which are anti-clotting or anti-platelet sticking drugs.

FIG. 21W shows that once the stent 2120 has been deployed into a desired position and stenting is completed, the balloon may be deflated.

FIG. 21X shows proximal retraction of the stent delivery catheter 2118 and the workhorse wire 2112 away from the stent. The stent delivery catheter 2118 and the workhorse wire 2112 are removed from the patient leaving only the expanded stent 2120 in the patient supporting the vessel wall.

In this example, optional angioplasty is used and followed by optional stenting using two separate devices. In some examples angioplasty may be performed without stenting or direct stenting may be performed where the stent is deployed without a separate balloon angioplasty procedure. One of skill in the art appreciates that any of these methods may be used with the wire re-entry procedures described herein using any of the examples of re-entry catheter disclosed herein.

Example of Re-Entry without a Balloon

Figure 23A:
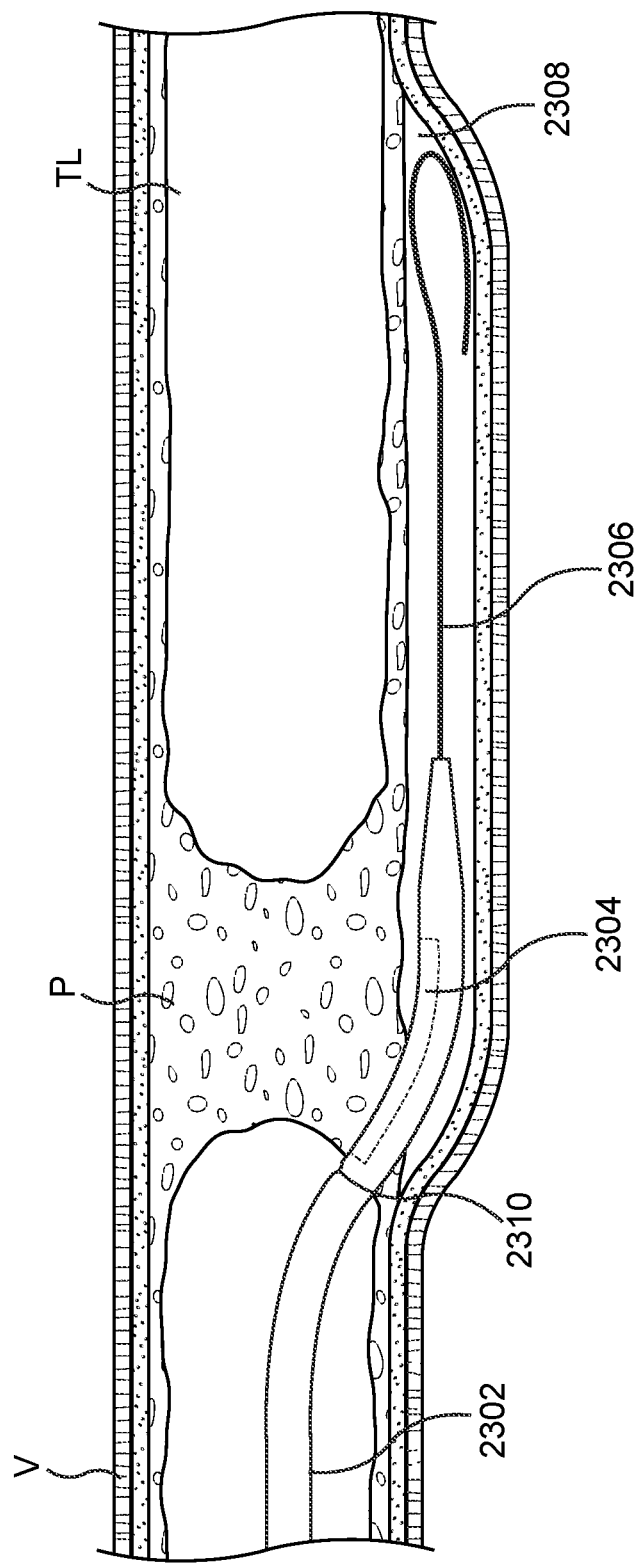
FIGS. 23A-23C show another example of a method of treating an obstruction in a vessel using a catheter without a balloon.
Figure 23B:
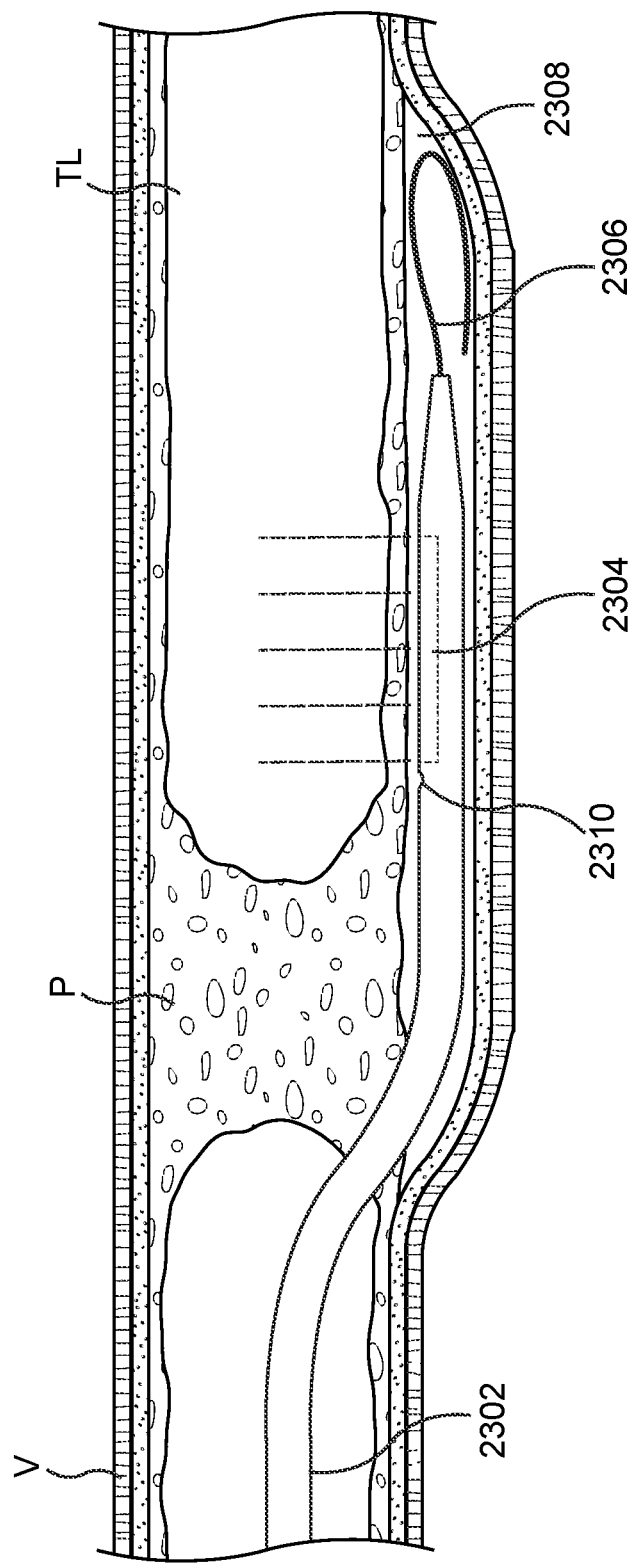
Figure 23C:
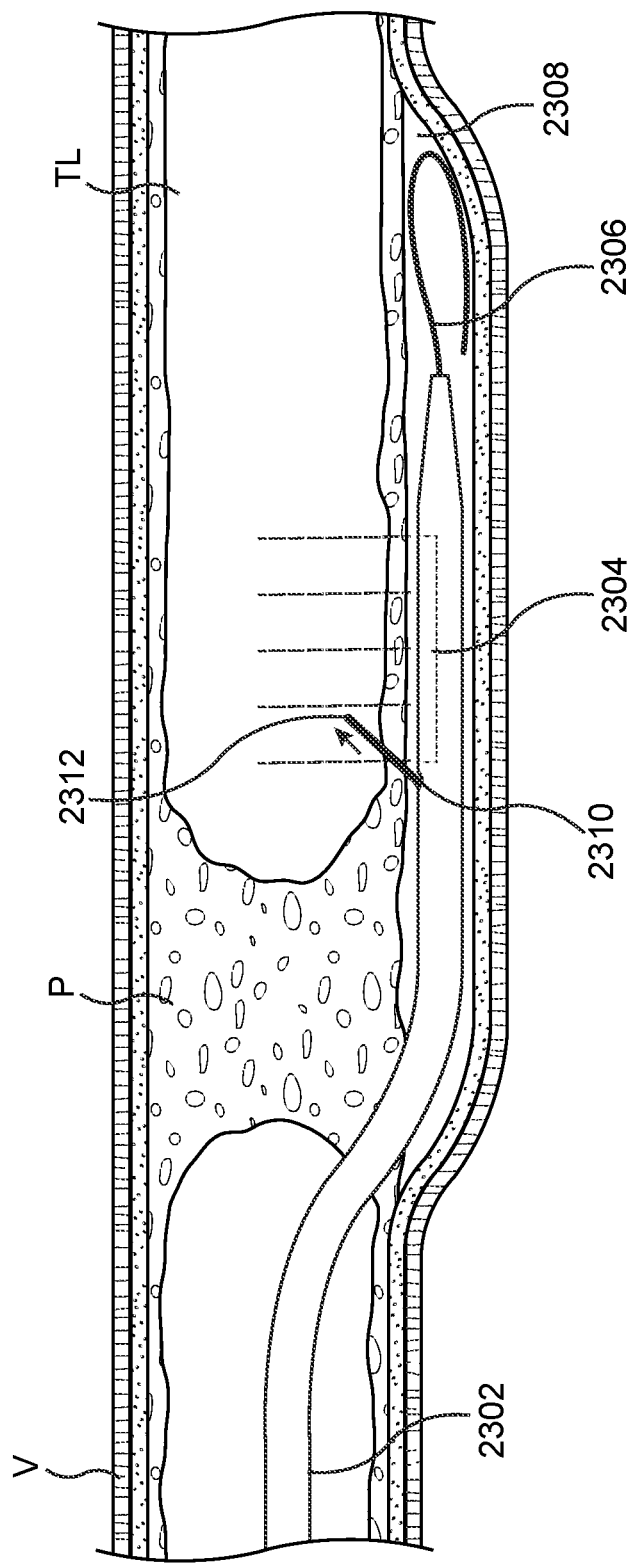

In some examples, the re-entry catheter may not include the optional balloon or expandable member. FIGS. 23A-23C shows a portion of the method previously described above using a catheter such as the one seen in FIG. 12 but when the catheter does not include the optional balloon. The method is generally the same as previously described but without the balloon expansion and contraction steps.

FIG. 23A shows that after the knuckling wire 2306 has been delivered past the obstructive plaque P as previously described, a re-entry catheter 2302 such as the one in FIG. 12 (or any example disclosed herein) but without the balloon may be advanced over the knuckling wire distally so that the catheter passes the occlusive plaque P in the subintimal pocket 2308. A transducer 2304 may be used to image the vessel to determine the position of the distal portion of the re-entry catheter.

In FIG. 23B, the re-entry catheter 2302 is advanced so that the re-entry port 2310 is distal of the obstructive plaque. The position of the catheter and re-entry port 2310 may be verified by the image formed by ultrasound transducer 2304. Ultrasound beam angle and re-entry wire exit angle have previously been discussed before and any of the example angles may be used here. The beam images the vessel and the re-entry wire as it re-enters the true lumen to allow the operator to verify proper re-entry and advancement of the wire through the true lumen.

FIG. 23C shows that once the position of the re-entry port 2310 has been confirmed by imaging with the ultrasound transducer 2304, the re-entry wire 2312 may be advanced through the re-entry lumen and the re-entry wire will exit re-entry port 2310 and be imaged by the ultrasound beam. The re-entry wire re-enters the true lumen TL of the vessel V. In any step, the re-entry catheter may be axially moved to adjust axial position or rotationally moved to circumferentially orient the catheter into a desired position. Once the re-entry wire has been delivered, other aspects of the method are generally the same as previously described above in FIGS. 21A-21X.

Rapid Exchange or Over the Wire Configurations

As previously mentioned, in any example of re-entry device disclosed herein, the guidewire lumen or the re-entry wire lumen may be a rapid exchange (RX) lumen or an over the wire (OTW) lumen and any combination of RX and OTW may be used when there are more than one lumens. FIGS. 24A-24F illustrate various configurations of re-entry catheters with RX or OTW lumens.

Figure 24A:
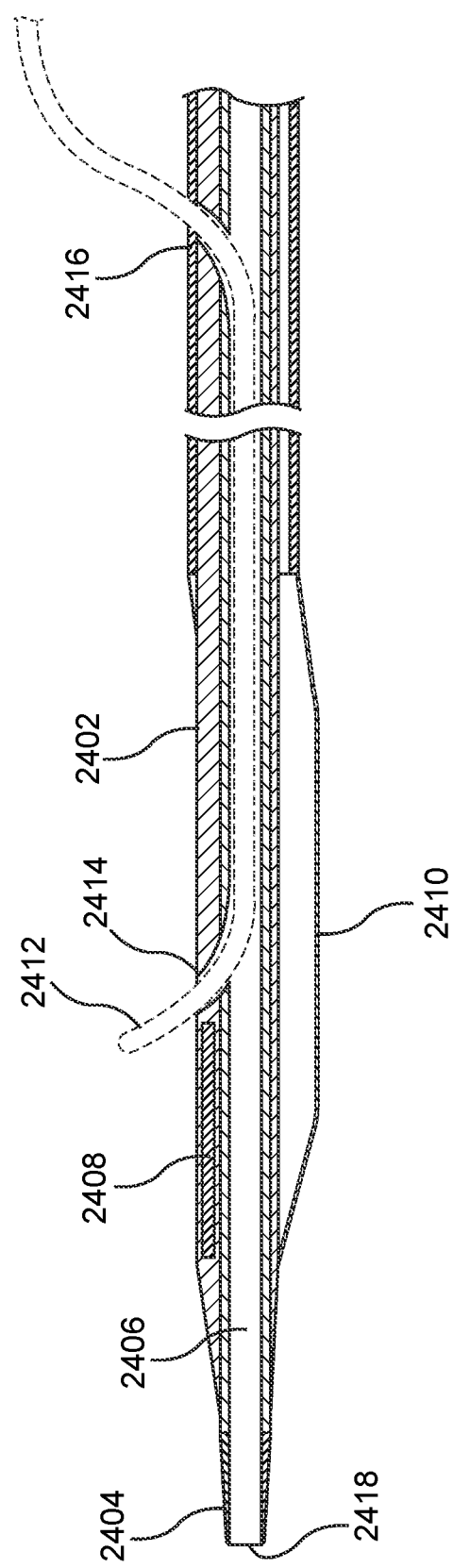
FIGS. 24A-24F show cross-sections of examples of re-entry catheters with rapid exchange or over the wire lumens.

FIG. 24A shows an example of a rapid exchange re-entry catheter such as the one in FIGS. 1-7 above where there is a single common lumen for the guidewire and the re-entry wire. Because there is a single lumen that accommodates both wires, the lumen can be rapid exchange or over the wire. Here, the distal portion 2404 of re-entry catheter 2402 includes an ultrasound transducer 2408, optional balloon 2410, central lumen 2406, distal port 2418, re-entry wire port 2414 and proximal port 2416. Here, a guidewire (not shown) or a re-entry wire 2412 enters common lumen 2406 at the proximal port 2416 and then exits the re-entry port 2414 or distal port 2418. In the case where a guidewire (not shown) is disposed in the common lumen, the guidewire enters the common lumen at the proximal port 2416 and exits the distal port 2418. The distal port is located at the distal-most end of the catheter and the re-entry port is disposed proximal of the ultrasound transducer 2408. The proximal port 2416 is disposed closer to the distal-most end of the catheter than the proximal-most end of the catheter. For some operators, rapid exchange catheters allow shorter wires to be used and manipulated more easily than an over the wire catheter. Rapid exchange configurations also allow smaller crossing profiles of the re-entry catheter which may be desirable. The proximal portion of the common lumen proximal of the proximal port 2416 may be blocked off or otherwise plugged and there may not be a connector on the hub that is coupled with the common lumen.

Figure 24B:
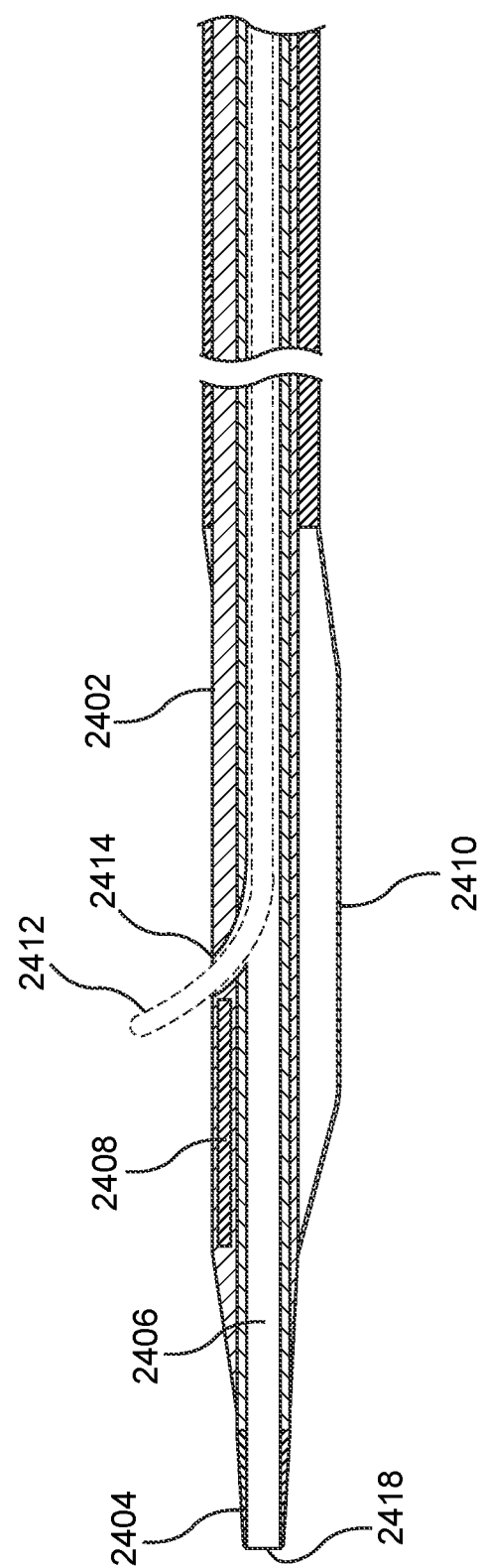

FIG. 24B shows the same catheter in FIG. 24B but with the common lumen having an over the wire configuration. Here re-entry catheter 2402 includes distal port 2418, ultrasound transducer 2408, balloon 2410 and re-entry port 2414 adjacent the distal portion 2404 of the catheter. There is a single lumen 2406 that can accommodate a guidewire or a re-entry wire 2412. The proximal port for introducing a guidewire or re-entry wire into the common lumen 2406 is disposed at the proximal end of the catheter. Therefore, the proximal port is located closer to the proximal-most end of the catheter than the distal-most end of the catheter. This configuration is referred to as an over the wire configuration and requires longer wires to be used when compared to a rapid exchange catheter. There may be a connector on the proximal hub that is fluidly coupled with the lumen. In some situations, over the wire configurations may require a trapping device to remove the re-entry catheter over a short wire. Examples of trapping devices include a balloon catheter that can trap the wire when the balloon is inflated and prevent the wire from slipping or inadvertently moving.

FIGS. 24C-24F show different configurations of a re-entry catheter having a lumen for the guidewire and a separate lumen for the re-entry wire.

Figure 24C:
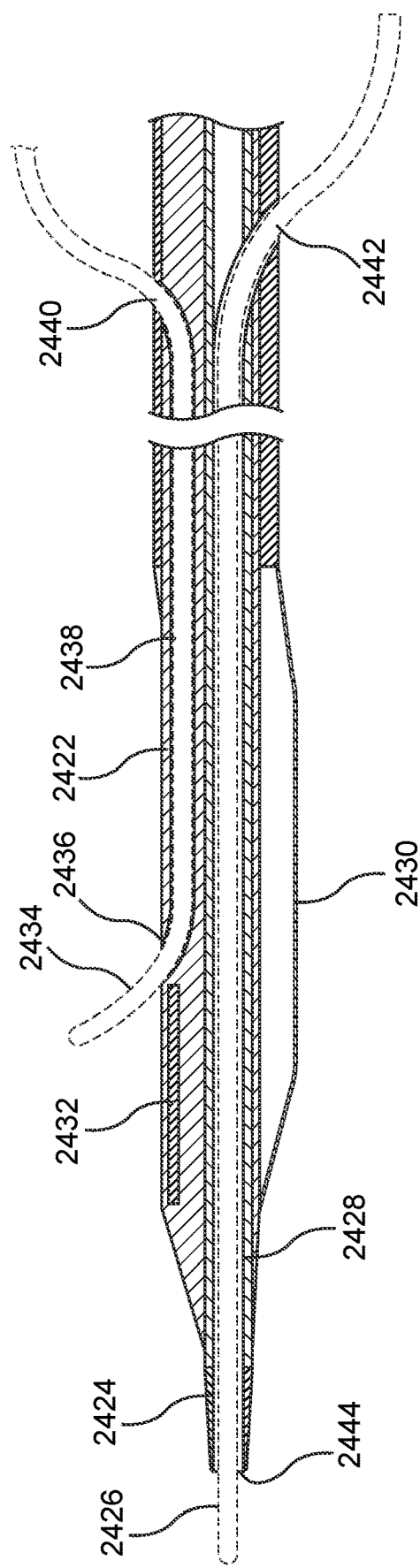

FIG. 24C shows an example of a re-entry catheter 2422 with both lumens configured as rapid exchange lumens. The re-entry catheter has a guidewire lumen 2428 and a re-entry wire lumen 2438. The catheter 2422 includes the optional balloon 2430 and also has an ultrasound transducer 2432. The distal port 2444 allows a guidewire 2426 to exit the distal portion 2424 of the catheter and a re-entry port 2436 allows a re-entry wire 2434 to exit re-entry lumen 2438 of the catheter. The re-entry port may be proximal of the ultrasound transducer. The proximal re-entry port 2440 is disposed closer to the distal end of the catheter than the proximal-most end of the catheter, therefore the re-entry lumen is a rapid exchange lumen. The re-entry wire lumen proximal of the re-entry port may be blocked off or otherwise plugged, and there may not be a connector on the proximal hub that is fluidly coupled with the re-entry lumen. Similarly, the guidewire proximal port 2442 is also closer to the distal end of the catheter than the proximal-most end of the catheter, therefore the guidewire lumen is also a rapid exchange lumen. The guidewire lumen proximal of the guidewire proximal port may be blocked or otherwise plugged and there may not be a connector on the proximal hub that is fluidly coupled with the guidewire lumen.

Figure 24D:
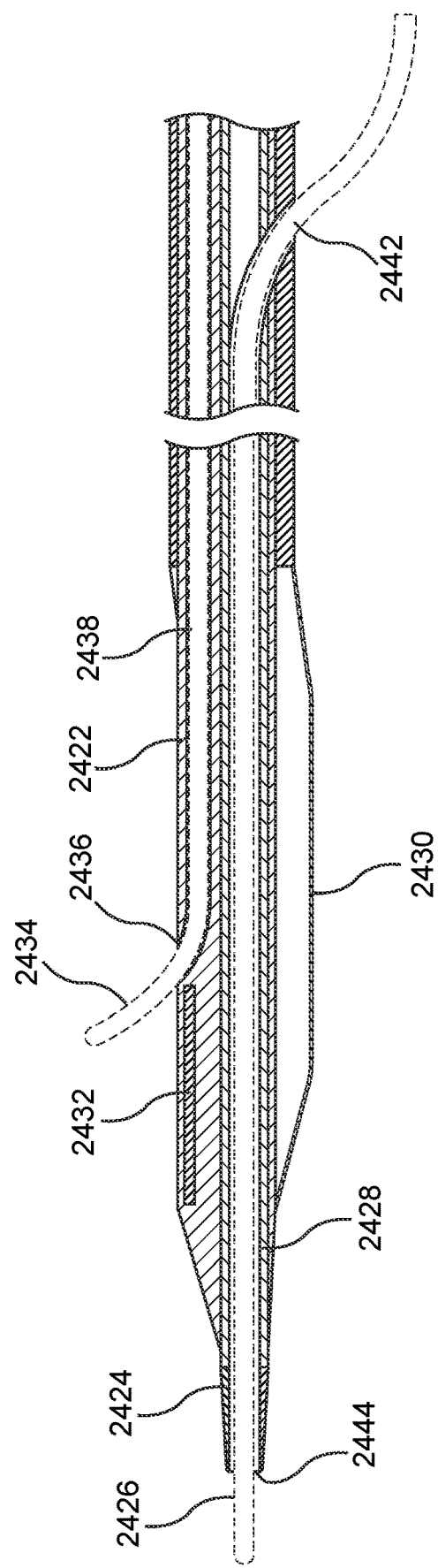

FIG. 24D shows an example of a re-entry catheter 2422 with the guidewire lumen having a rapid exchange configuration and the re-entry wire lumen having an over the wire configuration. The re-entry catheter has a guidewire lumen 2428 and a re-entry wire lumen 2438. The catheter 2422 includes the optional balloon 2430 and also has an ultrasound transducer 2432. The distal port 2444 allows a guidewire 2426 to exit the distal portion 2424 of the catheter and a re-entry port 2436 allows a re-entry wire 2434 to exit re-entry lumen 2438 of the catheter. The re-entry port may be proximal of the ultrasound transducer. In other examples, the re-entry port may be distal of the ultrasound transducer, while in other examples, the re-entry port may be in the middle of the ultrasound transducer. The proximal re-entry port (not illustrated) is disposed closer to the proximal-most end of the catheter than the distal end of the catheter, therefore the re-entry lumen is an over the wire lumen and there may be a connector on the proximal hub that is fluidly connected with the re-entry lumen. The guidewire proximal port 2442 is closer to the distal end of the catheter than the proximal-most end of the catheter, therefore the guidewire lumen is a rapid exchange lumen. Therefore, the guidewire lumen proximal of the guidewire proximal port may be blocked or plugged and there may not be a connector on the proximal hub that is fluidly coupled with the guidewire lumen.

Figure 24E:
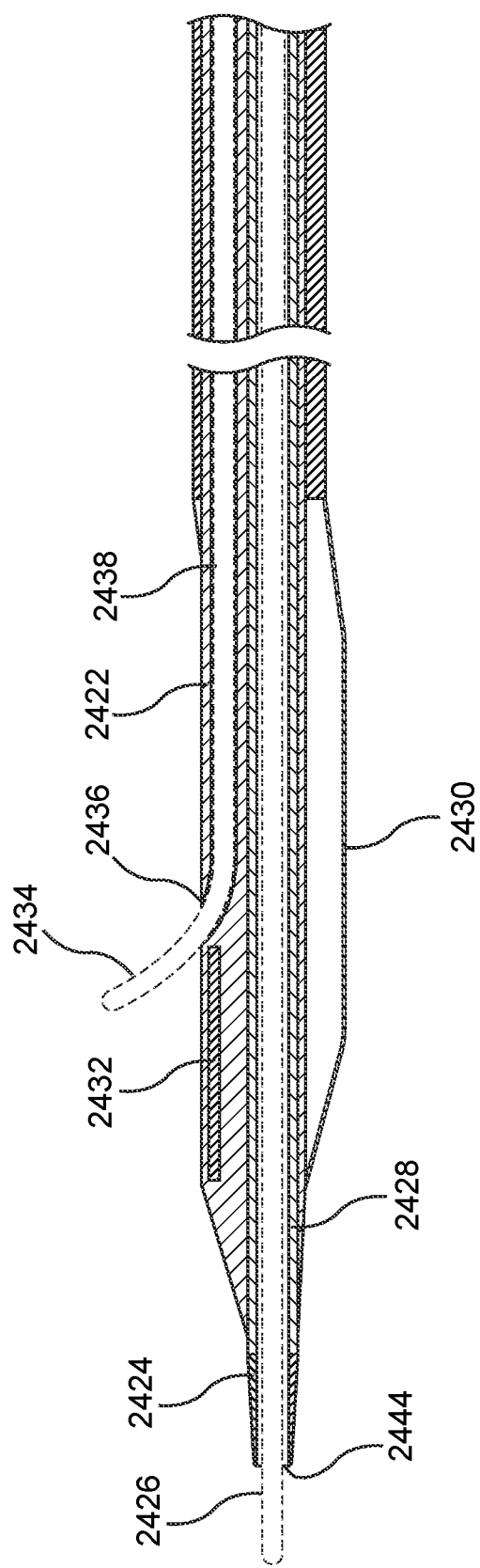

FIG. 24E shows an example of a re-entry catheter 2422 with both the guidewire lumen and the re-entry wire lumen in an over the wire configuration. The re-entry catheter has a guidewire lumen 2428 and a re-entry wire lumen 2438. The catheter 2422 includes the optional balloon 2430 and also has an ultrasound transducer 2432. The distal port 2444 allows a guidewire 2426 to exit the distal portion 2424 of the catheter and a re-entry port 2436 allows a re-entry wire 2434 to exit re-entry lumen 2438 of the catheter. The re-entry port may be proximal of the ultrasound transducer. The proximal re-entry port (not illustrated) is disposed closer to the proximal-most end of the catheter than the distal end of the catheter, therefore the re-entry lumen is an over the wire lumen. The guidewire proximal port (not illustrated) is closer to the proximal-most end of the catheter than the distal end of the catheter, therefore the guidewire lumen is also an over the wire lumen. Both the re-entry lumen and the guidewire lumen may each have connectors that are fluidly connected with their respective lumens on the proximal hub.

Figure 24F:
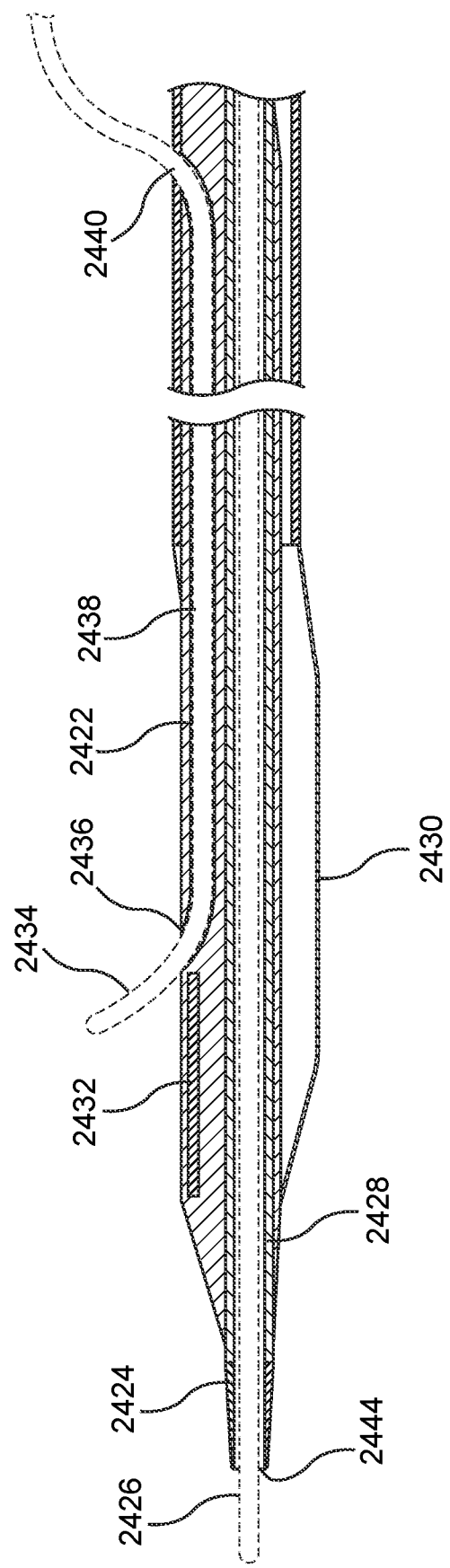

FIG. 24F shows an example of a re-entry catheter 2422 with a re-entry lumen having a rapid exchange configuration and a guidewire lumen having an over the wire configuration. The re-entry catheter has a guidewire lumen 2428 and a re-entry wire lumen 2438. The catheter 2422 includes the optional balloon 2430 and also has an ultrasound transducer 2432. The distal port 2444 allows a guidewire 2426 to exit the distal portion 2424 of the catheter and a re-entry port 2436 allows a re-entry wire 2434 to exit re-entry lumen 2438 of the catheter. The re-entry port may be proximal of the ultrasound transducer. The proximal re-entry port 2440 is disposed closer to the distal end of the catheter than the proximal-most end of the catheter, therefore the re-entry lumen is a rapid exchange lumen. The re-entry lumen proximal of the re-entry proximal port may be blocked or plugged and there may not be a connector at the proximal hub that is fluidly coupled with the re-entry lumen. The guidewire proximal port (not shown) is closer to the proximal-most end of the catheter than the distal end of the catheter, therefore the guidewire lumen is an over the wire lumen and there may be a connector at the proximal hub that is fluidly coupled with the guidewire lumen.

Use of Radiopaque or Echogenic Markers

In some examples, it may be desirable to provide a re-entry catheter that does not include an ultrasound transducer for imaging the vessel to ensure that the re-entry wire enters the true lumen in a desired location. Removing the transducer reduces cost, makes manufacturing easier, and may result in a catheter that is lower profile, more flexible and can track tortuous vessels better. The resulting smaller profile also allows the catheter to be used in smaller vessels. However, without the ultrasound transducer, it can be challenging to ensure that the re-entry port is in the right position that will direct the re-entry wire into the true lumen.

Figure 25:
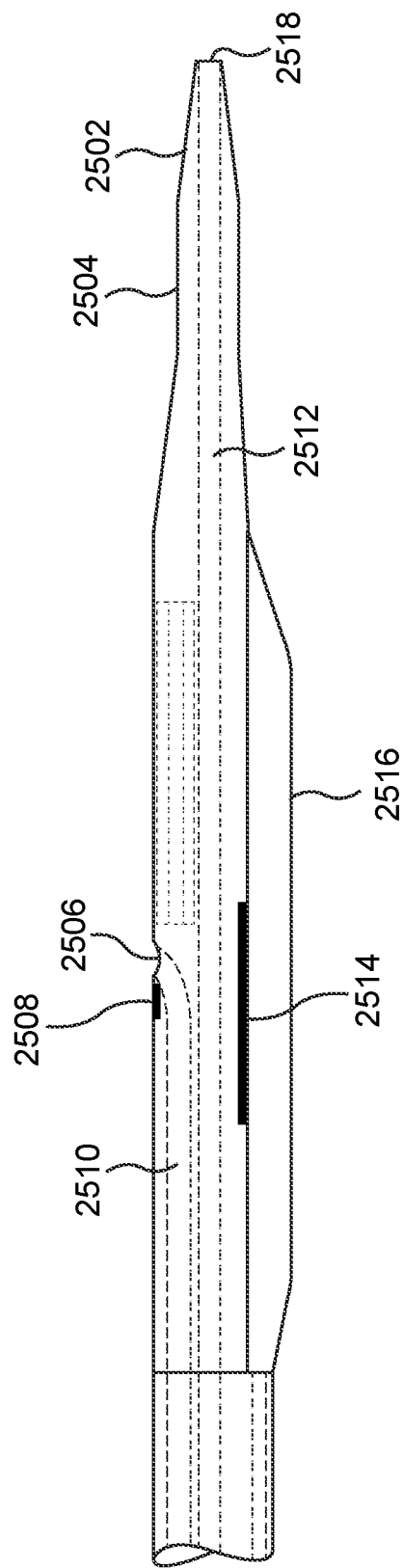
FIG. 25 shows an example of a catheter with radiopaque markers.

FIG. 25 shows an example of a re-entry catheter with radiopaque markers that can be used to visualize the re-entry port and distal portion of the catheter to ensure proper positioning. The ultrasound transducer has been omitted. The re-entry catheter 2502 in this example includes a separate lumen 2510 for the re-entry wire and a second lumen 2512 for the guidewire with distal exit port 2518. A re-entry port 2506 is adjacent the distal portion 2504 of the catheter. The catheter may include an optional radially expandable member 2516 such as a balloon to help anchor the catheter and displace the re-entry port radially inward toward the true lumen. A radiopaque marker 2508 is disposed adjacent the re-entry port 2506 so that under fluoroscopy the operator will know where the re-entry port is. The catheter may also include a second radiopaque marker 2514 that can be used to help align the catheter and re-entry port with the vessel and true lumen. Here, the first radiopaque marker 2508 is a small circular dot just proximal of the re-entry port 2506 although it may be proximal or distal of the re-entry port. The second radiopaque marker 2514 in this example is a linear radiopaque marker that may be rectangularly shaped and disposed under the first radiopaque marker, 180 degrees circumferentially offset from the first marker. The marker shape is not intended to be limiting and other geometries are contemplated, for example two linear shaped markers may be used that are transverse to one another and on opposite sides of the catheter shaft. Additional disclosure is provided below on how the two markers may be used to position the catheter. In this example, the markers are radiopaque markers formed from high density materials such as gold, platinum, tantalum, or other materials known in the art. However, in other examples, the markers could also be echogenic markers that show up under ultrasound imaging. Other aspects of the catheter are generally the same as examples with separate re-entry wire and guidewire lumens previously described above.

Figure 26:
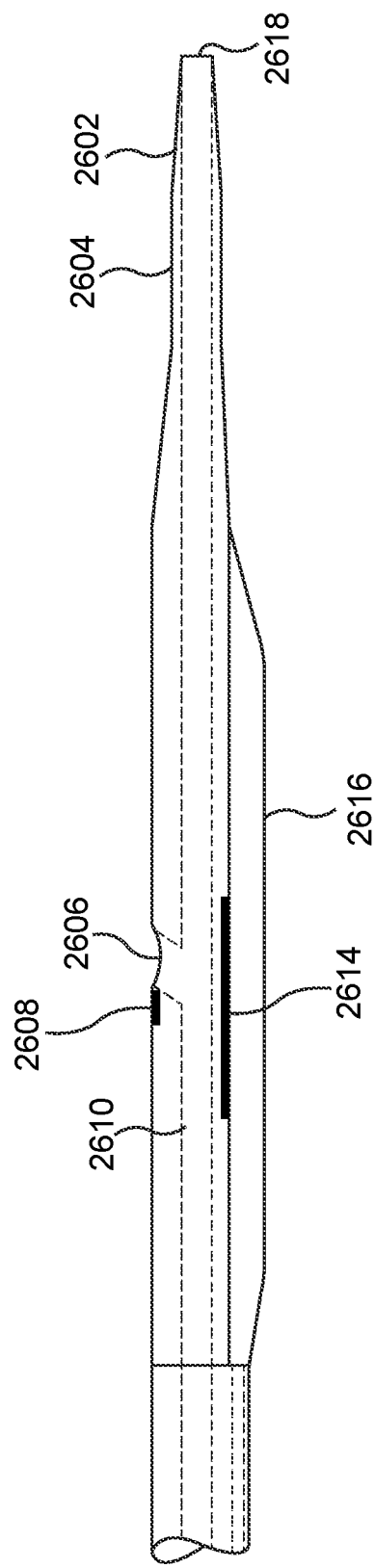
FIG. 26 shows another example of a catheter with radiopaque markers.

FIG. 26 is another example of a re-entry wire catheter 2602 but this time the catheter has a single common lumen for both the re-entry wire and the guidewire. This example also does not include an ultrasound transducer and therefore has radiopaque markers for visualizing the re-entry port and distal portion of the catheter to ensure proper positioning. The re-entry catheter 2602 in this example includes a common lumen 2610 for the re-entry wire and for the guidewire with distal exit port 2618. A re-entry port 2606 is adjacent the distal portion 2604 of the catheter. The catheter may include an optional radially expandable member 2616 such as a balloon to help anchor the catheter and displace the re-entry port radially inward toward the true lumen. A radiopaque marker 2608 is disposed adjacent the re-entry port 2606 so that under fluoroscopy the operator will know where the re-entry port is. The catheter may also include a second radiopaque marker 2614 that can be used to help align the catheter and re-entry port with the vessel and true lumen. Here, the first radiopaque marker 2608 is a small circular dot just proximal of the re-entry port 2606 although it may be distal of the re-entry port. The second radiopaque marker 2614 in this example is a linear radiopaque marker that may be rectangularly shaped and disposed under the first radiopaque marker, 180 degrees circumferentially offset from the first marker. However, this is not intended to be limiting and any shape may be used including those previously discussed above with respect to FIG. 25. Additional disclosure is provided below on how the two markers may be used to position the catheter. In this example, the markers are radiopaque markers formed from high density materials such as gold, tantalum, platinum, or other materials known in the art. However, in other examples, the markers could also be echogenic markers that show up under ultrasound imaging. Other aspects of the catheter are generally the same as examples with separate re-entry wire and guidewire lumens previously described above.

Example—Use of a Re-Entry Catheter with Markers

Figure 27A:
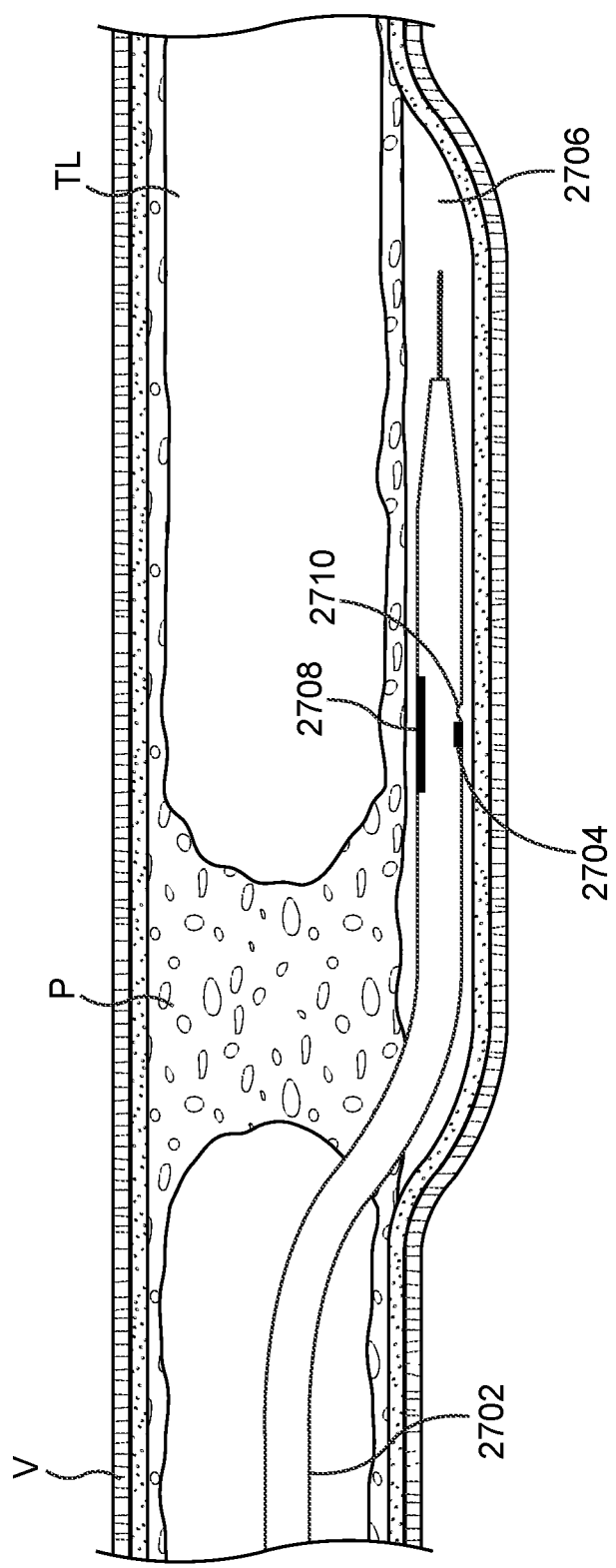
FIGS. 27A-27C show an example of using one of the catheters illustrated in FIG. 25 or 26 to treat an obstruction in a vessel.
Figure 27B:
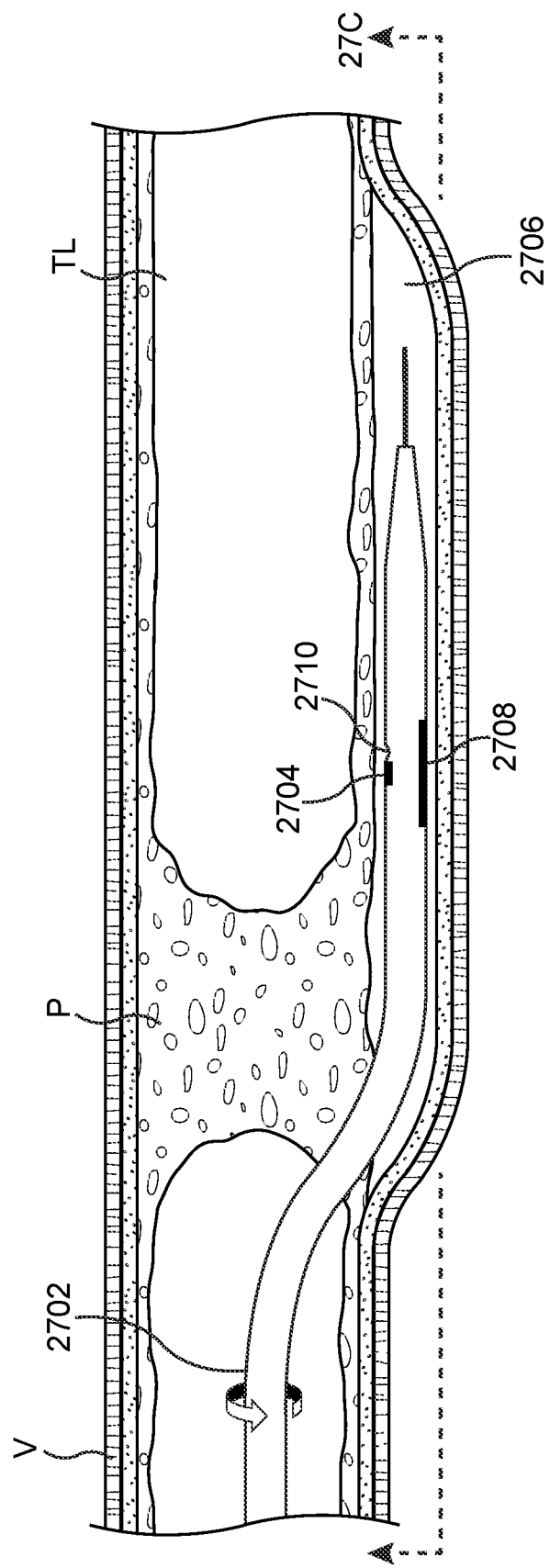
Figure 27C:
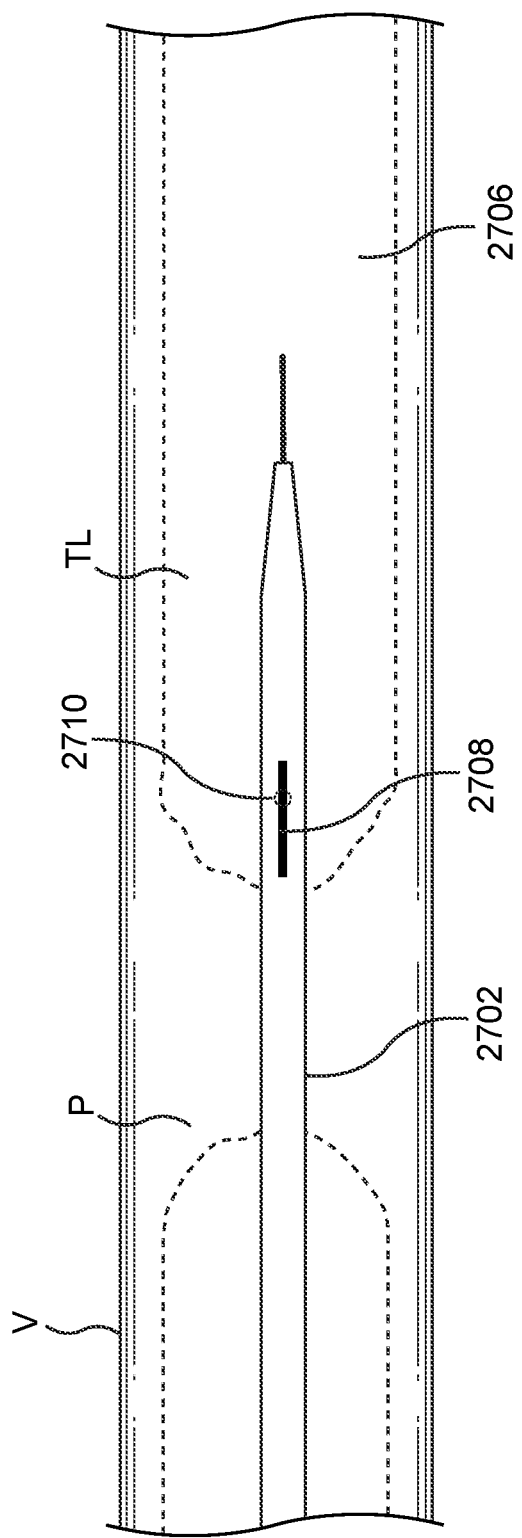

FIGS. 27A-27C show an example where a catheter such as the one shown in either FIG. 25 or FIG. 26 is used to treat a patient.

In FIG. 27A, the re-entry catheter 2702 which may be any of the catheters described herein, but in this example does not have an ultrasound transducer and therefore has two radiopaque markers 2704, 2708. The catheter is delivered to the obstructive plaque P and across the obstructive plaque via the subintimal space 2706 in the same manner as previously described above for either the single common lumen re-entry catheter or for the dual lumen re-entry catheter. In this example, once the distal portion of the catheter 2702 is advanced and is distal of the obstructive plaque P, proper positioning can be verified using fluoroscopy to observe the radiopaque markers. Dilute contrast media may be introduced into the treatment vessel from collateral vessels. In this example, the upper marker 2704 which in this example is a small circular dot is used to identify the re-entry port location which is facing downward and away from the true lumen TL, while the lower marker 2708 in this example is a long rectangular shaped marker and is facing the true lumen.

FIG. 27B shows that the physician or operator can then torque the catheter 2702 and rotate it until the dot shaped marker 2704 is rotated so that it is on the top and closest to, and facing the true lumen. Now the rectangular marker 2708 is on the bottom while the dot shaped marker 2704 is on the top. The re-entry port 2710 is also shown facing the true lumen TL and distal of the obstructive plaque P. When the re-entry port is optimally positioned, the distance between the two markers 2708, 2704 will be maximized in this view.

FIG. 27C shows an orthogonal view relative to FIG. 27B. In this example, when the re-entry port marker (the circular dot 2704) is aligned with the rectangular marker 2708, the re-entry port marker will be at least partially hidden by the rectangular marker and therefore the rectangular marker 2708 is seen on fluoroscopy and the re-entry port marker will be largely obscured or only partially visible depending on its size. This lets the physician know that the re-entry port is properly aligned with the true lumen TL because the re-entry port marker is directly under the rectangular marker. An operator may wish to take several other fluoroscopic images to ensure that the re-entry port is appropriately aligned with the true lumen based on observation of the radiopaque markers. Once the re-entry catheter has been delivered and aligned into a desired position using the radiopaque markers, the remainder of the procedure as previously described above with respect to use of a single common lumen device or a device with two separate lumens may be followed. In other examples, where the radiopaque markers are both linear or rectangular shaped markers that are transverse to one another (e.g. one runs axially along the longitudinal axis of the catheter while the second runs circumferentially around the catheter shaft), the resulting image would be a cross where the markers intersect perpendicularly relative to one another when proper alignment is achieved.

Example—Ultrasound Transducer Position

In the examples described above, the ultrasound transducer is disposed distal of the re-entry port. However, this is not intended to be limiting and in any of the examples of re-entry catheters described herein, the ultrasound transducer may also be disposed proximal of the re-entry port.

Figure 28:
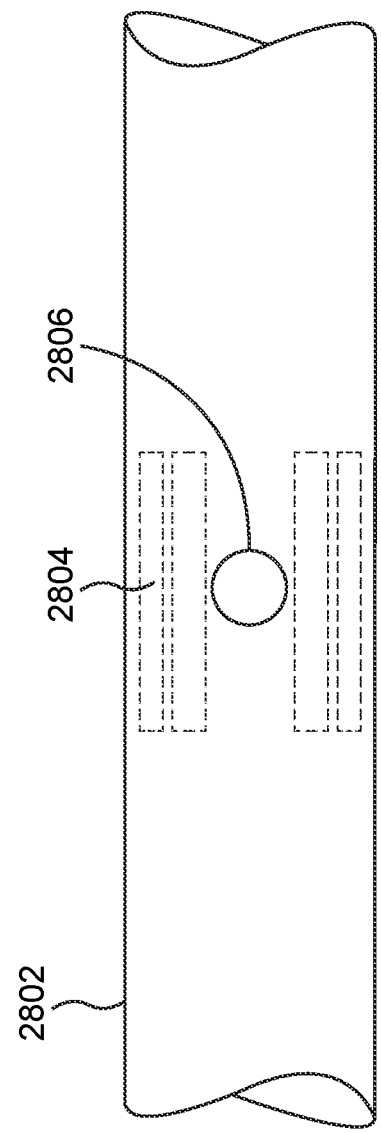
FIG. 28 shows an example of a re-entry port disposed in an ultrasound transducer.

FIG. 28 shows another example of a re-entry catheter 2802 which may be any of the re-entry catheters described herein, however in this example, the re-entry port 2806 is disposed in the middle of the ultrasound transducer 2804. Here, the ultrasound transducer is a phased array ultrasound transducer, but in other examples it may be any type of ultrasound transducer. A potential advantage of having the re-entry port disposed in the middle of the ultrasound transducer is that this may provide a better view of the re-entry wire as it exits the re-entry port and re-enters the true lumen.

Example—Multiple Re-Entry Ports

In the examples of re-entry catheters described above, only a single re-entry port is shown. However, in some cases is may be advantageous to provide a re-entry catheter with multiple re-entry ports which allow an operator to select which re-entry port to use in order to more accurately direct the re-entry wire back into the vessel true lumen. Any of the following examples of multiple re-entry ports may be used with any of the examples of re-entry catheters described herein.

Figure 29A:
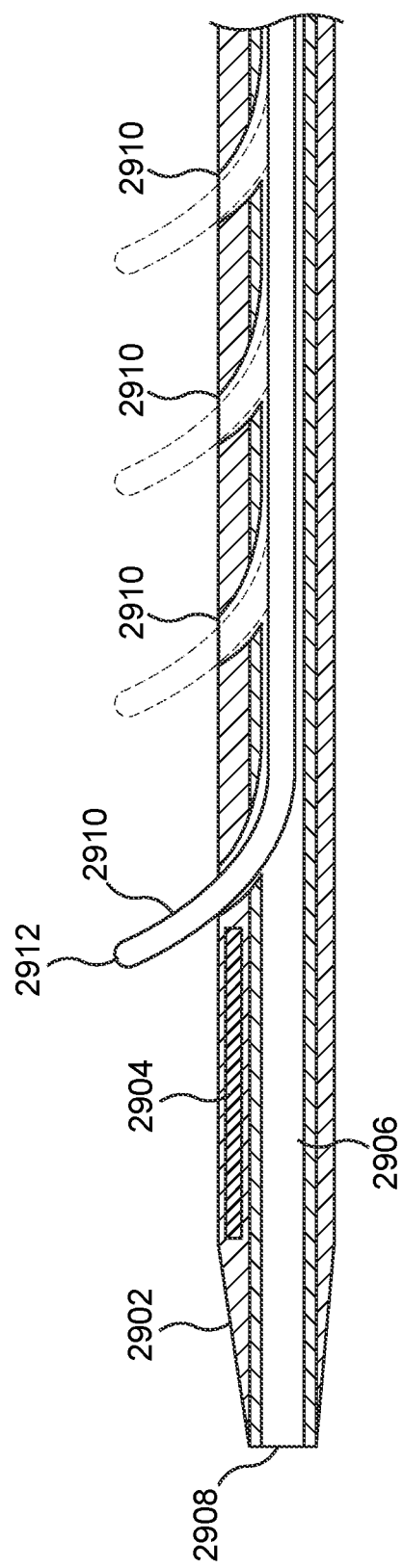
FIG. 29A shows an example of a re-entry catheter with a plurality of re-entry ports.

FIG. 29A shows an example of a distal portion of a re-entry catheter 2902 having a single common lumen for the delivery guidewire and the re-entry wire. The re-entry catheter may be any of the examples disclosed herein. Here, a delivery wire may pass through lumen 2906 and exit the distal port 2908, while the re-entry wire may pass through lumen 2906 and exit any of the re-entry ports 2910. The re-entry ports may be spaced in any desired pattern on the catheter. For example, here four re-entry ports are evenly spaced proximal of the ultrasound transducer 2904 and the operator may select which port to use for re-entry of the re-entry wire 2912 (re-entry wire also shown in phantom in the other ports). The ultrasound transducer may be positioned anywhere along the catheter relative to the re-entry ports. For example, the ultrasound transducer may be distal of all of the ports, proximal of all of the ports, or disposed between adjacent ports. In other examples, the re-entry ports may be disposed circumferentially around the catheter in a circular or clock pattern, or in a helical pattern.

Figure 29B:
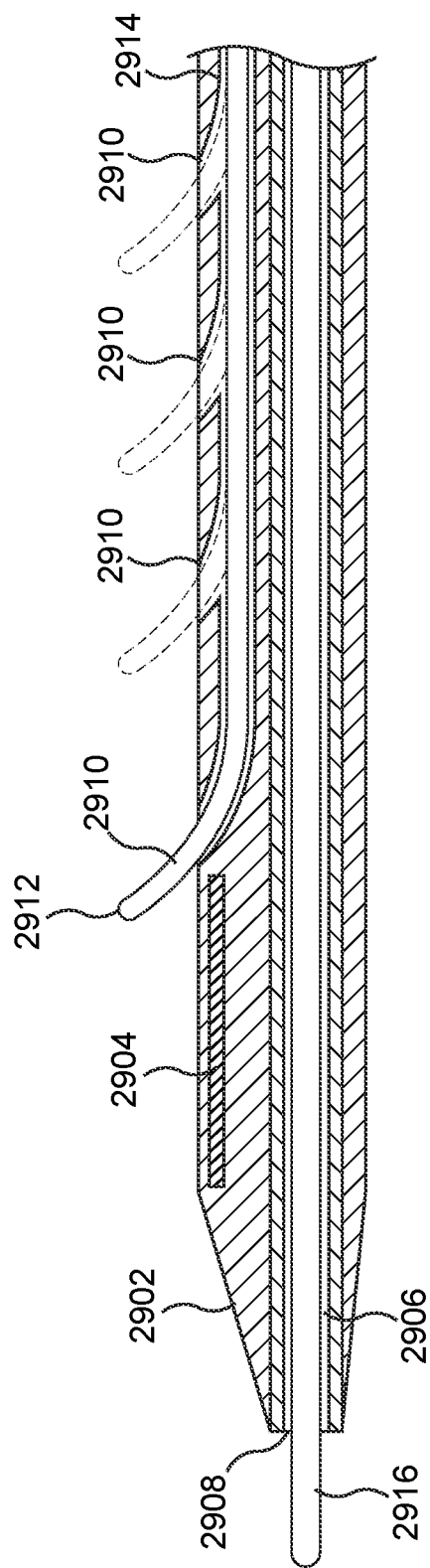
FIG. 29B shows another example of a re-entry catheter with a plurality of re-entry ports.

FIG. 29B shows an example of a distal portion of a re-entry catheter 2902 having a separate lumen 2906 for the delivery guidewire 2916 and a separate lumen 2914 for the re-entry wire 2912. The re-entry catheter may be any of the examples disclosed herein. Here, a delivery wire 2916 may pass through lumen 2906 and exit the distal port 2908, while the re-entry wire 2912 may pass through lumen 2914 and exit any of the re-entry ports 2910. The re-entry ports may be spaced in any desired pattern on the catheter. For example, here four re-entry ports are evenly spaced proximal of the ultrasound transducer 2904 and the operator may select which port to use for re-entry of the re-entry wire 2912 (re-entry wire also shown in phantom in the other ports). The ultrasound transducer 2904 may be positioned anywhere along the catheter relative to the re-entry ports. For example, the ultrasound transducer may be distal of all of the ports, proximal of all of the ports, or disposed between adjacent ports. In other examples, the re-entry ports may be disposed circumferentially around the catheter in a circular or clock pattern, or in a helical pattern.

NOTES AND EXAMPLES

The following, non-limiting examples, detail certain aspects of the present subject matter to solve the challenges and provide the benefits discussed herein, among others.

Example 1 is a catheter for facilitating re-entry of a re-entry wire into a true lumen of a blood vessel or into a desired region of the blood vessel, the catheter comprising: an elongate shaft having a proximal end, a distal end, and a first lumen extending therebetween; a distal port adjacent the distal end of the elongate shaft and fluidly coupled with the first lumen; a first proximal port proximal of the distal port and fluidly coupled with the first lumen; a wire re-entry port adjacent the distal end of the elongate shaft and proximal of the distal port, wherein the wire re-entry port has a re-entry axis; and an ultrasound transducer adjacent the re-entry port and configured to emit an ultrasound beam at an angle relative to a longitudinal axis of the elongate shaft, the ultrasound transducer configured to produce an image of the re-entry wire exiting the re-entry port and re-entering the true lumen.

Example 2 is the catheter of Example 1, wherein the catheter is a rapid exchange catheter wherein the first proximal port is closer to the distal end of the elongate shaft than the proximal end of the elongate shaft, and wherein the re-entry port is fluidly coupled with the first lumen.

Example 3 is the catheter of any of Examples 1-2, wherein the catheter is an over the wire catheter wherein the first proximal port is closer to the proximal end of the elongate shaft than the distal end of the elongate shaft, and wherein the re-entry port is fluidly coupled with the first lumen.

Example 4 is the catheter of any of Examples 1-3, wherein the re-entry axis of the wire re-entry port forms an angle of 30 degrees to less than 90 degrees relative to the longitudinal axis of the elongate shaft.

Example 5 is the catheter of any of Examples 1-4, wherein the ultrasound transducer is a phased array transducer, circumferentially disposed around the elongate shaft greater than 0 degrees and less than or equal to 270 degrees.

Example 6 is the catheter of any of Examples 1-5, wherein the ultrasound transducer is a flat planar transducer disposed over the elongate shaft.

Example 7 is the catheter of any of Examples 1-6, further comprising a radially expandable member disposed partially circumferentially around the elongate shaft, the radially expandable member having a collapsed configuration and an expanded configuration, wherein the collapsed configuration is suitable for delivery through the blood vessel, and wherein the expanded configuration is configured to anchor the distal end of the elongate shaft in the blood vessel or displace the wire re-entry port radially inward away from a wall of the blood vessel toward a desired re-entry location in the blood vessel.

Example 8 is the catheter of any of Examples 1-7, wherein the ultrasound transducer is disposed on a first side of the elongate shaft, and wherein the radially expandable member is disposed on a second side of the elongate shaft opposite the first side.

Example 9 is the catheter of any of Examples 1-8, wherein the radially expandable member is disposed under the wire re-entry exit port.

Example 10 is the catheter of any of Examples 1-9, wherein the radially expandable member is a balloon.

Example 11 is the catheter of any of Examples 1-10, further comprising an inflation lumen extending between the proximal and distal ends of the elongate shaft, the inflation lumen fluidly coupled with the balloon.

Example 12 is the catheter of any of Examples 1-11, wherein the wire re-entry port is fluidly coupled with the first lumen.

Example 13 is the catheter of any of Examples 1-12, further comprising a second lumen and a second proximal port, the second lumen extending between the proximal and distal ends of the elongate shaft, wherein the second lumen is fluidly coupled with the wire re-entry port and the second proximal port.

Example 14 is the catheter of any of Examples 1-13, wherein the catheter is a rapid exchange catheter wherein the second proximal port is closer to the distal end of the elongate shaft than the proximal end of the elongate shaft.

Example 15 is the catheter of any of Examples 1-14, wherein the catheter is an over the wire catheter wherein the second proximal port is closer to the proximal end of the elongate shaft than the distal end of the elongate shaft.

Example 16 is the catheter of any of Examples 1-15, further comprising an electrical cable extending between the proximal and distal ends of the elongate shaft, wherein the electrical cable is electrically coupled with the ultrasound transducer.

Example 17 is the catheter of any of Examples 1-16, wherein the wire re-entry port is proximal of the ultrasound transducer.

Example 18 is the catheter of any of Examples 1-17, wherein the image also shows advancement of the re-entry wire distally through the true lumen.

Example 19 is a catheter for facilitating re-entry of a re-entry wire into a true lumen of a blood vessel or a desired region of the blood vessel, the catheter comprising: an elongate shaft having a proximal end, a distal end, and a first lumen extending therebetween; a distal port adjacent the distal end of the elongate shaft and fluidly coupled with the first lumen; a first proximal port proximal of the distal port and fluidly coupled with the first lumen; a second lumen extending between the proximal end and distal end of the elongate shaft, the second lumen adjacent the first lumen; a second proximal port proximal of the distal port on the elongate shaft, wherein the second lumen is fluidly coupled with the second proximal port; a wire re-entry port adjacent the distal end of the elongate shaft and proximal of the distal port, wherein the wire re-entry port has a re-entry axis and is fluidly coupled with second lumen; and an ultrasound transducer adjacent the re-entry port and emitting an ultrasound beam at an angle relative to a longitudinal axis of the elongate shaft, the ultrasound transducer configured to produce an image of the re-entry wire exiting the re-entry port and re-entering the true lumen.

Example 20 is the catheter of Example 19, wherein the catheter is a rapid exchange catheter wherein the first proximal port is closer to the distal end of the elongate shaft than the proximal end of the elongate shaft.

Example 21 is the catheter of any of Examples 19-20, wherein the catheter is an over the wire catheter wherein the first proximal port is closer to the proximal end of the elongate shaft than the distal end of the elongate shaft.

Example 22 is the catheter of any of Examples 19-21, wherein the catheter is a rapid exchange catheter wherein the second proximal port is closer to the distal end of the elongate shaft than the proximal end of the elongate shaft.

Example 23 is the catheter of any of Examples 19-22 wherein the catheter is an over the wire catheter wherein the second proximal port is closer to the proximal end of the elongate shaft than the distal end of the elongate shaft.

Example 24 is the catheter of any of Examples 19-23, wherein the re-entry axis of the wire re-entry port forms an angle of 30 degrees to less than 90 degrees relative to the longitudinal axis of the elongate shaft.

Example 25 is the catheter of any of Examples 19-24, wherein the ultrasound transducer is a phased array transducer, circumferentially disposed around the elongate shaft less than or equal to 270 degrees.

Example 26 is the catheter of any of Examples 19-25, wherein the ultrasound transducer is a flat planar transducer.

Example 27 is the catheter of any of Examples 19-26, further comprising a radially expandable member disposed partially circumferentially around the elongate shaft, the radially expandable member having a collapsed configuration and an expanded configuration, wherein the collapsed configuration is suitable for delivery through the blood vessel, and wherein the expanded configuration is configured to anchor the distal end of the elongate shaft in the blood vessel or displace the wire re-entry exit port radially inward away from a wall of the blood vessel toward a desired re-entry location in the blood vessel.

Example 28 is the catheter of any of Examples 19-27, wherein the ultrasound transducer is disposed on a first side of the elongate shaft, and wherein the radially expandable member is disposed on a second side of the elongate shaft opposite the first side.

Example 29 is the catheter of any of Examples 19-28, wherein the radially expandable member is disposed under the wire re-entry exit port.

Example 30 is the catheter of any of Examples 19-29, wherein the radially expandable member is a balloon.

Example 31 is the catheter of any of Examples 19-30, further comprising an inflation lumen extending between the proximal and distal ends of the elongate shaft, the inflation lumen fluidly coupled with the balloon.

Example 32 is the catheter of any of Examples 19-31, further comprising an electrical cable extending between the proximal and distal ends of the elongate shaft, wherein the electrical cable is electrically coupled with the ultrasound transducer.

Example 33 is the catheter of any of Examples 19-32, wherein the wire re-entry port is proximal of the ultrasound transducer.

Example 34 is the catheter of any of Examples 19-33, wherein the image also shows advancement of the re-entry wire distally through the true lumen.

Example 35 is a method for treating an occluded blood vessel, the method comprising: advancing a catheter having an elongate shaft through the blood vessel toward the occlusion; passing a distal portion of the catheter through a subintimal space of the occluded vessel so that the distal portion of the catheter is distal of the occlusion; imaging a region of the occluded blood vessel distal of the occlusion with an ultrasound transducer coupled to the catheter, the ultrasound transducer configured to image the occluded blood vessel along an imaging axis; confirming that the image shows a desired position in the occluded vessel for re-entry of a wire from the subintimal space into a true lumen of the occluded blood vessel; and slidably moving a re-entry wire through a first lumen in the catheter and out a re-entry wire port in the catheter into the true lumen wherein the imaging axis allows imaging of the re-entry wire as it re-enters the true lumen.

Example 36 is the method of Example 35, wherein the ultrasound transducer is a phased array transducer, circumferentially disposed around the elongate shaft greater than 0 degrees and less than or equal to 270 degrees.

Example 37 is the method of any of Examples 35-36, wherein the ultrasound transducer is a flat planar transducer.

Example 38 is the method of any of Examples 35-37, further comprising radially expanding a radially expandable member coupled with the elongate shaft adjacent a distal end thereof, thereby anchoring the catheter in the blood vessel and displacing the wire re-entry port radially inward from a wall of the blood vessel toward a desired re-entry location in the occluded blood vessel.

Example 39 is the method of any of Examples 35-38, wherein the radially expandable member is a balloon, and radially expanding the radially expandable member comprises inflating the balloon with a fluid.

Example 40 is the method of any of Examples 35-39, wherein the catheter further comprises a distal port and a first proximal port, the distal port and the first proximal port fluidly coupled with the first lumen, and wherein the catheter is a rapid exchange catheter, wherein the first proximal port is closer to the distal portion of the catheter than a proximal portion of the catheter.

Example 41 is the method of any of Examples 35-40, wherein the catheter further comprises a distal port and a first proximal port, the distal port and the first proximal port fluidly coupled with the first lumen, and wherein the catheter is an over the wire catheter wherein the first proximal port is closer to a proximal portion of the catheter than the distal portion of the catheter.

Example 42 is the method of any of Examples 35-41, wherein the catheter further comprises a second lumen, a distal port and a proximal port, the distal port and the proximal port fluidly coupled with the second lumen, the method further comprising passing a guidewire through the proximal port, along the second lumen and out the distal port.

Example 43 is the method of any of Examples 35-42, wherein the catheter is a rapid exchange catheter, wherein the proximal port is closer to the distal portion of the catheter than a proximal portion of the catheter.

Example 44 is the method of any of Examples 35-43, wherein the catheter is an over the wire catheter, wherein the proximal port is closer to a proximal portion of the catheter than the distal portion of the catheter.

Example 45 is the method of any of Examples 35-44, wherein imaging of the re-entry wire comprises imaging of the re-entry wire as it is advanced distally through the true lumen.

Example 46 is a method for treating an occluded blood vessel, the method comprising: advancing a catheter having an elongate shaft through the blood vessel toward the occlusion, the elongate shaft having a first lumen and a second lumen; advancing the catheter over a guidewire slidably disposed in the first lumen; passing a distal portion of the catheter through a subintimal space so that the distal portion of the catheter is distal of the occlusion; imaging a region of the occluded blood vessel distal of the occlusion with an ultrasound transducer coupled to the catheter, the ultrasound transducer configured to image the occluded blood vessel along an imaging axis; confirming that the image shows a desired position in the occluded vessel for re-entry of a wire from the subintimal space into a true lumen of the occluded blood vessel; slidably moving a re-entry wire through the second lumen in the catheter and out a re-entry wire port in the catheter into the true lumen, wherein the imaging axis allows imaging of the re-entry wire as it re-enters the true lumen.

Example 47 is the method of Example 46, wherein the ultrasound transducer is a phased array transducer, circumferentially disposed around the catheter greater than 0 degrees and less than or equal to 270 degrees.

Example 48 is the method of any of Examples 46-47, wherein the ultrasound transducer is a flat planar transducer.

Example 49 is the method of any of Examples 46-48, further comprising radially expanding a radially expandable member coupled with the catheter adjacent a distal end thereof, thereby anchoring the catheter in the blood vessel and displacing the wire re-entry port radially inward from a wall of the blood vessel toward a desired re-entry location in the occluded blood vessel.

Example 50 is the method of any of Examples 46-49, wherein the radially expandable member is a balloon, and radially expanding the radially expandable member comprises inflating the balloon with a fluid.

Example 51 is the method of any of Examples 46-50, wherein imaging of the re-entry wire comprises imaging of the re-entry wire as it is advanced distally through the true lumen.

Example 52 is a catheter for facilitating re-entry of a re-entry wire into a true lumen of a blood vessel or a desired region of the blood vessel, the catheter comprising: an elongate shaft having a proximal end, a distal end, and a first lumen extending therebetween; a distal port adjacent the distal end of the elongate shaft and fluidly coupled with the first lumen; a first proximal port proximal of the distal port and fluidly coupled with the first lumen; a wire re-entry port adjacent the distal end of the elongate shaft and proximal of the distal port; and one or more radiopaque markers coupled to the elongate shaft and disposed adjacent the re-entry port, the one or more radiopaque markers configured to allow an operator to visualize and align the re-entry port under fluoroscopy to ensure that a re-entry wire exiting the re-entry port enters the true lumen of the blood vessel at a desired location.

Example 53 is the catheter of Example 52, wherein the catheter is a rapid exchange catheter wherein the first proximal port is closer to the distal end of the elongate shaft than the proximal end of the elongate shaft.

Example 54 is the catheter of any of Examples 52-53, wherein the catheter is an over the wire catheter wherein the first proximal port is closer to the proximal end of the elongate shaft than the distal end of the elongate shaft.

Example 55 is the catheter of any of Examples 52-54, further comprising a radially expandable member disposed partially circumferentially around the elongate shaft, the radially expandable member having a collapsed configuration and an expanded configuration, wherein the collapsed configuration is suitable for delivery through the blood vessel, and wherein the expanded configuration is configured to anchor the distal end of the elongate shaft in the blood vessel or displace the wire re-entry exit port radially inward away from a wall of the blood vessel toward a desired re-entry location in the blood vessel.

Example 56 is the catheter of an of Examples 52-55, wherein the radially expandable member is disposed under the wire re-entry exit port.

Example 57 is the catheter of any of Examples 52-56, wherein the radially expandable member is a balloon.

Example 58 is the catheter of any of Examples 52-57, further comprising an inflation lumen extending between the proximal and distal ends of the elongate shaft, the inflation lumen fluidly coupled with the balloon.

Example 59 is the catheter of any of Examples 52-58, wherein the wire re-entry port is fluidly coupled with the first lumen.

Example 60 is the catheter of any of Examples 52-59, further comprising a second lumen and a second proximal port, the second lumen extending between the proximal and distal ends of the elongate shaft, wherein the second lumen is fluidly coupled with the wire re-entry port and the second proximal port.

Example 61 is the catheter of any of Examples 52-60, wherein the catheter is a rapid exchange catheter wherein the second proximal port is closer to the distal end of the elongate shaft than the proximal end of the elongate shaft.

Example 62 is the catheter of any of Examples 52-61, wherein the catheter is an over the wire catheter wherein the second proximal port is closer to the proximal end of the elongate shaft than the distal end of the elongate shaft.

Example 63 is a method for treating an occluded blood vessel, the method comprising: advancing a catheter having an elongate shaft through the blood vessel toward the occlusion; passing a distal portion of the catheter through a subintimal space under the occlusion so that the distal portion of the catheter is distal of the occlusion; manipulating the catheter so that a re-entry wire port adjacent the distal portion of the catheter is in a desired position; observing one or more radiopaque markers on the catheter under fluoroscopy to confirm that the re-entry wire port is in the desired position; and slidably moving a re-entry wire through a first lumen in the catheter and out the re-entry wire port in the catheter to re-enter the true lumen of the blood vessel.

Example 64 is the method of Example 63, further comprising radially expanding a radially expandable member coupled with the elongate shaft adjacent a distal end thereof, thereby anchoring the catheter in the blood vessel and displacing the wire re-entry port radially inward from a wall of the blood vessel toward the desired re-entry position in the occluded blood vessel.

Example 65 is the method of any of Examples 63-64, wherein the radially expandable member is a balloon, and radially expanding the radially expandable member comprises inflating the balloon with a fluid.

In Example 66, the apparatuses or method of any one or any combination of Examples 1-65 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A catheter for facilitating re-entry of a re-entry wire into a true lumen of a blood vessel or into a desired region of the blood vessel, the catheter comprising:
   an elongate shaft having a proximal end, a distal end, and a first lumen extending therebetween;
   a distal port adjacent the distal end of the elongate shaft and fluidly coupled with the first lumen;

a first proximal port proximal of the distal port and fluidly coupled with the first lumen;

a wire re-entry port adjacent the distal end of the elongate shaft and proximal of the distal port, wherein the wire re-entry port has a re-entry axis; and an ultrasound transducer adjacent the re-entry port and configured to emit an ultrasound beam at an angle relative to a longitudinal axis of the elongate shaft, the ultrasound transducer configured to produce an image of the re-entry wire exiting the re-entry port and re-entering the true lumen.

2. The catheter of claim 1, wherein the catheter is a rapid exchange catheter wherein the first proximal port is closer to the distal end of the elongate shaft than the proximal end of the elongate shaft, and wherein the re-entry port is fluidly coupled with the first lumen.

3. The catheter of claim 1, wherein the catheter is an over the wire catheter wherein the first proximal port is closer to the proximal end of the elongate shaft than the distal end of the elongate shaft, and wherein the re-entry port is fluidly couple with the first lumen.

4. The catheter of claim 1, wherein the re-entry axis of the wire re-entry port forms an angle of 30 degrees to less than 90 degrees relative to the longitudinal axis of the elongate shaft.

5. The catheter of claim 1, wherein the ultrasound transducer is a phased array transducer, circumferentially disposed around the elongate shaft greater than 0 degrees and less than or equal to 270 degrees.

6. The catheter of claim 1, wherein the ultrasound transducer is a flat planar transducer disposed over the elongate shaft.

7. The catheter of claim 1, further comprising a radially expandable member disposed partially circumferentially around the elongate shaft, the radially expandable member having a collapsed configuration and an expanded configuration, wherein the collapsed configuration is suitable for delivery through the blood vessel, and wherein the expanded configuration is configured to anchor the distal end of the elongate shaft in the blood vessel or displace the wire re-entry port radially inward away from a wall of the blood vessel toward a desired re-entry location in the blood vessel.

8. The catheter of claim 7, wherein the ultrasound transducer is disposed on a first side of the elongate shaft, and wherein the radially expandable member is disposed on a second side of the elongate shaft opposite the first side.

9. The catheter of claim 7, wherein the radially expandable member is disposed under the wire re-entry exit port.

10. The catheter of claim 7, wherein the radially expandable member is a balloon.

11. The catheter of claim 10, further comprising an inflation lumen extending between the proximal and distal ends of the elongate shaft, the inflation lumen fluidly coupled with the balloon.

12. The catheter of claim 1, wherein the wire re-entry port is fluidly coupled with the first lumen.

13. The catheter of claim 1, further comprising a second lumen and a second proximal port, the second lumen extending between the proximal and distal ends of the elongate shaft, wherein the second lumen is fluidly coupled with the wire re-entry port and the second proximal port.

14. The catheter of claim 13, wherein the catheter is a rapid exchange catheter wherein the second proximal port is closer to the distal end of the elongate shaft than the proximal end of the elongate shaft.

15. The catheter of claim 13, wherein the catheter is an over the wire catheter wherein the second proximal port is closer to the proximal end of the elongate shaft than the distal end of the elongate shaft.

16. The catheter of claim 1, further comprising an electrical cable extending between the proximal and distal ends of the elongate shaft, wherein the electrical cable is electrically coupled with the ultrasound transducer.

17. The catheter of claim 1, wherein the wire re-entry port is proximal of the ultrasound transducer.

18. The catheter of claim 1, wherein the image also shows advancement of the re-entry wire distally through the true lumen.

19. A catheter for facilitating re-entry of a re-entry wire into a true lumen of a blood vessel or a desired region of the blood vessel, the catheter comprising:

an elongate shaft having a proximal end, a distal end, and a first lumen extending therebetween;

a distal port adjacent the distal end of the elongate shaft and fluidly coupled with the first lumen;

a first proximal port proximal of the distal port and fluidly coupled with the first lumen;

a second lumen extending between the proximal end and distal end of the elongate shaft, the second lumen adjacent the first lumen;

a second proximal port proximal of the distal port on the elongate shaft, wherein the second lumen is fluidly coupled with the second proximal port;

a wire re-entry port adjacent the distal end of the elongate shaft and proximal of the distal port, wherein the wire re-entry port has a re-entry axis and is fluidly coupled with second lumen; and an ultrasound transducer adjacent the re-entry port and emitting an ultrasound beam at an angle relative to a longitudinal axis of the elongate shaft, the ultrasound transducer configured to produce an image of the re-entry wire exiting the re-entry port and re-entering the true lumen.

20. The catheter of claim 19, wherein the catheter is a rapid exchange catheter wherein the first proximal port is closer to the distal end of the elongate shaft than the proximal end of the elongate shaft.

21. The catheter of claim 19, wherein the catheter is an over the wire catheter wherein the first proximal port is closer to the proximal end of the elongate shaft than the distal end of the elongate shaft.

22. The catheter of claim 19, wherein the catheter is a rapid exchange catheter wherein the second proximal port is closer to the distal end of the elongate shaft than the proximal end of the elongate shaft.

23. The catheter of claim 19, wherein the catheter is an over the wire catheter wherein the second proximal port is closer to the proximal end of the elongate shaft than the distal end of the elongate shaft.

24. The catheter of claim 19, wherein the re-entry axis of the wire re-entry port forms an angle of 30 degrees to less than 90 degrees relative to the longitudinal axis of the elongate shaft.

25. The catheter of claim 19, wherein the ultrasound transducer is a phased array transducer, circumferentially disposed around the elongate shaft less than or equal to 270 degrees.

26. The catheter of claim 19, wherein the ultrasound transducer is a flat planar transducer.

27. The catheter of claim 19, further comprising a radially expandable member disposed partially circumferentially around the elongate shaft, the radially expandable member having a collapsed configuration and an expanded configuration, wherein the collapsed configuration is suitable for delivery through the blood vessel, and wherein the expanded configuration is configured to anchor the distal end of the elongate shaft in the blood vessel or displace the wire re-entry exit port radially inward away from a wall of the blood vessel toward a desired re-entry location in the blood vessel.

28. The catheter of claim 27, wherein the ultrasound transducer is disposed on a first side of the elongate shaft, and wherein the radially expandable member is disposed on a second side of the elongate shaft opposite the first side.

29. The catheter of claim 27, wherein the radially expandable member is disposed under the wire re-entry exit port.

30. The catheter of claim 27, wherein the radially expandable member is a balloon.

31. The catheter of claim 30, further comprising an inflation lumen extending between the proximal and distal ends of the elongate shaft, the inflation lumen fluidly coupled with the balloon.

32. The catheter of claim 19, further comprising an electrical cable extending between the proximal and distal ends of the elongate shaft, wherein the electrical cable is electrically coupled with the ultrasound transducer.

33. The catheter of claim 19, wherein the wire re-entry port is proximal of the ultrasound transducer.

34. The catheter of claim 19, wherein the image also shows advancement of the re-entry wire distally through the true lumen.

* * * * *